United States Patent
Toba et al.

(10) Patent No.: US 8,617,722 B2
(45) Date of Patent: *Dec. 31, 2013

(54) POLYMER COMPOUND AND ORGANIC ELECTROLUMINESCENCE ELEMENT USING THE SAME

(75) Inventors: Masahiko Toba, Chiba (JP); Tsuyoshi Kato, Chiba (JP)

(73) Assignee: Showa Denko K.K., Tokyo (JP)

( * ) Notice: Subject to any disclaimer, the term of this patent is extended or adjusted under 35 U.S.C. 154(b) by 499 days.

This patent is subject to a terminal disclaimer.

(21) Appl. No.: 12/918,742

(22) PCT Filed: Feb. 20, 2009

(86) PCT No.: PCT/JP2009/052955
§ 371 (c)(1),
(2), (4) Date: Aug. 20, 2010

(87) PCT Pub. No.: WO2009/104708
PCT Pub. Date: Aug. 27, 2009

(65) Prior Publication Data
US 2010/0327738 A1    Dec. 30, 2010

(30) Foreign Application Priority Data

Feb. 22, 2008   (JP) ................. 2008-041902

(51) Int. Cl.
    *H01L 51/54*   (2006.01)
(52) U.S. Cl.
    USPC ........... 428/690; 428/917; 313/504; 313/505; 313/506; 257/40; 257/E51.05; 257/E51.026; 257/E51.032; 546/24; 546/79; 546/81; 546/110; 548/440
(58) Field of Classification Search
    USPC ................. 428/690, 917; 313/504, 505, 506; 257/40, E51.026, E51.05, E51.032; 546/24, 79, 81, 101; 548/440
    See application file for complete search history.

(56) References Cited

U.S. PATENT DOCUMENTS

| | | | |
|---|---|---|---|
| 6,730,417 B2 * | 5/2004 | Hu et al. ...................... | 428/690 |
| 2002/0055014 A1 * | 5/2002 | Okada et al. ................. | 428/690 |

(Continued)

FOREIGN PATENT DOCUMENTS

| | | |
|---|---|---|
| JP | 8-157575 A | 6/1996 |
| JP | 10-1665 A | 1/1998 |

(Continued)

OTHER PUBLICATIONS

Behl, Marc et al.; "Block Copolymers Build-up of Electron and Hole Transport Materials"; Macromolecular Chemistry and Physics, 2004, 205, pp. 1633-1643.

(Continued)

*Primary Examiner* — Gregory Clark
(74) *Attorney, Agent, or Firm* — Sughrue Mion, PLLC

(57) ABSTRACT

The present invention provides a polymer material capable of preparing organic EL elements having low driving voltage and high durability. The polymer compound of the present invention includes a constituting unit derived from a monomer represented by the formula (1);

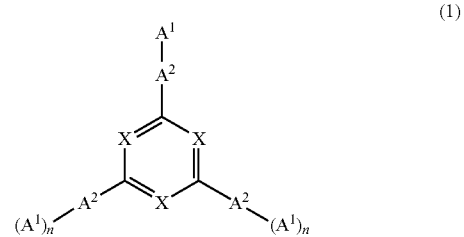

(in the formula (1), each of $A^1$'s is independently a condensed polycyclic aromatic group optionally having a heteroatom as a ring-constituting atom; the condensed polycyclic aromatic group links to $A^2$ at the meta position to the bonding position of the ring represented by the following formula;

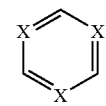

each of $A^2$'s is independently a six-membered ring aromatic group optionally having a heteroatom as a ring-constituting atom; at least one of $A^1$ and $A^2$ has a substituent having a polymerizable functional group; at least one of X's is a nitrogen atom, and n's are independently 1 or 2).

15 Claims, 1 Drawing Sheet

(56) References Cited

U.S. PATENT DOCUMENTS

2003/0186080 A1* 10/2003 Kamatani et al. .............. 428/690
2007/0138953 A1* 6/2007 Tobise .......................... 313/506

FOREIGN PATENT DOCUMENTS

| | | |
|---|---|---|
| JP | 2002-129155 A | 5/2002 |
| JP | 2003-22893 A | 1/2003 |
| JP | 2004-185967 A | 7/2004 |
| JP | 2006-173569 A | 6/2006 |
| JP | 2006-188493 A | 7/2006 |
| JP | 2006-225428 A | 8/2006 |
| JP | 2007-153917 A | 6/2007 |
| JP | 2007-169541 A | 7/2007 |
| JP | 2007-269895 A | 10/2007 |
| JP | 2008-28119 A | 2/2008 |
| WO | 03/080760 A1 | 2/2003 |

OTHER PUBLICATIONS

Oh, Se Young et al.; "Characteristics of Polymer Light Emitting Diode Using a Phosphorescent Terpolymer Containing Perylene, Triazine and Ir(ppy)$_3$"; Molecular Crystals and Liquid Crystals, 2006, 458, pp. 227-235.

Yamamoto, Toshihide et al.; "Palladium-Catalyzed Synthesis of Triarylamines from Aryl Halides and Diarylamines"; Tetrahedron Letters, 1998, vol. 39, pp. 2367-2370.

* cited by examiner

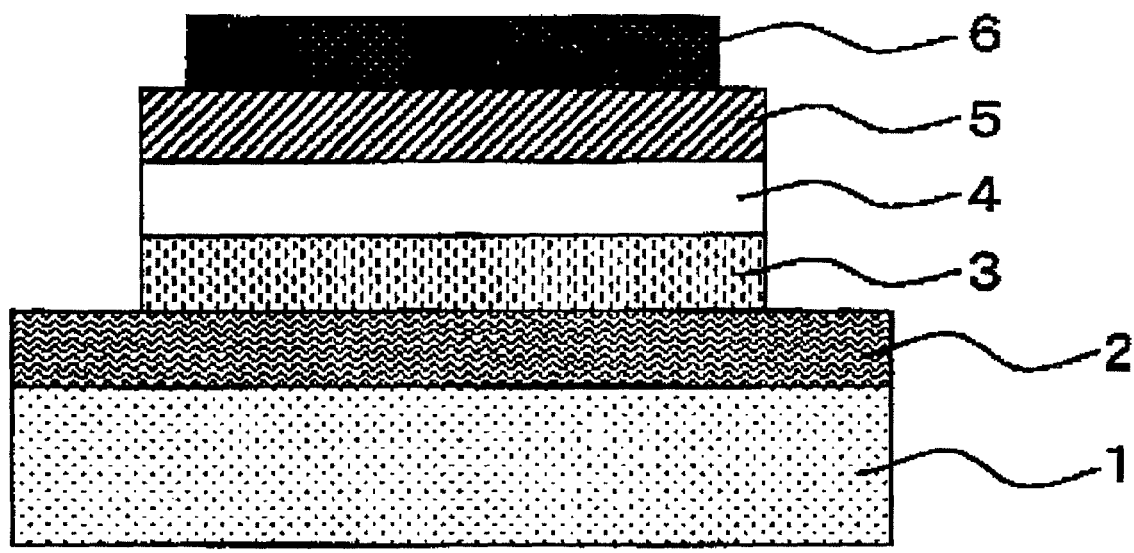

POLYMER COMPOUND AND ORGANIC ELECTROLUMINESCENCE ELEMENT USING THE SAME

TECHNICAL FIELD

The present invention relates to a polymer compound containing an aromatic hetero ring. More particularly, the present invention relates to a polymer compound containing an aromatic hetero ring which compound has electron-transporting properties and hole-transporting properties and is suitable to organic electroluminescence elements (hereinafter optionally referred to "organic EL element").

TECHNICAL BACKGROUND

Electroluminescence elements using organic thin films, namely, organic EL elements generally comprise a substrate and thereon, an anode electrode, a cathode electrode and, between them, an organic layer containing at least a luminous layer. As the organic layer, a positive hole injecting layer (anode buffer layer), a positive hole-transporting layer, a positive hole blocking layer, an electron-transporting layer and an electron injecting layer are provided in addition to the luminous layer. In general, these layers are laminated between an anode electrode and a cathode electrode to form an organic EL element.

Non-patent document 1 discloses a synthetic example of a non-conjugated polymer having a triazine skeleton represented by the following formula (i) which polymer can be potentially applied to organic EL elements and electric field effect transistors.

Patent document 2 discloses an organic EL element obtainable by using an azomethine fluorescence emission material having a triazine ring, and non-patent document 2 discloses an example of a process of producing an organic EL element obtainable by using a non-conjugated polymer having a triazine skeleton.

Patent document 3 discloses a compound represented by the following formulas (ii) which is an amine derivative having a heterocyclic group as a bipolar compound that a substituent having hole-transporting ability is introduced into an aromatic complex derivative having electron-transporting ability. As described above, since the position of the diphenyl triazine ring group on the aromatic group is a para-position to a nitrogen atom of a diphenylamino group or a nitrogen atom of a carbazolyl group, the nitrogen atom and a nitrogen atom present on the heterocyclic group have a conjugatable structure. Therefore, the compound easily forms an excimer and polarization phenomenon of electric charge in a molecule is caused remarkably and thereby a triplet excitation level becomes relatively low. For the above reasons, organic EL elements having phosphorescent properties obtainable by using such a compound, particularly an organic EL element having phosphorescent properties which emits light having a short wavelength have a problem on durability.

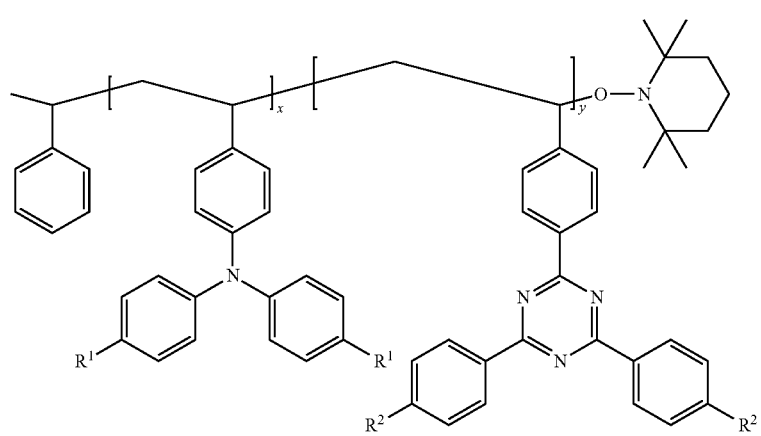

(i)

In the formula, each $R^1$ is independently hydrogen, a methyl group or an n-butyl group; each $R^2$ is independently hydrogen, a methyl group, an ethyl group, an isopropyl group, a t-butyl group, an octyl group or a methoxy group; and x and y are independently an integer of not less than 1.

Further, Patent document 1 discloses an organic EL element obtainable by using a triazine derivative having a perfluorophenylene derivative as a substituent. When an organic layer of the organic EL element is produced from such a low molecular compound, a vacuum vapor deposition method is generally used. The vacuum vapor deposition method has problems such that vacuum equipment is necessary and the film thickness of the organic layer formed is liable to be uneven.

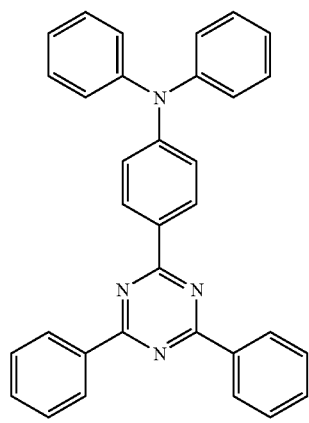

(ii)

-continued

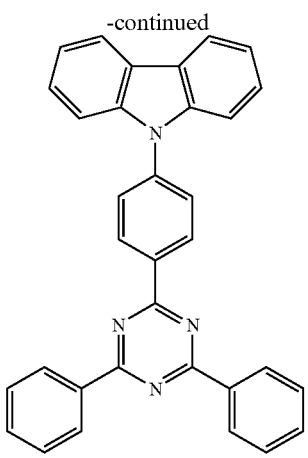

Patent documents 4 and 5 disclose the compounds represented by the following formulas (iii) and (iv) as an electric charge-transporting material used for organic EL elements having phosphorescent properties.

These compounds have a structure which hardly makes an excimer, but have a glass transition point of about 100 to 200° C. and have a problem on heat resistance. Furthermore, in preparing an organic layer of organic EL elements using these compounds, the low molecular compound as disclosed in Patent document 4 or 5 is formed to a film by a vapor deposition method, and thereby the production process of the organic EL elements is complicated.

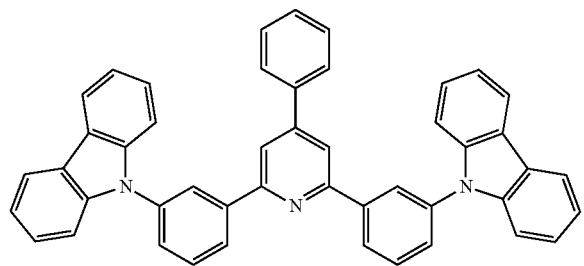

(iii)

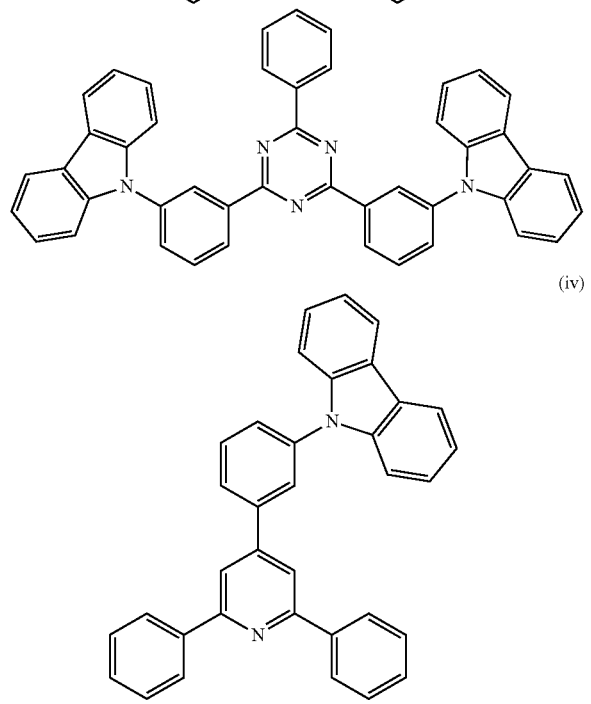

(iv)

Patent Document 1: JP-A-2006-173569
Patent Document 2: JP-A-2002-129155
Patent Document 3: JP-A-2003-22893
Patent Document 4: WO03/080760
Patent Document 5: JP-A-2006-188493
Non-Patent Document 1: Macromolecular Chemistry and Physics, 2004, 205, 1633-1643
Non-Patent Document 2: Molecular Crystals and Liquid Crystals, 2006, 458, 227-235.

DISCLOSURE OF THE INVENTION

Subject to be Solved by the Invention

With respect to the organic EL elements prepared using the above-described low molecular compounds and the polymer compounds, there is still room for improvement on driving voltage and durability. Therefore, it is an object of the present invention to provide a polymer compound capable of preparing organic EL elements having low driving voltage and high durability and to provide an organic EL element obtainable by using the compound.

Means for Solving the Subject

The present inventors have been earnestly studied for solving the above subjects and found that an organic EL element prepared by using a polymer compound having a specific aromatic heterocyclic structure as an electron-transporting site and a hole-transporting site of the organic EL element (hereinafter the electron-transporting and the hole-transporting are optionally referred to "carrier-transporting" together) has low driving voltage and high durability. Thus, the present invention has been accomplished.

The resent invention relates to the following characteristics [1] to [20].

[1] The high molecular compound of the present invention comprises a constituting unit derived from a monomer represented by the following formula (1).

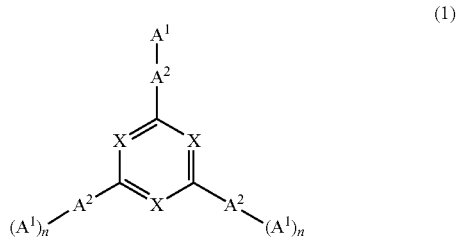

(1)

In the formula (1), each of plural $A^1$'s is independently an aromatic group optionally having a heteroatom as a ring-constituting atom, hydrogen atom, a halogen atom, an amino group, an alkyl group having 1 to 12 carbon atoms, an alkoxy group having 1 to 12 carbon atoms or an aryloxy group having 6 to 10 carbon atoms;

at least one of plural $A^1$'s is a condensed polycyclic aromatic group optionally having a heteroatom as a ring-constituting atom;

the condensed polycyclic aromatic group links to $A^2$ at the meta position to the bonding position of the ring represented by the following formula;

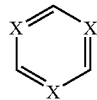

each of three $A^2$'s is independently a six-membered ring aromatic group optionally having a heteroatom as ring-constituting atom;

each of hydrogen atoms directly bonded to the ring-constituting atoms in $A^1$ and $A^2$ may be independently substituted by an aromatic group optionally having a heteroatom as a ring-constituting atom, a halogen atom, an amino group, an alkyl group having 1 to 12 carbon atoms, an alkoxy group having 1 to 12 carbon atoms or an aryloxy group having 6 to 10 carbon atoms;

at least one of $A^1$ and $A^2$ has a substituent having a polymerizable functional group;

each of three X's is independently a carbon atom to which one hydrogen atom is bonded, or a nitrogen atom, and at least one of three X's is a nitrogen atom; and two n's are independently 1 or 2.

[2] The polymer compound as described in [1] wherein the monomer represented by the formula (1) is represented by the following formula (1-i).

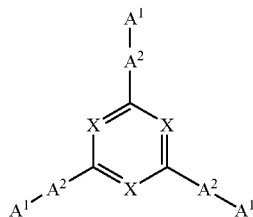

(1-i)

In the formula (1-i), each of three $A^1$'s is independently an aromatic group optionally having a heteroatom as a ring-constituting atom, hydrogen atom, a halogen atom, an amino group, an alkyl group having 1 to 20 carbon atoms, an alkoxy group having 1 to 12 carbon atoms or an aryloxy group having 6 to 10 carbon atoms;

at least one of three $A^1$'s is a condensed polycyclic aromatic group optionally having a heteroatom as a ring-constituting atom;

the condensed polycyclic aromatic group links to $A^2$ at the meta position to the bond position of the ring represented by the following formula;

each of three $A^2$'s is independently a six-membered ring aromatic group optionally having a heteroatom as a ring-constituting atom;

each of hydrogen atoms directly bonded to the ring-constituting atoms in $A^1$ and $A^2$ may be independently substituted by an aromatic group optionally having a heteroatom as a ring-constituting atom, a halogen atom, an amino group, an alkyl group having 1 to 12 carbon atoms, an alkoxy group having 1 to 12 carbon atoms or an aryloxy group having 6 to 10 carbon atoms;

at least one of $A^1$ and $A^2$ has a substituent having a polymerizing functional group; and each of three X's is independently a carbon atom to which one hydrogen atom is bonded or a nitrogen atom, and at least one of three X's is a nitrogen atom.

[3] The polymer compound as described in [2] wherein in the formula (1-i), one $A^1$ has a substituent having a polymerizable functional group and at least one of three $A^1$'s is a carbazolyl group optionally having a substituent having a polymerizable functional group, or a halogen atom, an amino group, an alkyl group having 1 to 12 carbon atoms, an alkoxy group having 1 to 12 carbon atoms, an aryloxy group having 6 to 10 carbon atoms or an aromatic group optionally having a heteroatom as a ring-constituting atom.

[4] The polymer compound as described in [2] or [3] wherein the monomer represented by the formula (1) is represented by the following formula (A1), (A13), (A14), (A15), (A31), (A35), (A40), (A42), (A60), (A71), (A73), (A78), (A79), (A80), (A88), A(89), (A107) or (A108).

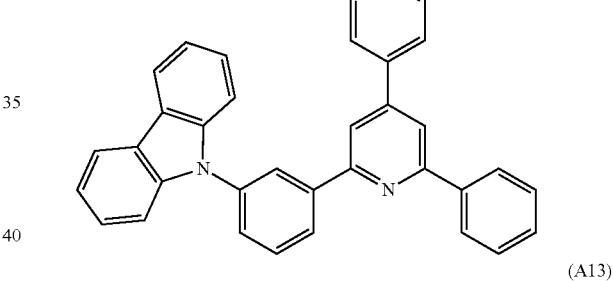

(A1)

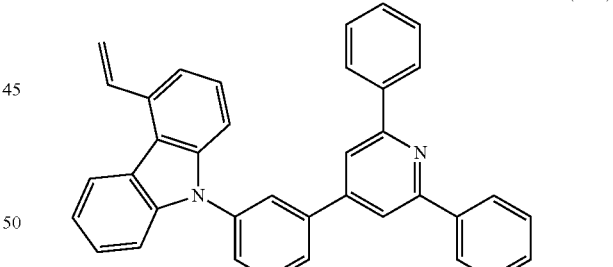

(A13)

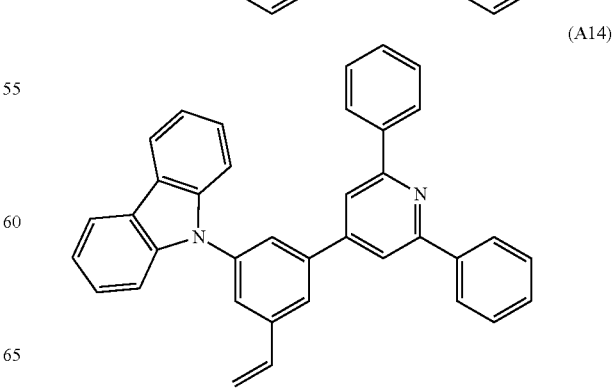

(A14)

(A15)
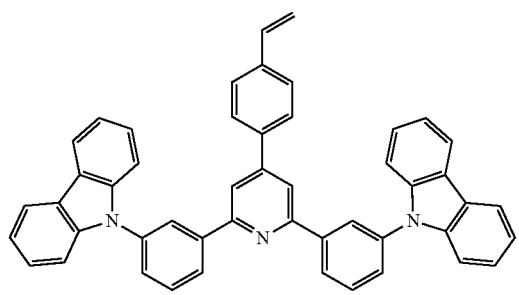
(A40)
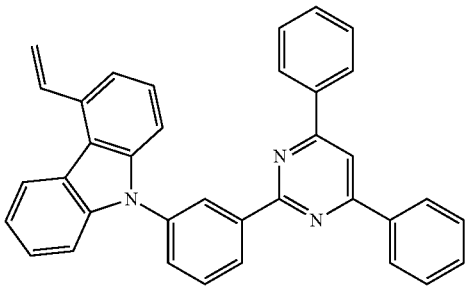
(A31)
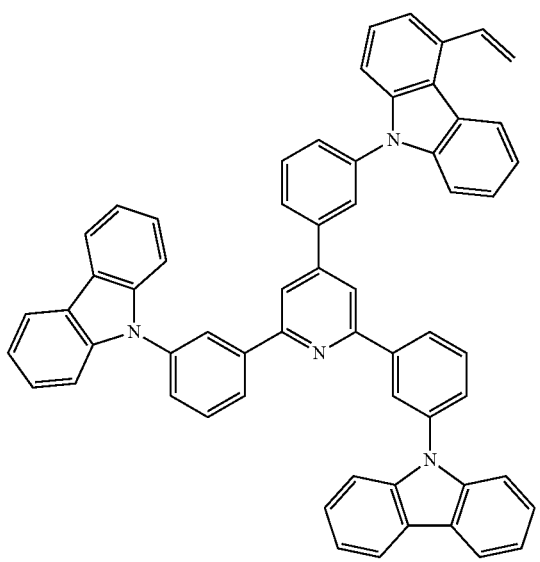
(A42)
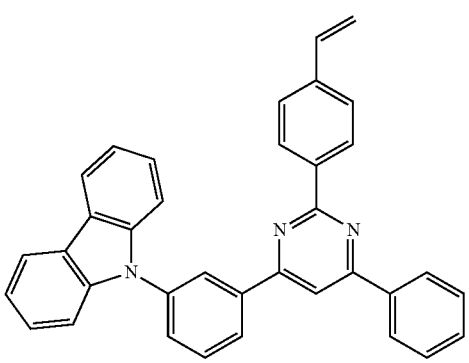
(A60)
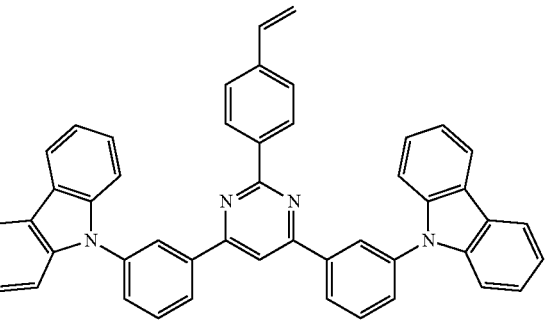
(A35)
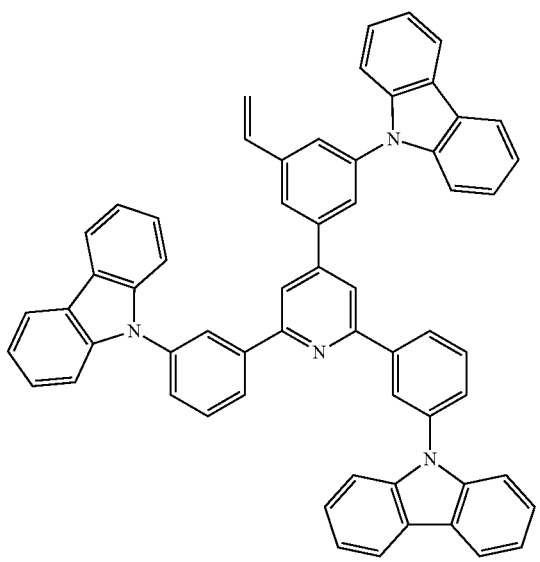
(A71)
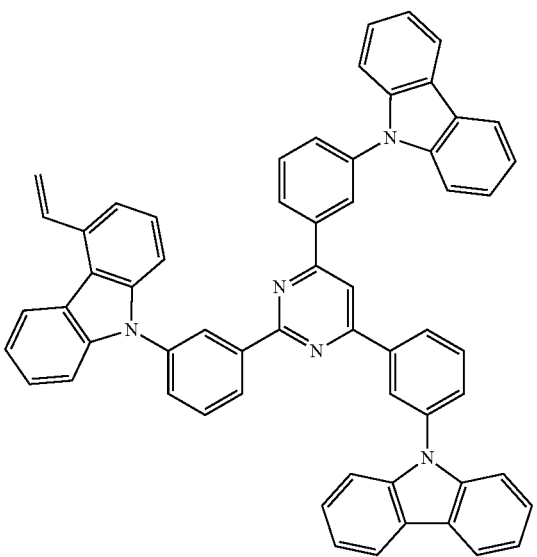

(A73)
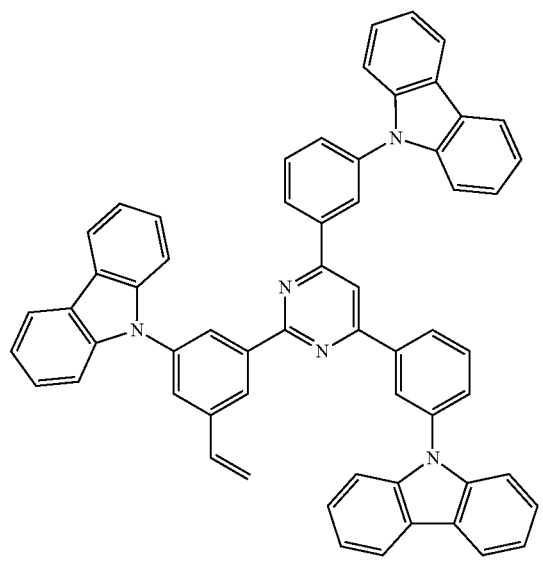
(A78)
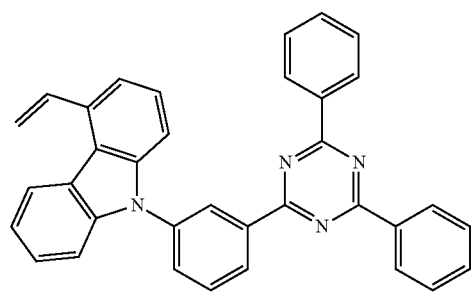
(A79)
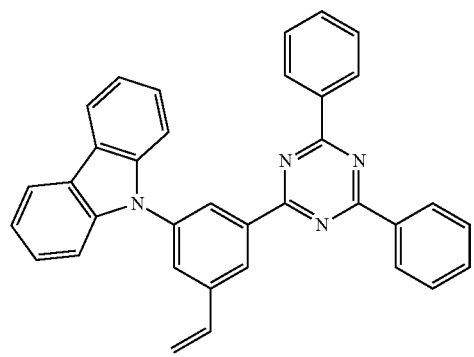
(A80)
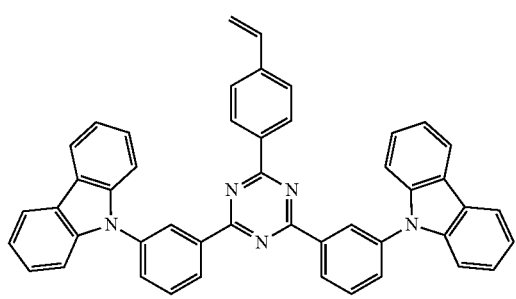
(A88)
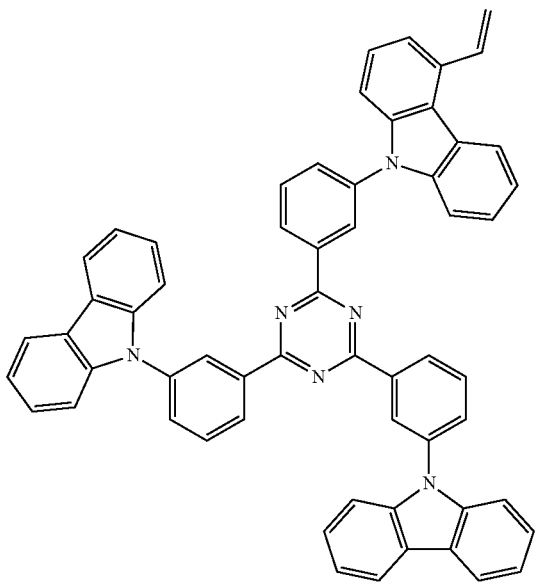
(A89)
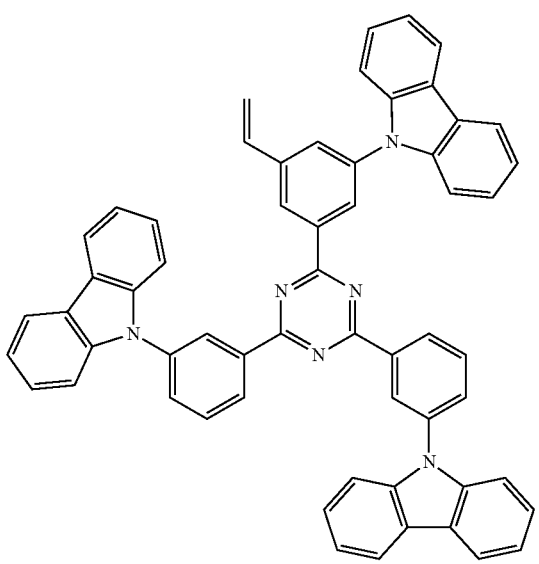
(A107)
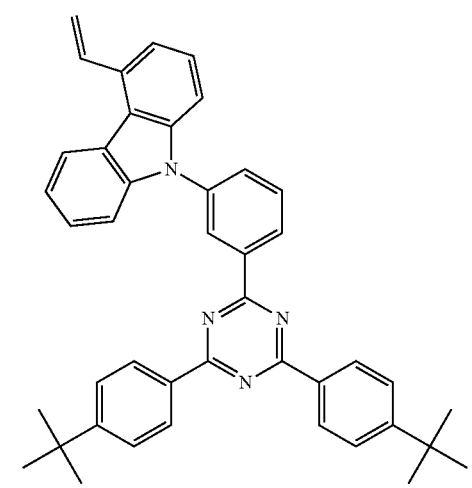

-continued

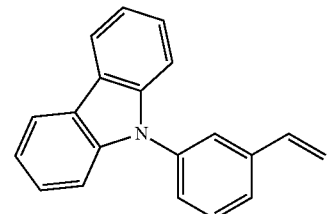
(A108)

[5] The polymer compound as described in [1] wherein the monomer represented by the formula (1) is represented by the following formula (1-ii).

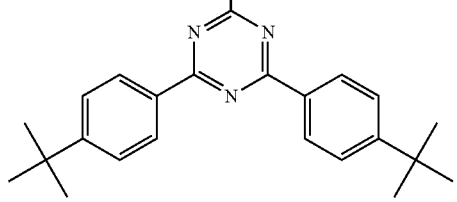
(1-ii)

In the formula (1-ii), $A^1$ is an aromatic group having a heteroatom as a ring-constituting atom, hydrogen, a halogen atom, an amino group, an alkyl group having 1 to 12 carbon atoms, an alkoxy group having 1 to 12 carbon atoms or an aryloxy group having 6 to 10 carbon atoms;

each of four $A^3$'s is independently a condensed polycyclic aromatic group optionally having a heteroatom as a ring-constituting atom;

$A^1$ links to $A^2$ and $A^3$ links to $A^4$ respectively at the meta position to the bonding position of the ring represented by the following formula;

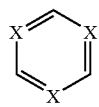

$A^2$ and two $A^4$'s are independently a six-membered ring aromatic group optionally having a heteroatom as a ring-constituting atom respectively;

in each of $A^1$ to $A^4$, a hydrogen atom directly bonded to the ring-constituting atom may be independently substituted with an aromatic group optionally having a heteroatom as a ring-constituting atom, a halogen atom, an amino group, an alkyl group having 1 to 12 carbon atoms, an alkoxy group having 1 to 12 carbon atoms or an aryloxy group having 6 to 10 carbon atoms;

at least one of $A^1$ to $A^4$ has a substituent having a polymerizable functional group; and each of three X's is a carbon atom bonded with one hydrogen atom or a nitrogen atom, and at least one of three X's is a nitrogen atom.

[6] The polymer compound as described in [5] wherein in the formula (1-ii), one $A^1$ has a substituent having a polymerizable functional group, at least one of four $A^3$'s is a carbazolyl group optionally having a substituent having a polymerizable functional group or a halogen atom, an amino group, an alkyl group having 1 to 12 carbon atoms, an alkoxy group having 1 to 12 carbon atoms, an aryloxy group having 6 to 10 carbon atoms or an aromatic group optionally having a heteroatom as a ring-constituting atom.

[7] The polymer compound as described in [5] or [6] wherein the monomer represented by the formula (1-ii) is represented by the following formula (A92), (A94), (A96), (A100), (A102) or (A104).

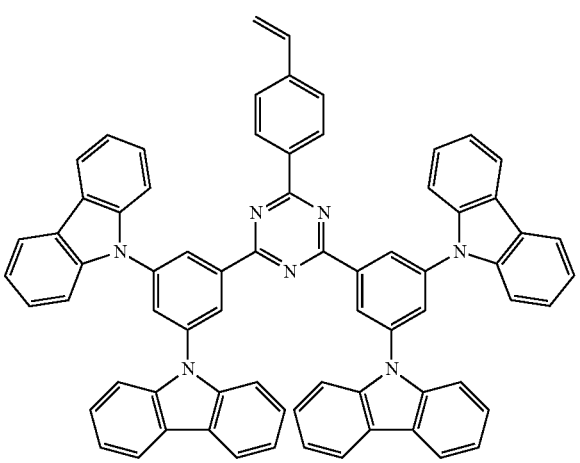
(A92)

(A94)

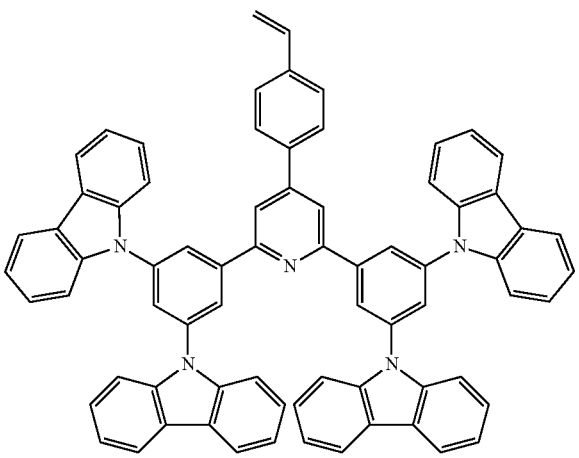

(A96)

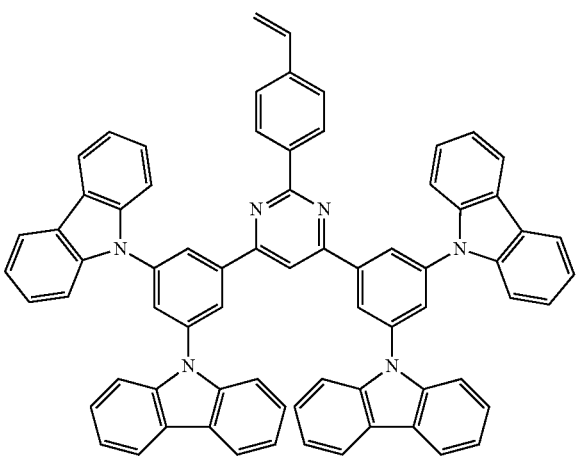

-continued

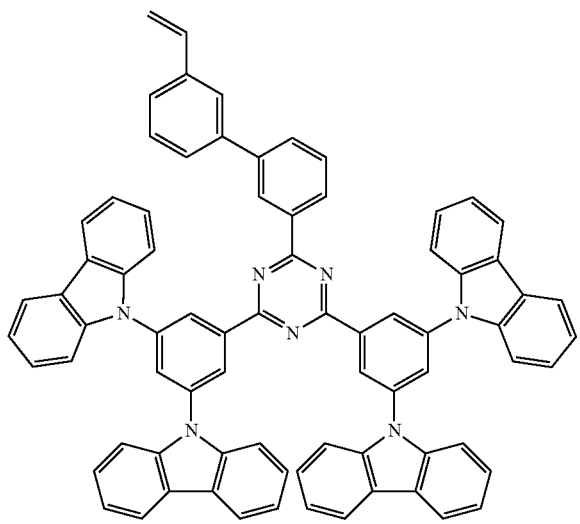
(A100)

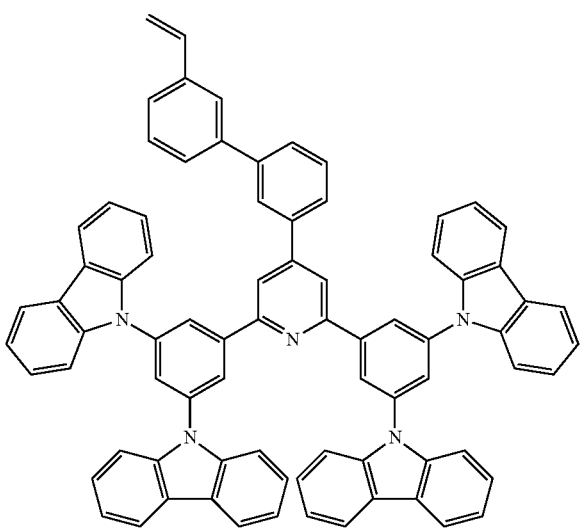
(A102)

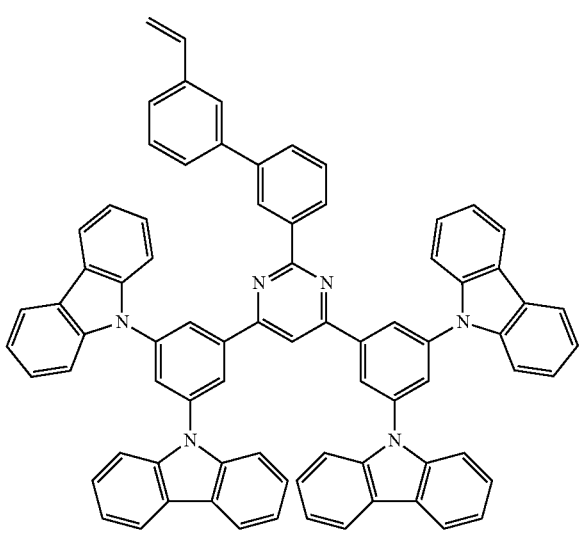
(A104)

[8] The polymer compound as described in any one of [1] to [7], which further comprises a constituting unit derived from a polymerizable compound having hole-transporting properties.

[9] The polymer compound as described in [8], wherein the polymerizable compound having hole-transporting properties has a carbazole structure or a triphenylamine structure.

[10] The polymer compound as described in [9], wherein the polymerizable compound having hole-transporting properties has a carbazole structure.

[11] The polymer compound as described in any one of [1] to [10], which further comprises at least one of a constituting unit derived from a polymerizable compound having electron-transporting properties and a constituting unit derived from a polymerizable compound having luminous properties.

[12] The polymer compound as described in [11], wherein the polymerizable compound having luminous properties has phosphorescent properties.

[13] The polymer compound as described in [11] or [12], wherein the polymerizable compound having luminous properties is a transition metal complex.

[14] The polymer compound as described in [13], wherein the transition metal complex is an iridium complex.

[15] The polymer compound as described in any one of [11] to [14], wherein the polymerizable compound having electron-transporting properties has an aromatic heterocyclic substituent or a triarylboron substituent.

[16] The polymer compound as described in any one of [1] to [15], which is used for organic electroluminescence elements.

[17] The luminous layer for organic electroluminescence elements according to the present invention comprises the polymer compound as described in any one of [1] to [16].

[18] The organic electroluminescence element according to the present invention comprises at least one organic layer provided between an anode and a cathode, wherein at least one luminous layer contained in the organic layer, comprises the polymer compound as described in any one of [1] to [16].

[19] The article equipped with the organic electroluminescence element as described in [18] according to the present invention is selected from displays, back lights, electro-photographs, light sources for illumination, light sources for recording, light sources for exposure, light sources for reading, markers, signboards, interior goods and optical communication systems.

[20] The process for producing an organic electroluminescence element according to the present invention comprises a step of forming the organic layer comprising at least one luminous layer as described in [17] on an anode, and a step of forming a cathode on the organic layer.

In the present invention, the direction from an anode toward an organic layer is referred to "upper direction" expediently.

Effect of the Invention

The polymer compound according to the present invention provides an organic EL element having a low driving voltage and high durability.

BRIEF DESCRIPTION OF THE DRAWING

FIG. 1 is a section showing an embodiment of the organic EL element according to the present invention.

DESCRIPTION OF MARKS

1: glass substrate
2: anode
3: hole-transporting layer

4: luminous layer
5: electron-transporting layer
6: cathode

BEST EMBODIMENT FOR CARRYING OUT
THE INVENTION

The present invention will be described in detail hereinafter.

Embodiment 1

The polymer compound (I) of the present invention (Embodiment 1) comprises a constituting unit derived from a polymerizable compound having carrier-transporting properties represented by the formula (1), preferably the formula (1-i) or (1-ii) and is obtainable by polymerizing the polymerizable compound having carrier-transporting properties represented by the formula (1), preferably the formula (1-i) or (1-ii). Since using the polymer compound (I), electrons and holes are transported together, the driving voltage is lowered and thereby an organic EL element having high durability can be prepared.

In the formula (1), each of $A^1$'s is independently an aromatic group optionally having a heteroatom as a ring-constituting atom, hydrogen atom, a halogen atom, an amino group, an alkyl group having 1 to 12 carbon atoms, an alkoxy group having 1 to 12 carbon atoms or an aryloxy group having 6 to 10 carbon atoms.

Examples of the aromatic group are a condensed polycyclic aromatic group optionally having a heteroatom as a ring-constituting atom, a phenyl group, a pyridyl group and a pyrimidyl group. Of these, as a substituent other than the condensed polycyclic aromatic group optionally having a heteroatom as a ring-constituting atom, the phenyl group is preferable.

Examples of the halogen atom are fluorine atom, chlorine atom, bromine atom and iodine atom. Of these, preferable examples are fluorine atom and chlorine atom, and a more preferable example is fluorine atom.

Examples of an alkyl group having 1 to 12 carbon atoms are methyl group, ethyl group, propyl group, isopropyl group, butyl group, isobutyl group, t-butyl group, amyl group, hexyl group, octyl group, decyl group, 2-ethylhexyl group, and dodecyl group. Of these, preferable examples are alkyl groups having 2 to 8 carbon atoms, and more preferable examples are alkyl groups having 3 to 6 carbon atoms.

Examples of an alkoxy group having 1 to 12 carbon atoms are methoxy group, ethoxy group, propoxy group, isopropoxy group, butoxy group, isobutoxy group, t-butoxy group, hexyloxy group, 2-ethylhexyl oxy group, decyloxy group and dodecyloxy group. Of these, preferable examples are alkoxy groups having 2 to 8 carbon atoms, and more preferable examples are alkoxy groups having 3 to 6 carbon atoms.

Examples of an aryloxy group having 6 to 10 carbon atoms are phenoxy group, benzyloxy group, phenetyloxy group, phenylpropoxy group and phenyl butoxy group. Of these, preferable examples are phenoxy group, benzyloxy group and phenetyloxy group, and a more preferable example is phenoxy group.

In the formula (1), at least one of $A^1$'s is a condensed polycyclic aromatic group optionally having a heteroatom as a ring-constituting atom.

Examples of the condensed polycyclic aromatic compound are naphthyl group, antracenyl group, phenanthrenyl group, pyrenyl group, tetracenyl group, pentacenyl group, fluorenyl group, triphenylenyl group, perylenyl group, indolyl group, carbazolyl group, benzoxazolyl group, benzothiazolyl group, benzothiophenyl group, dibenzofuranyl group, dibenzothiophenyl group, azaindolyl group, quinolinyl group, pyridoindolyl group, benzothiadiazolyl group. Of these, preferable examples are carbazolyl group, indolyl group, azaindolyl group and pyridoindolyl group, more preferable examples are carbazolyl group and indolyl group and a particularly preferable example is carbazolyl group.

In the formula (1), each of three $A^2$'s is independently an aromatic group optionally having a heteroatom as a ring-constituting atom.

Examples of the aromatic group are phenylene group, pyridine group and pyrimidylene group. Of these, phenylene group is preferred.

In the formula (1), each of hydrogen atoms directly bonded to the ring-constituting atom in $A^1$ and $A^2$ may be independently substituted by an aromatic group optionally having a heteroatom as a ring-constituting atom, a halogen atom, an amino group, an alkyl group having 1 to 12 carbon atoms, an alkoxy group having 1 to 12 carbon atoms or an aryloxy group having 6 to 10 carbon atoms.

Examples of the aromatic group are phenyl group, pyridyl group and pyrimidyl group. Of these, preferable examples are phenyl group and pyridyl group, and a more preferable example is phenyl group.

Examples of the halogen atom are fluorine atom, chlorine atom, bromine atom and iodine atom. Of these, preferable examples are fluorine atom and chlorine atom, and a more preferable example is fluorine atom.

Examples of an alkyl group having 1 to 12 carbon atoms are methyl group, ethyl group, propyl group, isopropyl group, butyl group, isobutyl group, t-butyl group, amyl group, hexyl group, octyl group, decyl group, 2-ethylhexyl group, and dodecyl group. Of these, preferable examples are alkyl groups having 2 to 8 carbon atoms, and more preferable examples are alkyl groups having 3 to 6 carbon atoms.

Examples of an alkoxy group having 1 to 12 carbon atoms are methoxy group, ethoxy group, propoxy group, isopropoxy group, butoxy group, isobutoxy group, t-butoxy group, hexyloxy group, 2-ethylhexyl oxy group, decyloxy group and dodecyloxy group. Of these, preferable examples are alkoxy groups having 2 to 8 carbon atoms, and more preferable examples are alkoxy groups having 3 to 6 carbon atoms.

Examples of an aryloxy group having 6 to 10 carbon atoms are phenoxy group, benzyloxy group, phenetyloxy group, phenylpropoxy group and phenyl butoxy group. Of these, preferable examples are phenoxy group, benzyloxy group and phenetyloxy group, and a more preferable example is phenoxy group.

In the formula (1), at least one of $A^1$'s is a condensed polycyclic aromatic group optionally having a heteroatom as a ring-constituting atom. All of the $A^1$'s, which are the condensed polycyclic aromatic groups and the aromatic groups, each link to $A^2$ at the meta position to the bonding position of the ring represented by the following formula (namely, pyridine ring, pyrimidine ring or triadine ring).

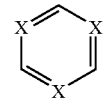

For example, when $A^2$ represents a six-membered ring aromatic group having only a carbon atom as a ring-constituting atom, the bonding position is represented by the following formula (i) or (ii). The monomer represented by the formula (1) is preferred because of having excellent resistance to electric oxidation and being capable of hardly forming an excimer.

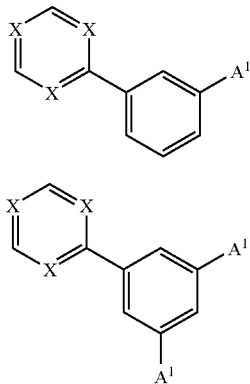

In the formula (1), at least of $A^1$ and $A^2$ has a substituent having a polymerizable functional group. Of these, at least of $A^1$ preferably has a substituent having a polymerizable functional group because organic EL elements having higher luminous efficiency can be prepared. The above substituents having a polymerizable functional group include the polymerizable functional group itself.

The polymerizable functional group may be any one of radical polymerizable, cation polymerizable, anion polymerizable, addition polymerizable and condensation polymerizable functional groups. Of these, the radical polymerizable functional group is preferred because the polymer production is easy.

Examples of the polymerizable functional group may include allyl groups; alkenyl groups; acrylate groups; methacrylate groups; urethane (meth)acrylate groups such as methacryloxy ethyl carbamate etc; vinyl amide groups; and derivatives thereof.

Preferable examples of the substituent having a polymerizable functional group are substituents represented by the following formula (7).

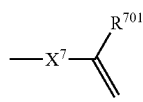

In the formula (7), $R^{701}$ is hydrogen or an alkyl group having 1 to 12 carbon atoms.

Examples of the alkyl group having 1 to 12 carbon atoms may include methyl group, ethyl group, propyl group, isopropyl group, butyl group, isobutyl group, t-butyl group, amyl group, hexyl group, octyl group, decyl group, 2-ethylhexyl group and dodecyl group. Of these, $R^{701}$ is preferably hydrogen because of having excellent carrier-transporting properties.

$X^7$ is a single bond or a group represented by any one of the formulas (X71) to (X74).

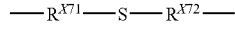

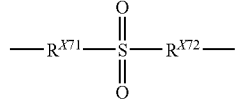

In the formulas, $R^{X71}$ is a single bond or an alkylene group having 1 to 12 carbon atoms, and $R^{X72}$ is a single bond, an alkylene group having 1 to 12 carbon atoms or a phenylene group. In the formula (1), it is preferred that $R^{x71}$ bonds to $A^1$ and $R^{X72}$ bonds to a vinyl group. Using such $X^7$, it is possible to prepare organic EL elements having a low driving voltage and high durability.

Examples of the alkylene group having 1 to 12 carbon atoms may include methylene group, ethylene group, propylene group, isopropylene group, butylenes group, isobutylene group, t-butylene group, amylene group, hexylene group, octylene group, decylene group, 2-ethylhexylene group, and dodecylene group. Of these, alkylene groups having 1 to 6 carbon atoms are preferred and alkylene groups having 1 to 3 carbon atoms are more preferred.

Of these, $X^7$ is preferably a single bond or an alkylene group having 1 to 7 carbon atoms, more preferably a single bond.

In the formula (1), one $A^1$ has a substituent having a polymerizable functional group represented by the formula (7), and at least one of plural A1's is preferably a halogen atom, an amino group, an alkyl group having 1 to 12 carbon atoms, an alkoxy group having 1 to 12 carbon atoms, an aryloxy groups having 6 to 10 carbon atoms, an aromatic group optionally having a heteroatom as a ring-constituting atom or a carbazolyl group having a substituent with a polymerizable functional group.

Examples of the halogen atom and the above substituent such as an alkyl group or the like are the same as described above.

Since the monomer represented by the formula (1) has excellent solubility and carrier-transporting ability, particularly preferable examples are a monomer in which one $A^1$ in the formula (1) is a carbazolyl group substituted with a polymerizable functional group represented by the above formula (7) and $A^2$ bonded to $A^1$ which represents the carbazolyl group is represented by the formula (i) or (ii), and a monomer in which one $A^1$ has a polymerizable functional group represented by the formula (7) and at least one $A^1$ of residual $A^1$'s is a carbazolyl group.

In the formula (1), three X's represent a carbon atom bonded with one hydrogen atom or a nitrogen atom, and at least one of the three X's represents a nitrogen atom. That is to say, the monomer represented by the formula (1) has any one of a pyridine ring skeleton, a pyrimidine ring skeleton and a triadine ring skeleton.

As the monomer represented by the formula (1), a monomer that two n's are 1 respectively (namely, a monomer represented by the formula (1-i)) and a monomer that two n's are 2 respectively (namely a monomer represented by the formula (1-ii)) are preferred because of having excellent resistance to electric and chemical oxidation and capable of hardly forming an excimer.

In the formula (1-ii), $A^3$ is independently a condensed polycyclic aromatic group optionally having a heteroatom as a ring-constituting atom, and examples of the condensed polycyclic aromatic group are the same as those of $A^1$ in the formula (1).

In the formula (1-ii), $A^4$ is independently a six-membered ring aromatic group optionally having a heteroatom as a ring-constituting atom, and examples of the aromatic group are the same as those of $A^2$ in the formula (1).

In $A^1$ to $A^4$ of the formula (1-ii), the hydrogen atoms directly bonded to the ring-constituting atom each may be independently substituted by an aromatic group optionally having a hetero atom as a ring-constituting atom, a halogen atom, an amino group, an alkyl group having 1 to 12 carbon atoms, an alkoxy group having 1 to 12 carbon atoms or an aryloxy group having 6 to 10 carbon atoms. These substituents are the same as those of $A^1$ and $A^2$ in the formula (1).

In the formula (1-ii), at least one of $A^1$ to $A^4$ has a substituent having a polymerizable functional group. Of these, at least one of $A^1$'s preferably has a substituent having a polymerizable functional group because organic EL elements having higher luminous efficiency can be prepared. The substituents having a polymerizable functional group include the polymerizable functional group itself.

Such a polymerizable functional group and the substituent having a functional group are the same as above.

Examples of the monomer represented by the formula (1-i) may include monomers represented by the following formulas (A1) to (A90), (A107) and (A108). Examples of the monomer represented by the formula (1-ii) may include monomers represented by the following formulas (A91) to (A106). The monomer of the present invention is not limited by the above.

(A1)

(A2)

(A3)

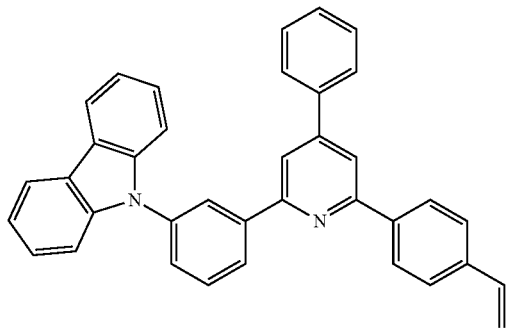

(A4)

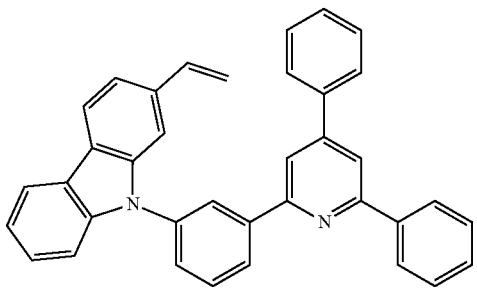

(A5)

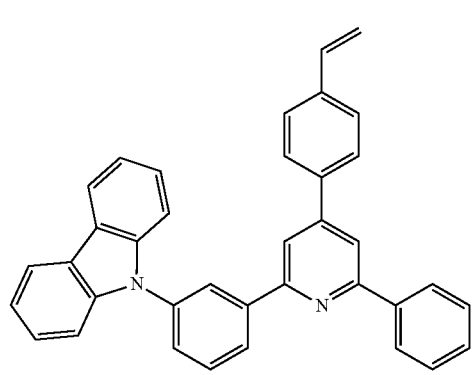

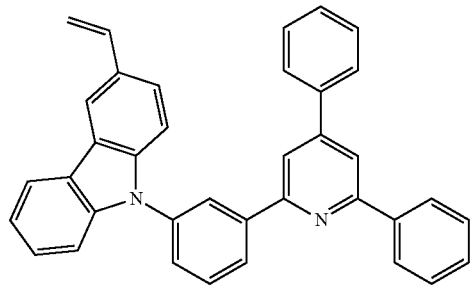

(A6)

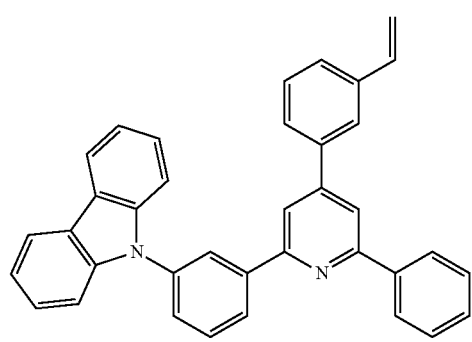

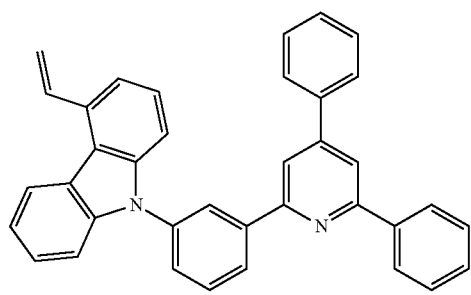

(A7)

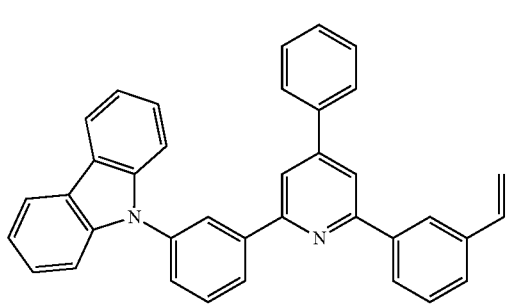

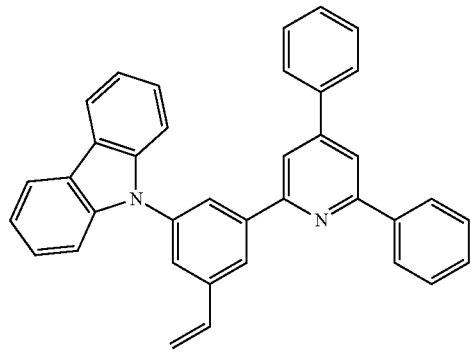

(A8)

(A9)
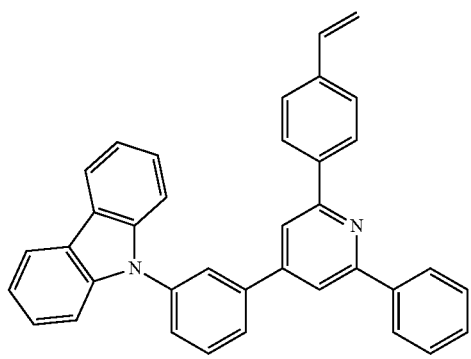
(A10)
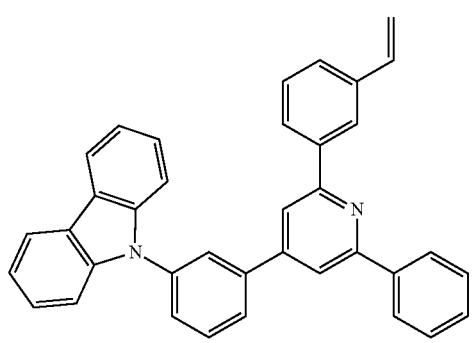
(A11)
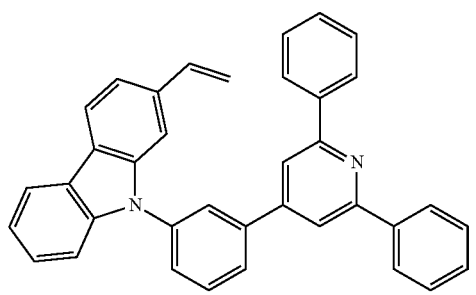
(A12)
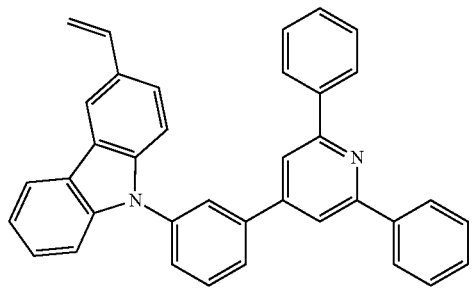
(A13)
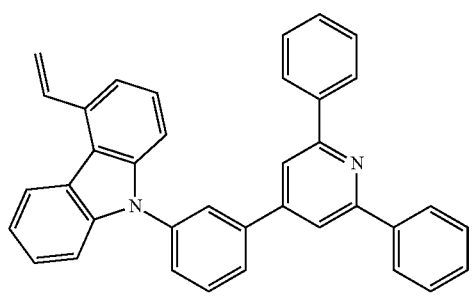
(A14)
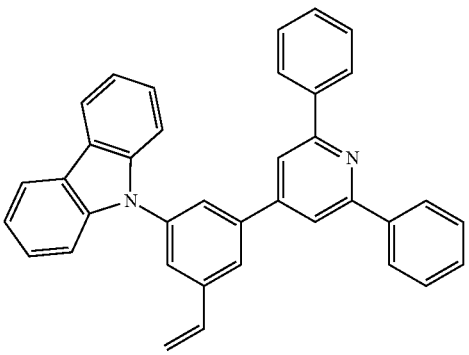
(A15)
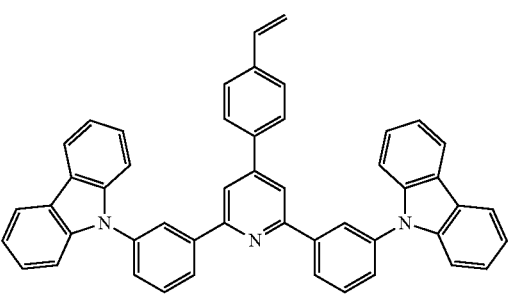
(A16)
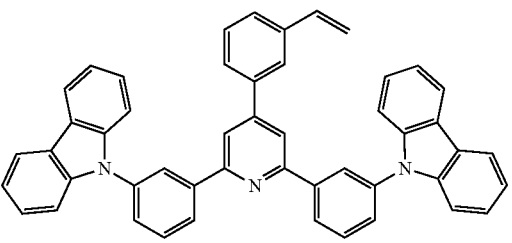
(A17)
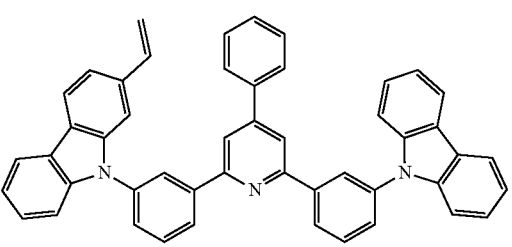
(A18)
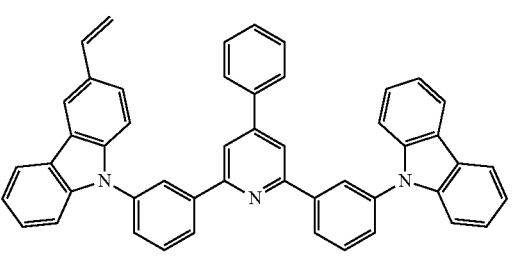

-continued
(A19)
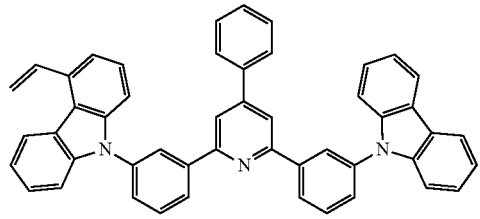
(A20)
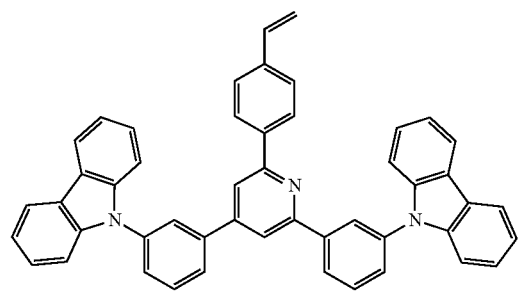
(A21)
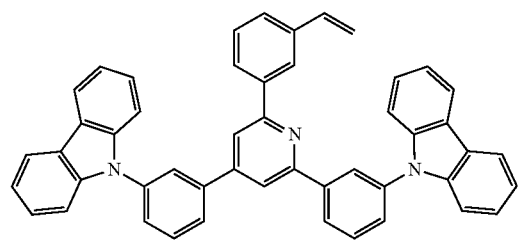
(A22)
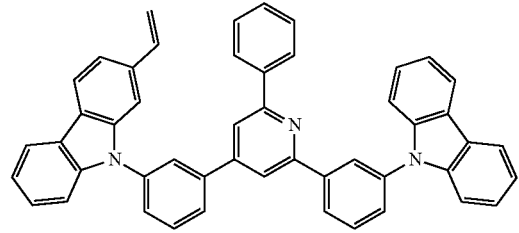
(A23)
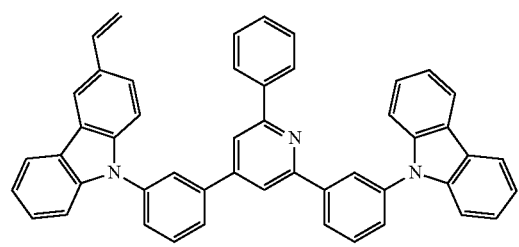
(A24)
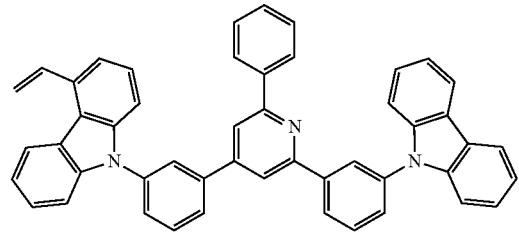
-continued
(A25)
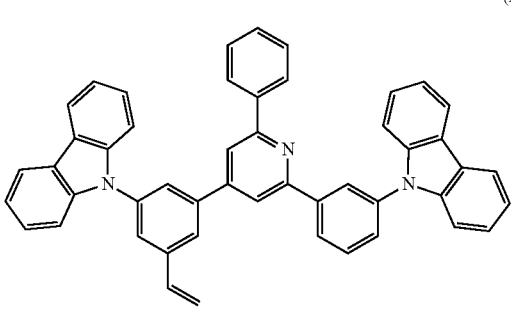
(A26)
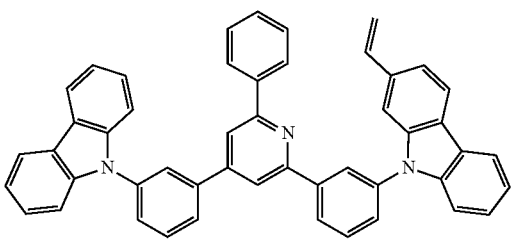
(A27)
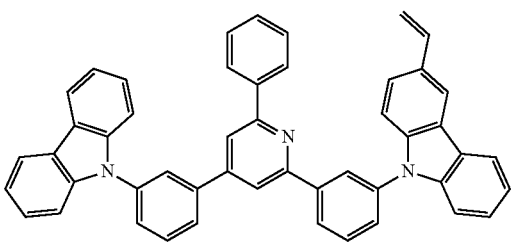
(A28)
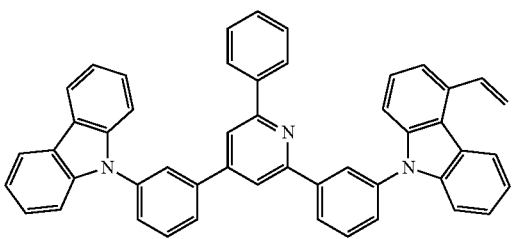
(A29)
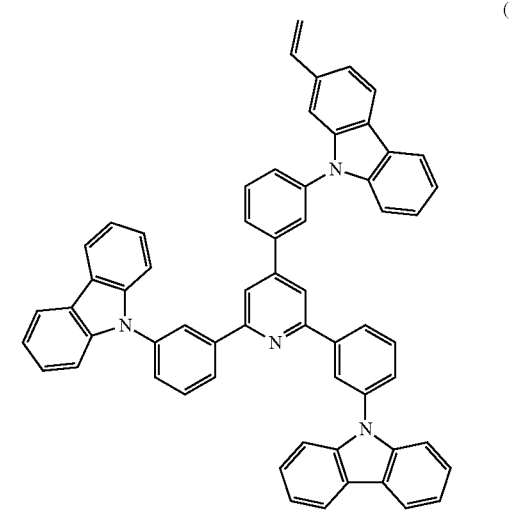

(A30)
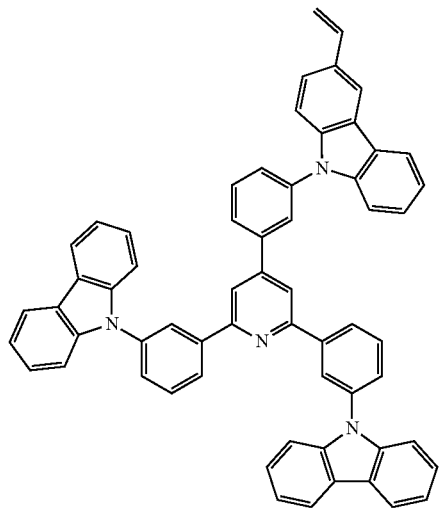
(A31)
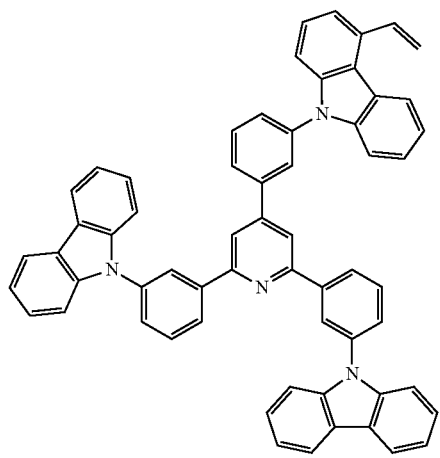
(A32)
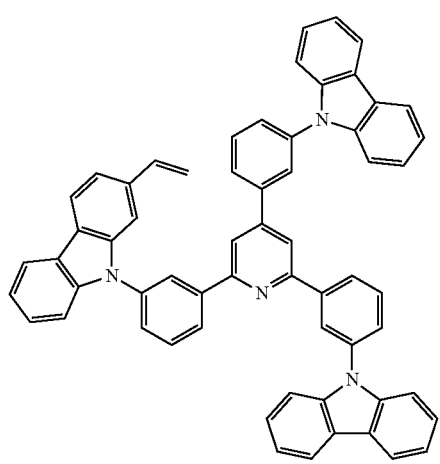
(A33)
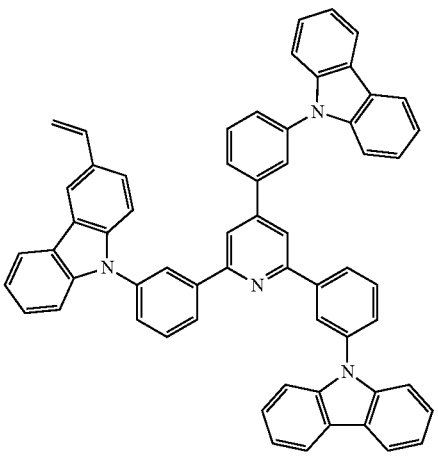
(A34)
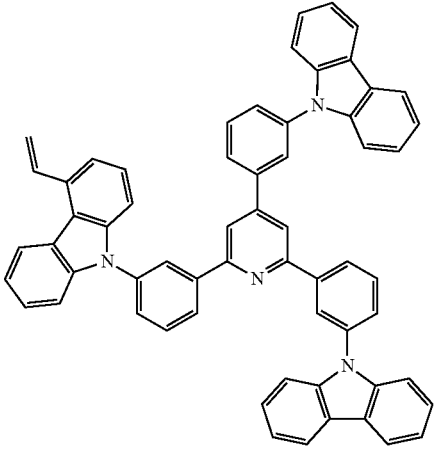
(A35)
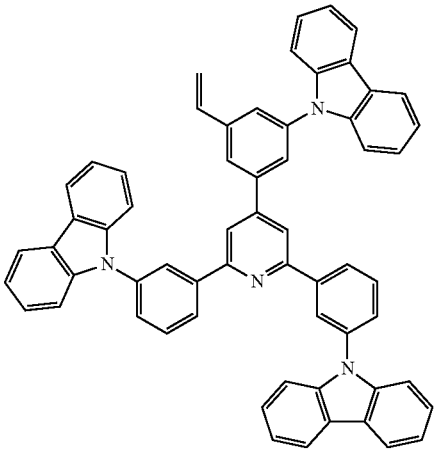
(A36)
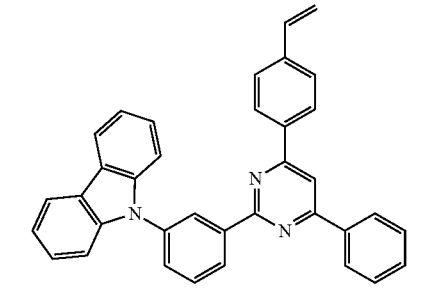

(A37)
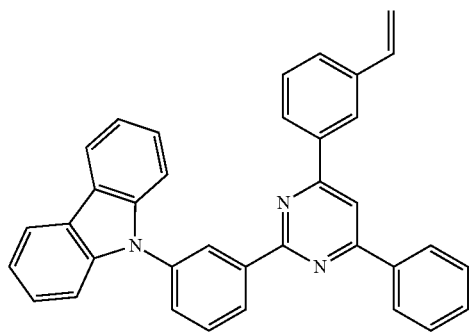
(A38)
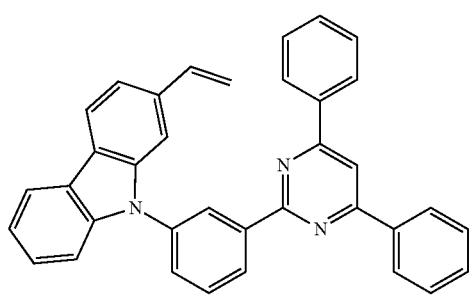
(A39)
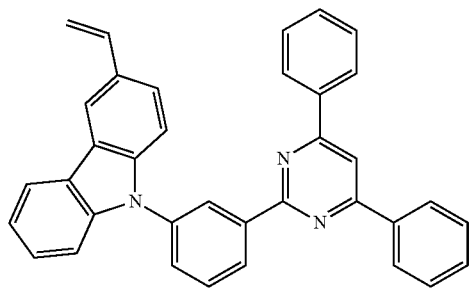
(A40)
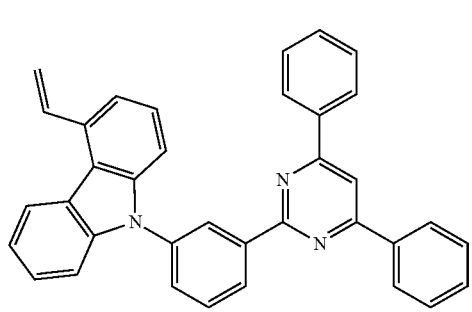
(A41)
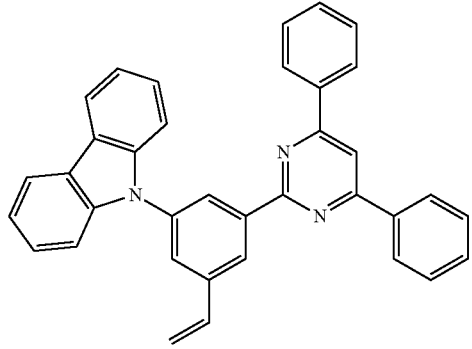
(A42)
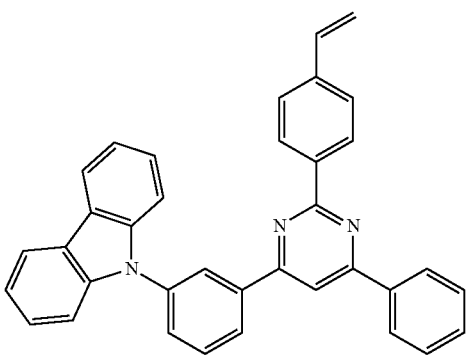
(A43)
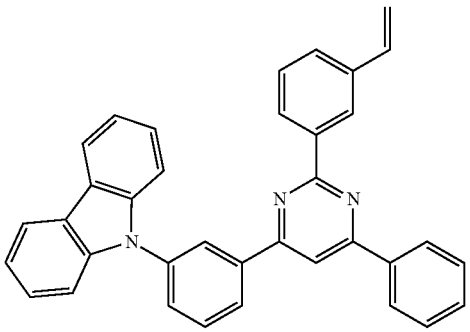
(A44)
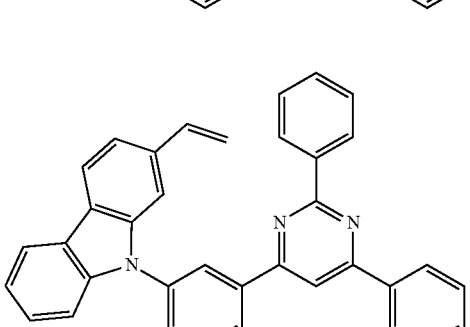
(A45)
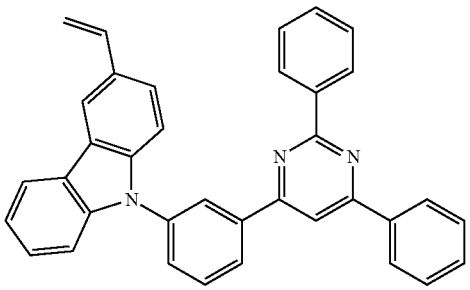
(A46)
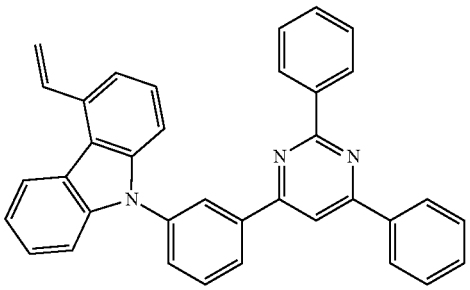

(A47)
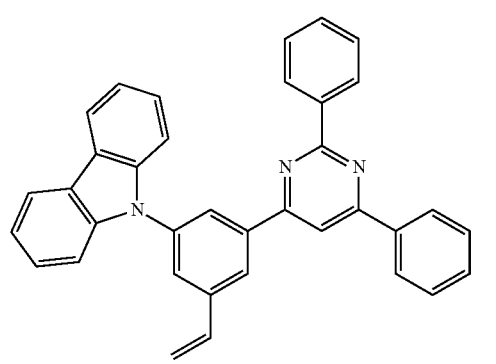
(A48)
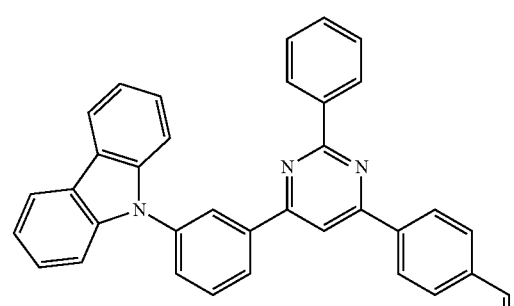
(A49)
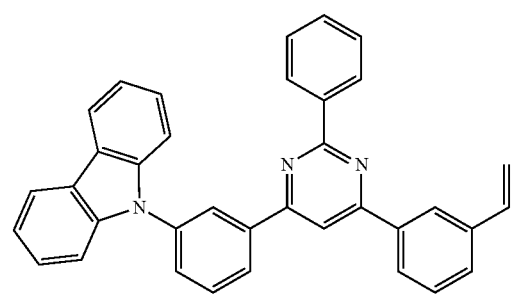
(A50)
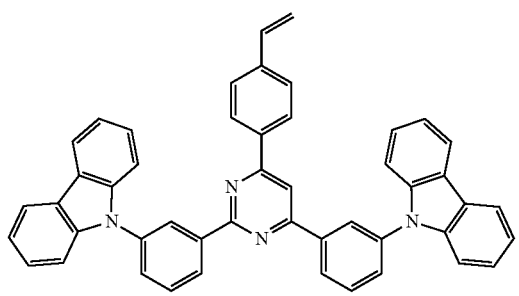
(A51)
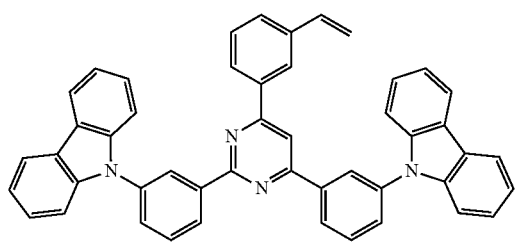
(A52)
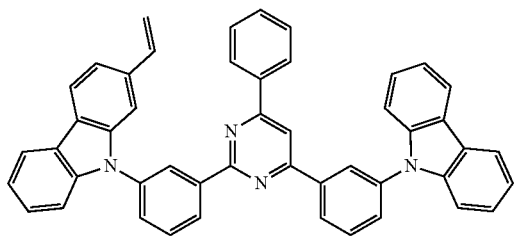
(A53)
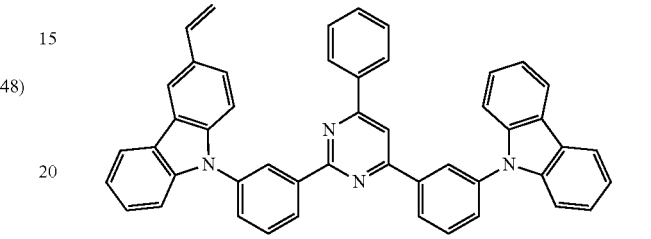
(A54)
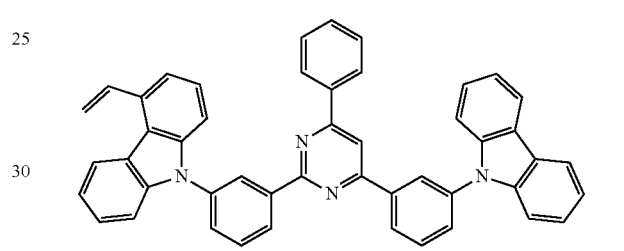
(A55)
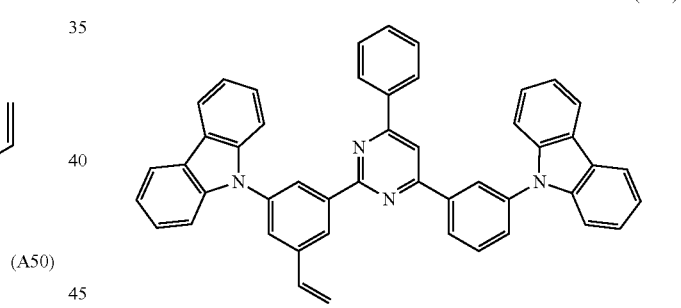
(A56)
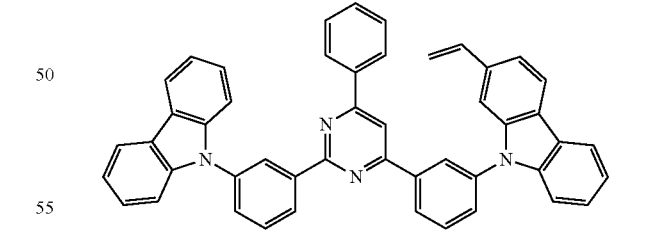
(A57)
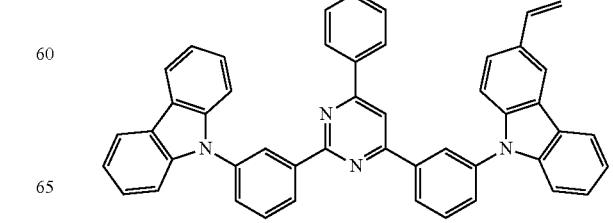

(A58)
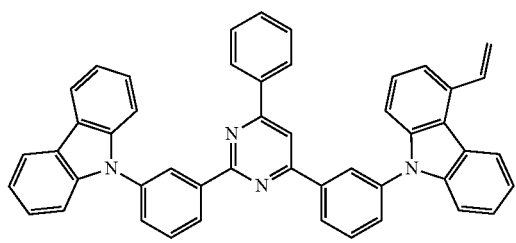
(A59)
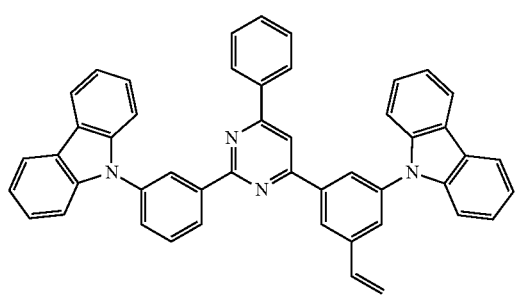
(A60)
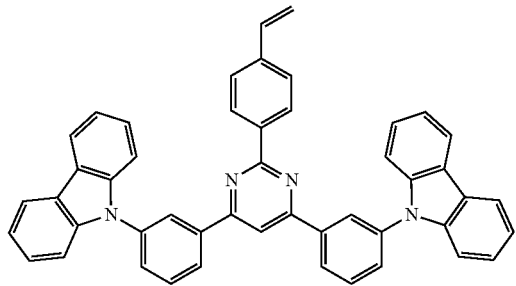
(A61)
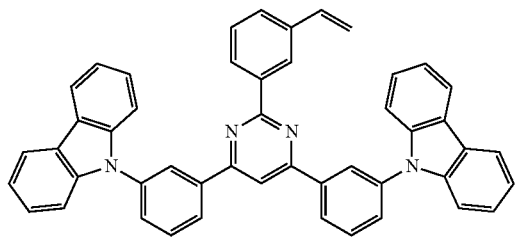
(A62)
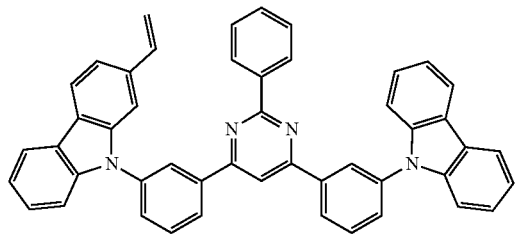
(A63)
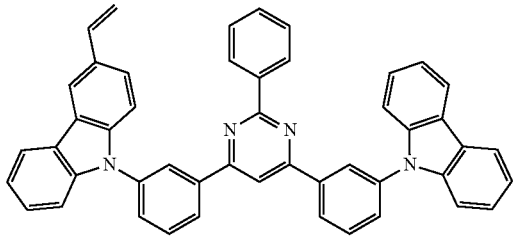
(A64)
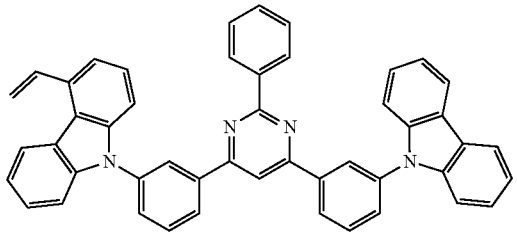
(A65)
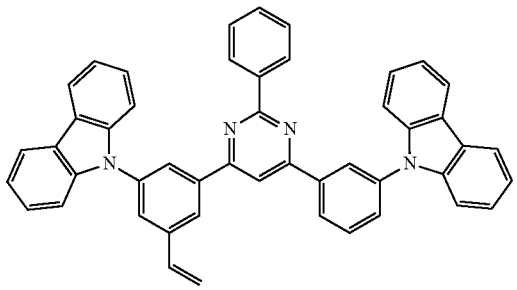
(A66)
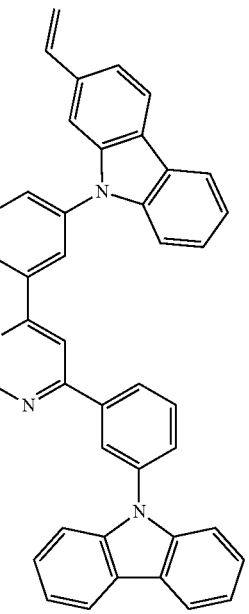

(A67)
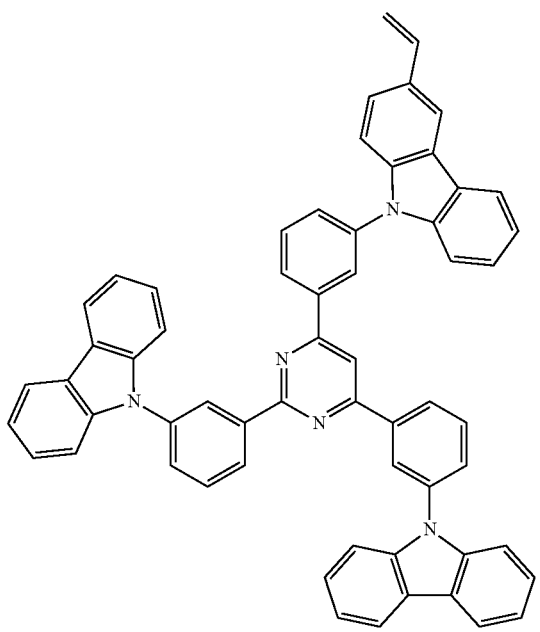
(A69)
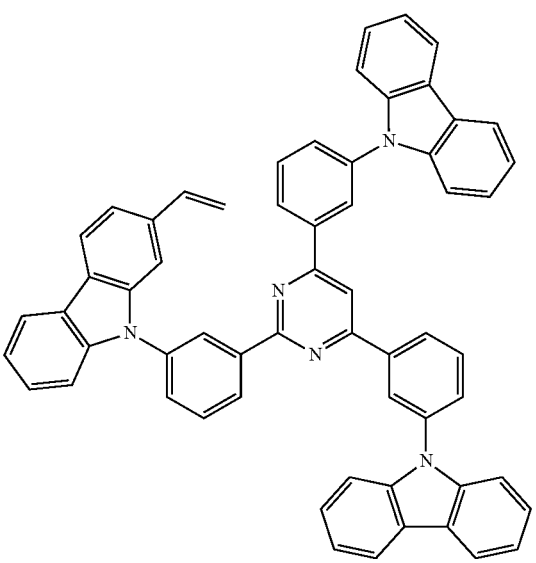
(A68)
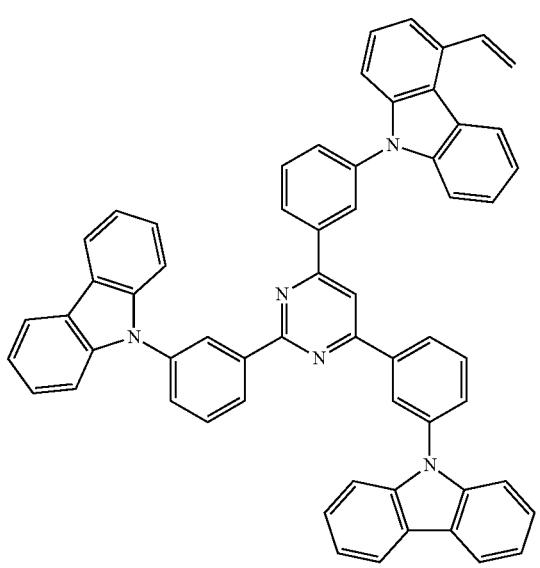
(A70)
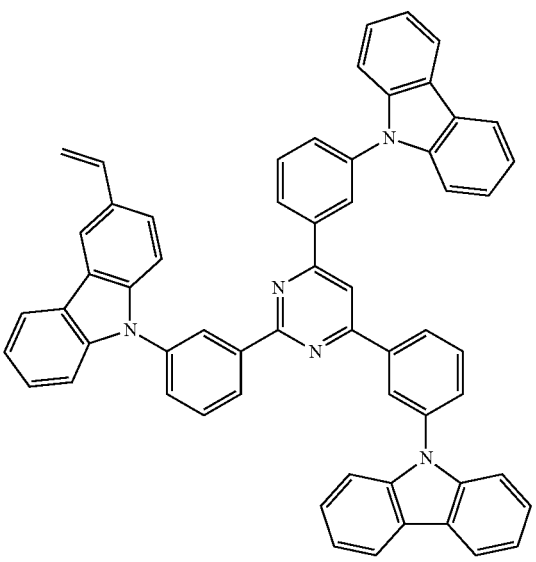

(A71)
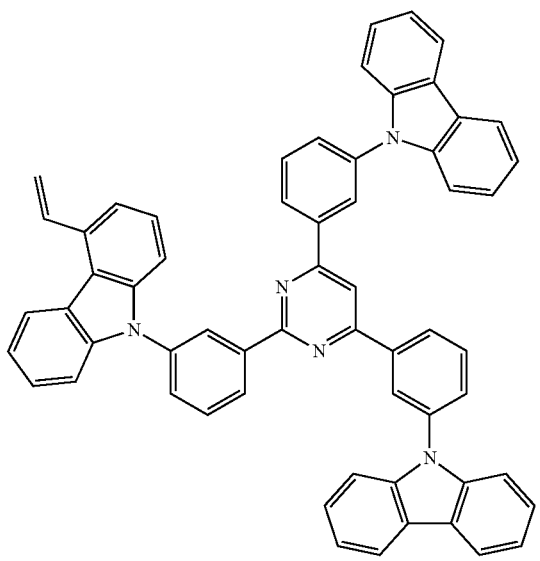
(A73)
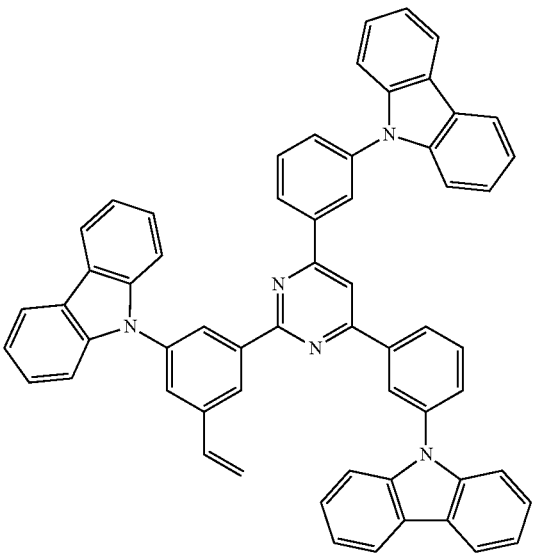
(A74)
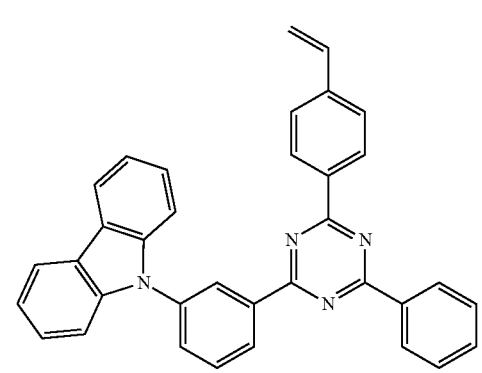
(A75)
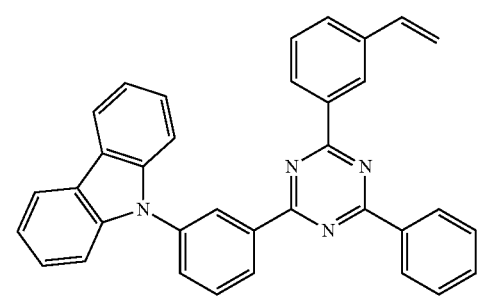
(A72)
(A76)
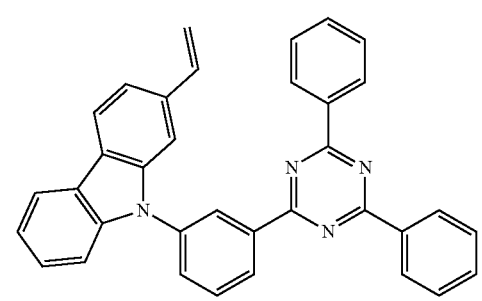

(A77)
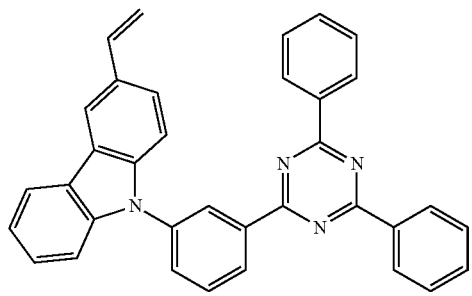
(A78)
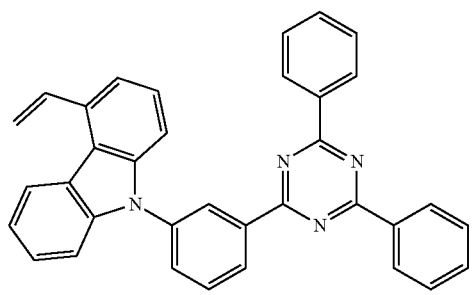
(A79)
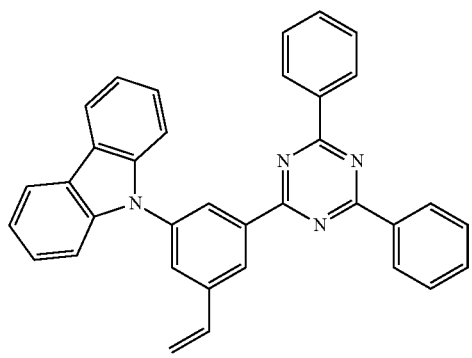
(A80)
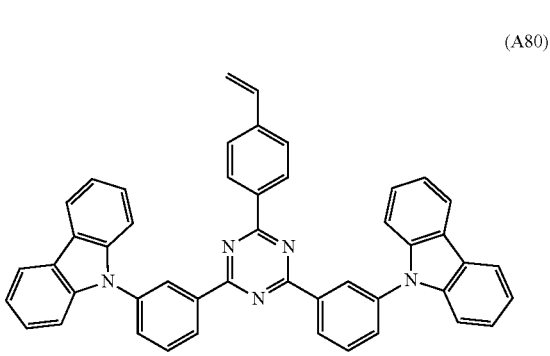
(A81)
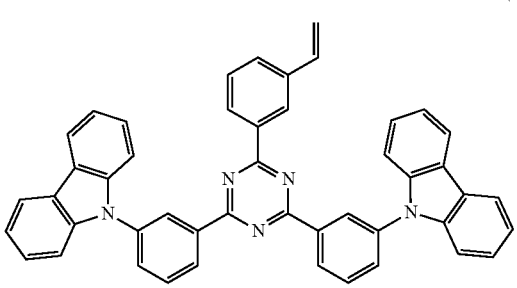
(A82)
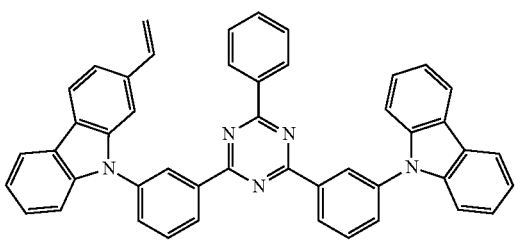
(A83)
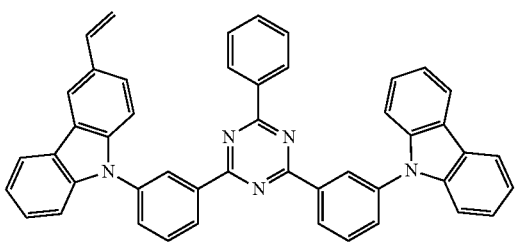
(A84)
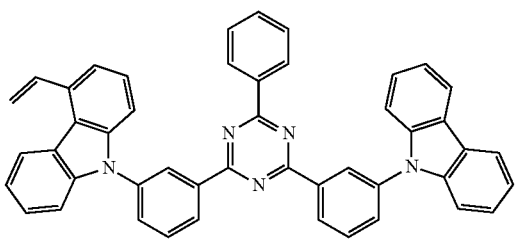
(A85)
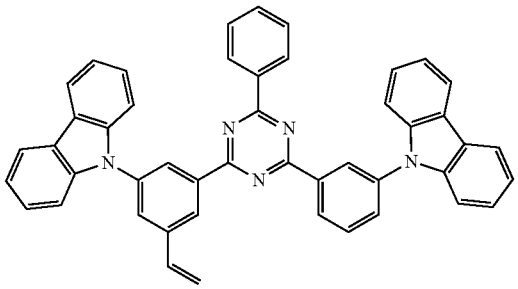

(A86)
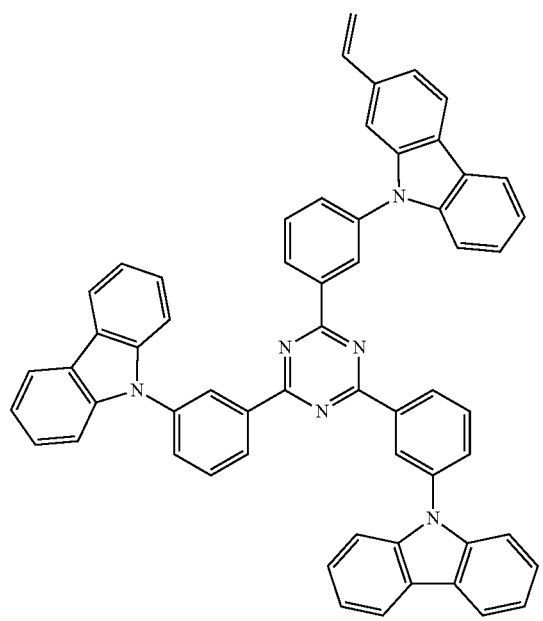
(A87)
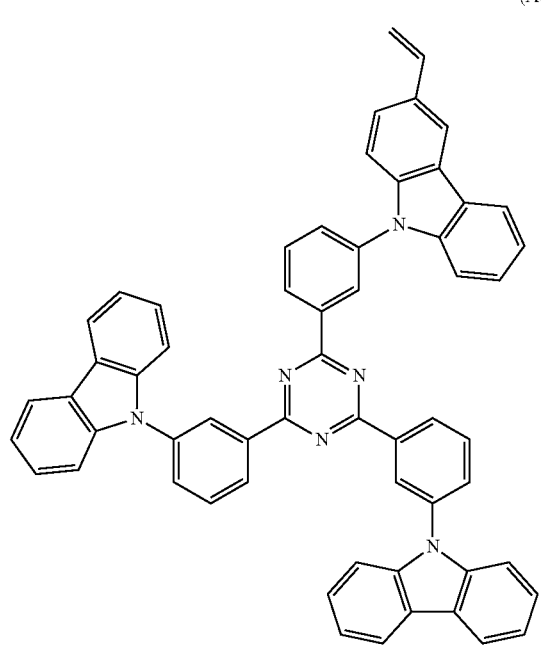
(A88)
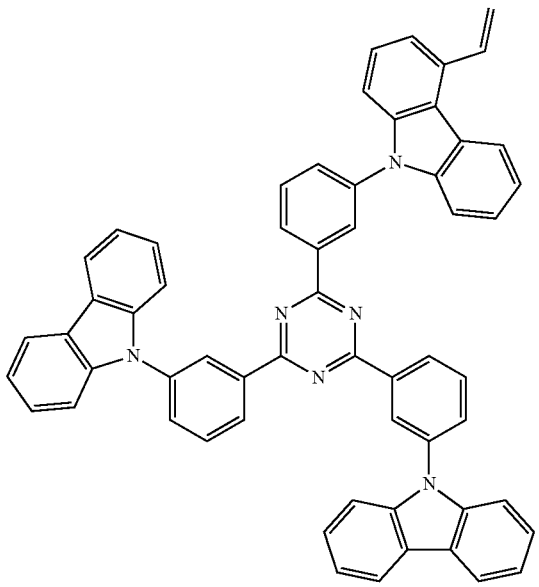
(A89)
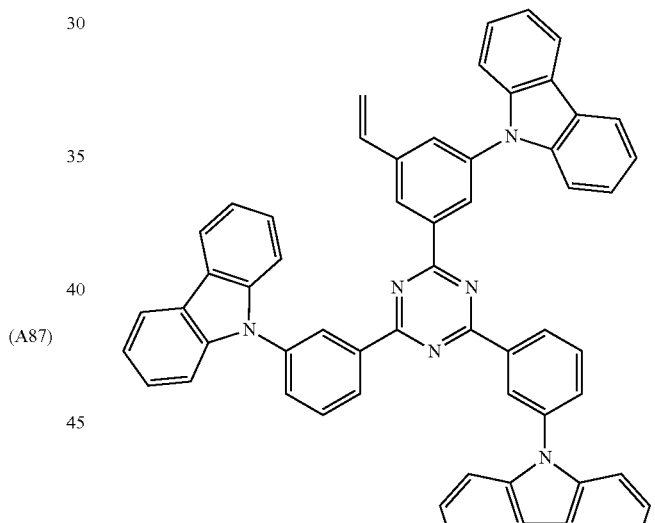
(A90)
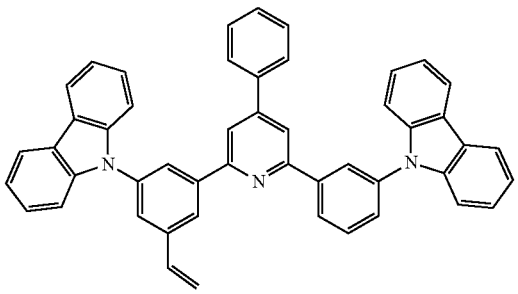

(A91)
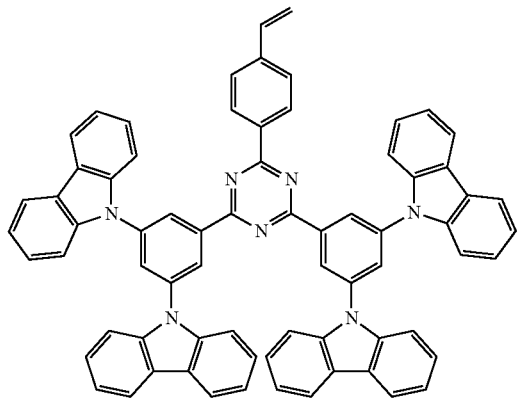
(A92)
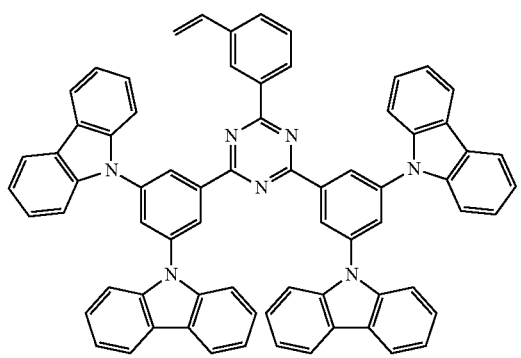
(A93)
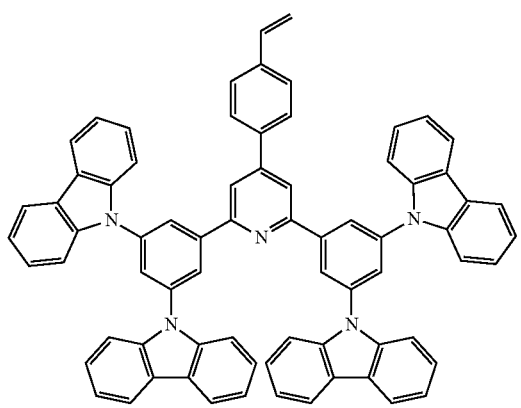
(A94)
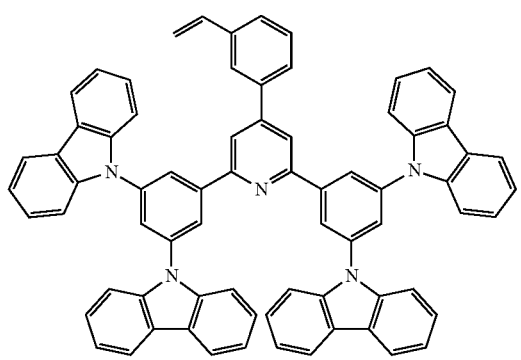
(A95)
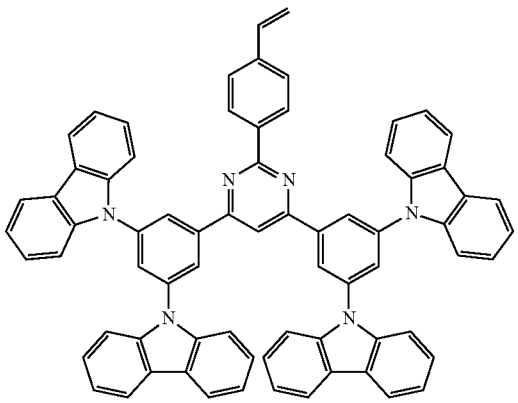
(A96)
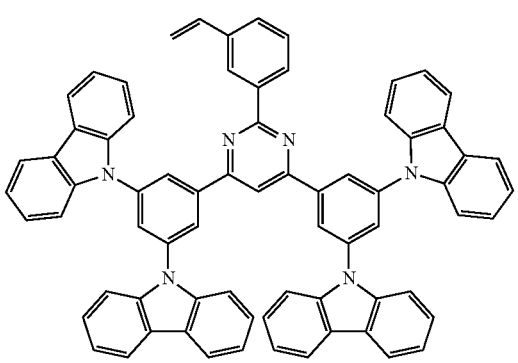
(A97)
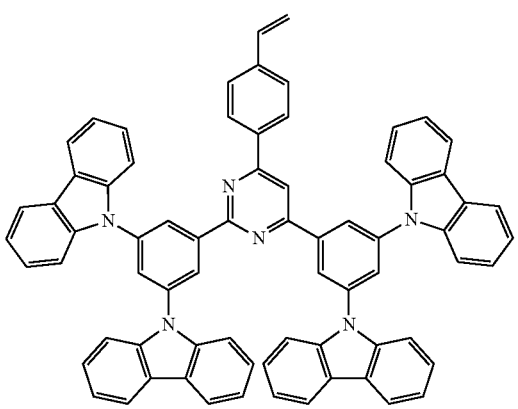
(A98)
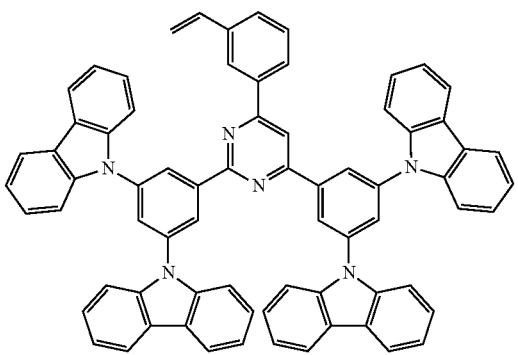

(A99)
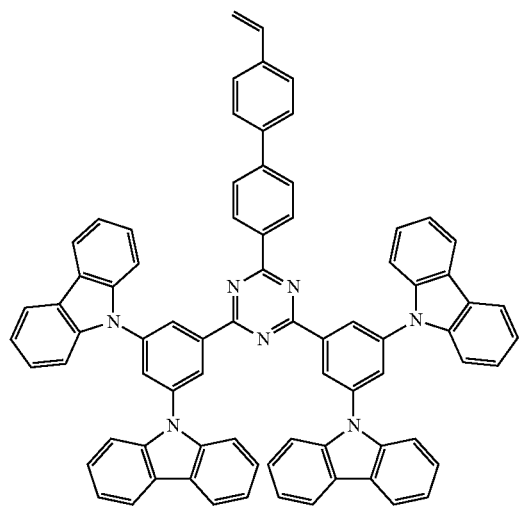
(A100)
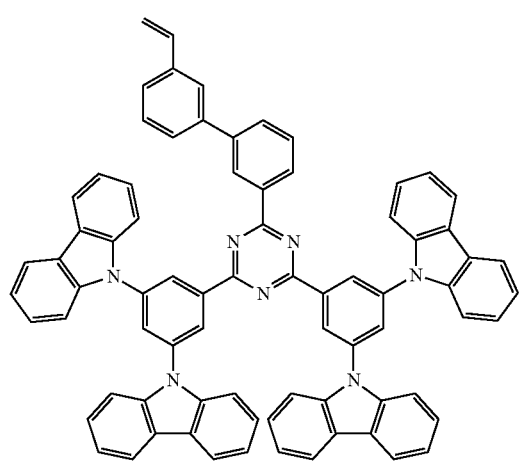
(A101)
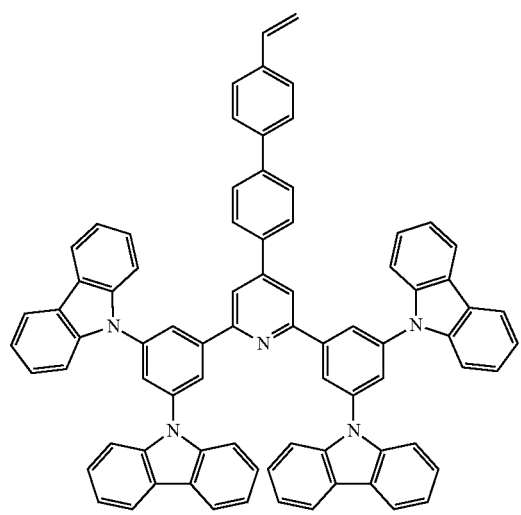
(A102)
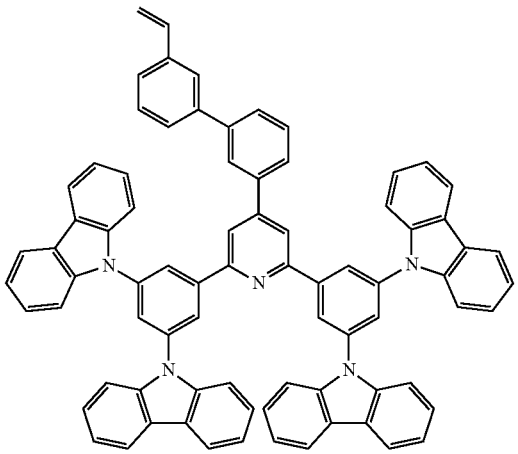
(A103)
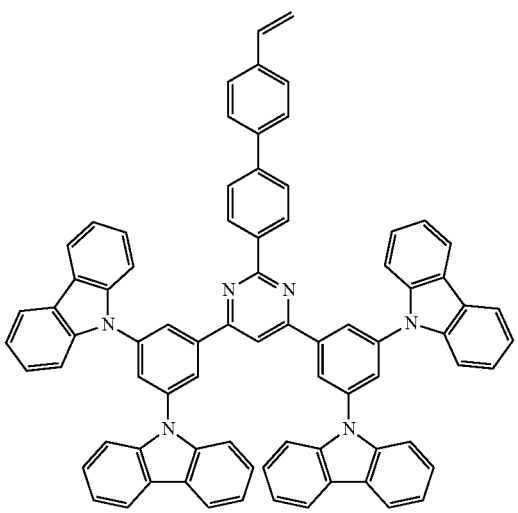
(A104)
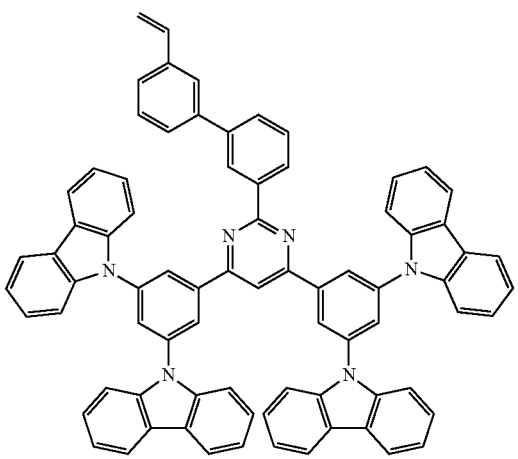

(A105)
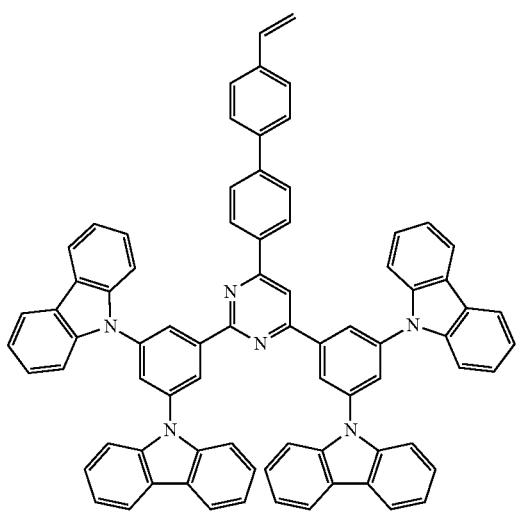

(A106)
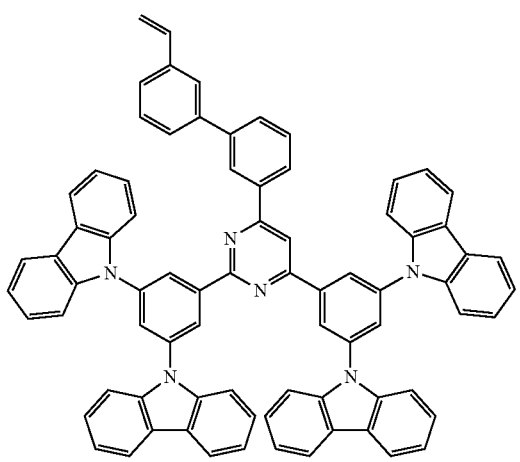

(A107)
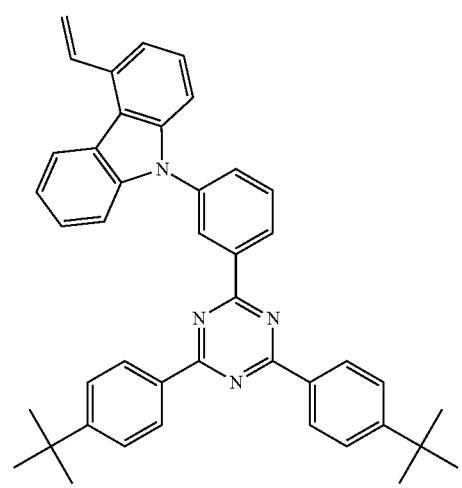

(A108)
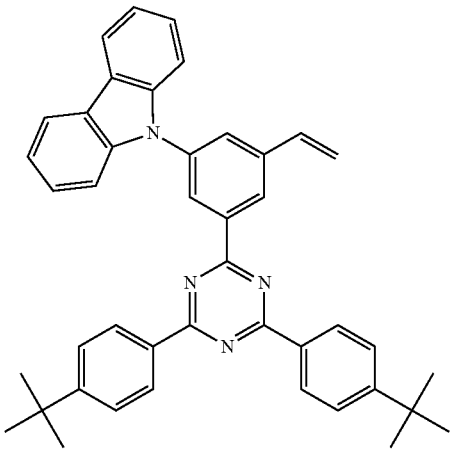

Of these, the compounds represented by the formulas (A1), (A13), (A14), (A15), (A31), (A35), (A40), (A42), (A60), (A71), (A73), (A78), (A79), (A80), (A88), (A89), (A92), (A94), (A96), (A100), (A102), (A104), (A107) and (A108) are preferred and further the compounds represented by the formulas (A13), (A15), (A31), (A40), (A60), (A71), (A78), (A80), (A88) and (A107) are more preferred.

The polymerizable compounds having carrier-transporting properties may be used singly or two or more may be combined for use.

The polymerizable compounds having carrier-transporting properties can be prepared by cyclizing a benzonitrile derivative with 3-bromo-5-iodobenzoylchloride using Lewis acid and thereafter coupling with a vinyl phenyl borate and carbazole in this order with Suzuki coupling method.

In the preparation of the polymer compound (I), other polymerizable compounds may be further used. Examples of the other polymerizable compounds may include compounds having no carrier-transporting properties, for example, (meth) acrylic acid alkyl esters such as methyl acrylate, methyl methacrylate; styrene and derivatives thereof. The other compounds are not limited by them. The polymer compound (I) contains a structure unit derived from the other polymerizable compounds in an amount of preferably 0 to 50 mol % based on 100 mol % of all the structure units.

The production of the polymer compound (I) is carried out using the above-described polymerizable compound by any one of radical polymerization, cation polymerization, anion polymerization and addition polymerization, preferably radical polymerization.

The polymer compound (I) has a weight average molecular weight of usually 1,000 to 2,000,000, preferably 5,000 to 500,000. The weight average molecular weight is preferably in the above range because the polymer compound (I) is soluble in an organic solvent and thereby a uniform thin film can be prepared. The weight average molecular weight is a value determined by using tetrahydrofuran as a solvent at 40° C. with the gel permeation chromatography (GPC) method.

Concerning to the solubility of the polymer compound (1) in an organic solvent such as toluene, chloroform etc, 1 part by mass of the polymer compound (1) is dissolved in preferably 1 to 200 parts by mass, more preferably 10 to 50 parts by mass of the organic solvent. The solubility is preferably in this range because organic EL elements can be easily prepared by a coating method.

Embodiment 2

The polymer compound (II) of the present invention (Embodiment 2) comprises a constituting unit derived from the polymerizable compound having carrier-transporting properties represented by the formula (1) and also comprises a unit derived from a polymerizable compound having hole-transporting properties and is obtainable by polymerizing the polymerizable compound having carrier-transporting properties represented by the formula (1) and the polymerizable compound having hole-transporting properties.

The polymerizable compound having carrier-transporting properties represented by the formula (1) has the same meaning as the polymerizable compound having carrier-transporting properties used in the embodiment 1, the preferable range and the reason thereof are also similar to those described above.

The polymerizable compound having hole-transporting properties preferably contains a carbazole structure or a triphenylamine structure each containing the substituent having the polymerizable functional group, more preferably contains the carbazole structure.

Examples of the polymerizable compound having the carbazole structure or the triphenyl structure may include compounds having the substituent having the polymerizable functional group such as N,N'-diphenyl-N,N'-(3-methylphenyl)-1,1'-biphenyl-4,4' diamine(TPD), N,N,N',N'-tetrakis(3-methylphenyl)-1,1'-(3,3'-dimethyl)biphenyl-4,4' diamine (HMTPD), 4,4',4''-tris(3-methylphenylamino)triphenylamine(m-MTDATA), 9-vinylcarbazole, 9-ethylcarbazole, 4,4'-biscarbazolyl biphenyl (CBP) and 4,4'-biscarbazolyl-2,2'-dimethylbiphenyl (CDBP).

Of these, 9-vinylcarbazole, 9-ethylcarbazole, CBP and CDBP are preferred, and further 9-ethylcarbazole and CDBP are more preferred.

The polymerizable compound having the hole-transporting properties may be used singly or two or more may be combined for use.

The polymerizable compounds having the hole-transporting properties represented by the following formulas (5) and (6) are suitable for the present invention because of having excellent carrier-transporting ability and light physical properties.

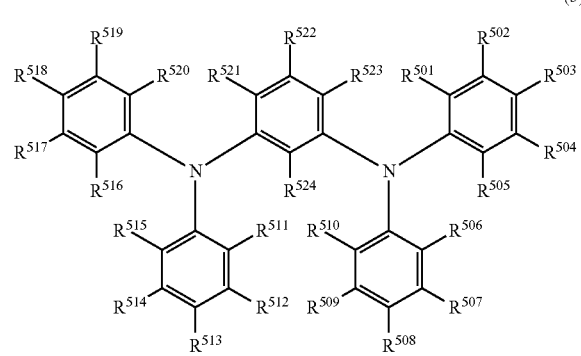

(5)

In the formula (5), at least one of $R^{501}$ to $R^{524}$ is a substituent having a polymerizable functional group, and $R^{501}$ to $R^{524}$, which are not the substituents having a polymerizable functional group, are each independently an atom or a substituent selected from the group consisting of hydrogen, a halogen atom, a cyano group, an alkyl group having 1 to 10 carbon atoms, an aryl group having 6 to 10 carbon atoms, an amino group optionally substituted with an alkyl group having 1 to 10 carbon atoms, an alkoxy group having 1 to 10 carbon atoms, a carbazolyl group and a silyl group.

Examples of the atom or the substituent may include the atom or the substituents as described above. The carbazolyl group may have a substituent such as methyl group, ethyl group, t-butyl group or methoxy group.

In $R^{501}$ to $R^{505}$, $R^{506}$ to $R^{510}$, $R^{511}$ to $R^{515}$, $R^{516}$ to $R^{520}$ and $R^{521}$ to $R^{523}$, adjacent two groups through two carbon atoms, which form a ring, may bond each other to form a condensed ring.

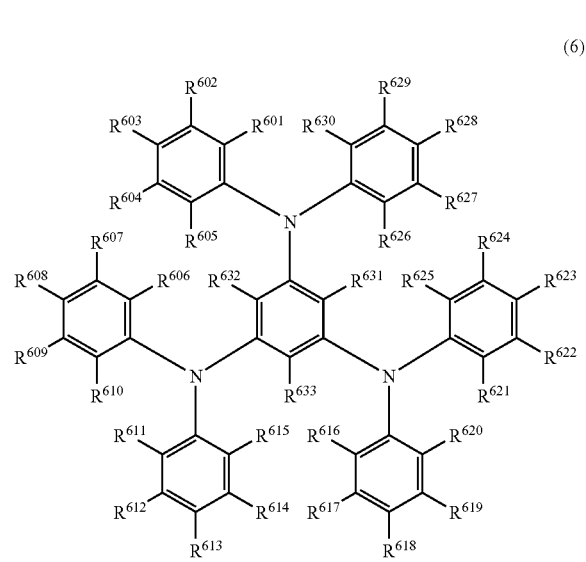

(6)

In the formula (6), at least one of $R^{601}$ to $R^{633}$ is a substituent having a polymerizable functional group, and $R^{601}$ to $R^{633}$, which are not the substituents having a polymerizable functional group, are each independently an atom or a substituent selected from the group consisting of hydrogen atom, a halogen atom, a cyano group, an alkyl group having 1 to 10 carbon atoms, an aryl group having 6 to 10 carbon atoms, an amino group optionally substituted with an alkyl group having 1 to 10 carbon atoms, an alkoxy group having 1 to 10 carbon atoms and a silyl group.

Examples of the atom or the substituent may include the atom or the substituents as described above.

In $R^{601}$ to $R^{605}$, $R^{606}$ to $R^{610}$, $R^{611}$ to $R^{615}$, $R^{616}$ to $R^{620}$, $R^{621}$ to $R^{625}$ and $R^{626}$ to $R^{630}$, adjacent two groups through two carbon atoms, which form a ring, may bond each other to form a condensed ring.

Concerning the polymerizable compound represented by the formula (5), in each of $R^{501}$ to $R^{505}$, $R^{506}$ to $R^{510}$, $R^{511}$ to $R^{515}$ and $R^{516}$ to $R^{520}$, at least one is preferably the atom other than hydrogen atom or the substituent. In this case, $R^{501}$ to $R^{524}$ other than the polymerizable functional group, the atom or the substituent are hydrogen atoms. Furthermore, concerning the polymerizable compound represented by the formula (6), in each of $R^{601}$ to $R^{605}$, $R^{606}$ to $R^{610}$, $R^{611}$ to $R^{615}$, $R^{616}$ to $R^{620}$, $R^{621}$ to $R^{625}$ and $R^{626}$ to $R^{630}$, at least one is preferably the atom other than hydrogen atom or the substituent. In this case, $R^{601}$ to $R^{633}$ other than the polymerizable functional group, the atom or the substituent are hydrogen atoms.

As the substituent having the polymerizable functional group, a substituent represented by the formula (7) is preferred. $R^{701}$ is hydrogen atom or an alkyl group having 1 to 12 carbon atoms. Concerning $R^{701}$, the preferable range and the reason thereof are similar to those as described in the polymerizable compound having electron-transporting properties in the embodiment 1. $X^7$ is a single bond or a group represented by any of the formulas (X71) to (74). Concerning $X^7$, the preferable range and the reason thereof are similar to those as described in the polymerizable compound having electron-transporting properties in the embodiment 1.

Specific examples of the polymerizable compound having hole-transporting properties may include compounds represented by the following formulas (8-1) to (8-11).

(8-1)
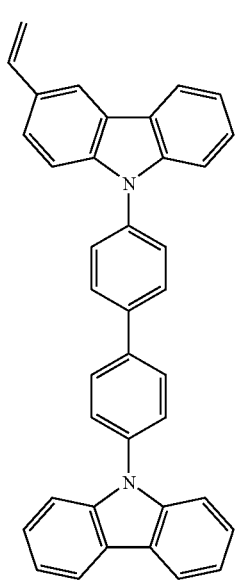

(8-2)
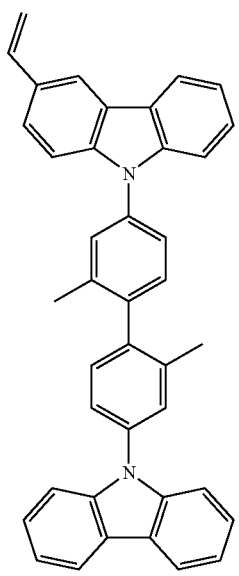

(8-3)
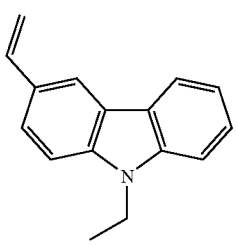

(8-4)
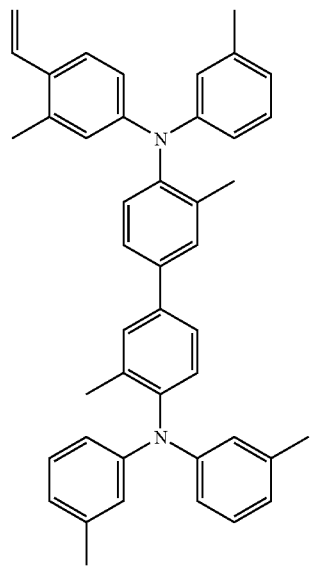

(8-5)
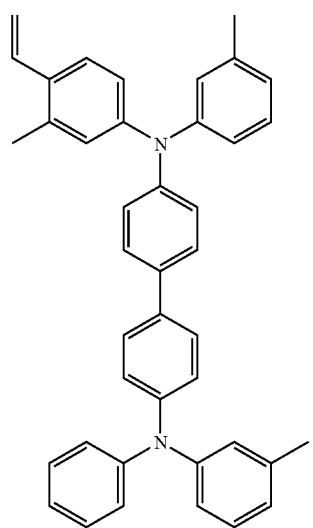

(8-6)
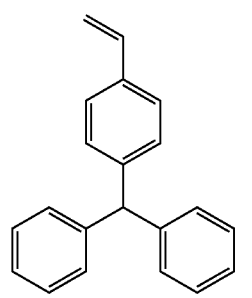

(8-7)
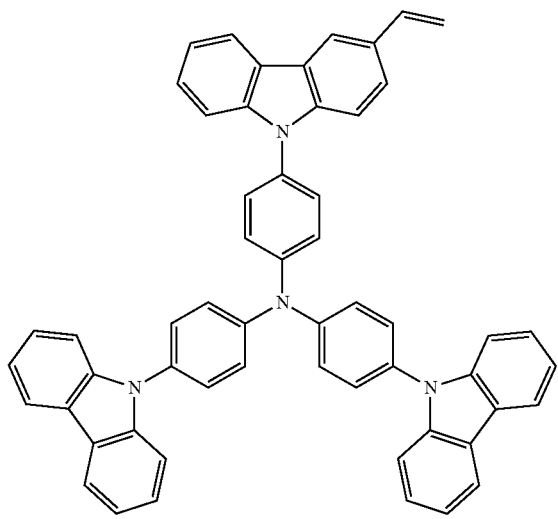

(8-8)
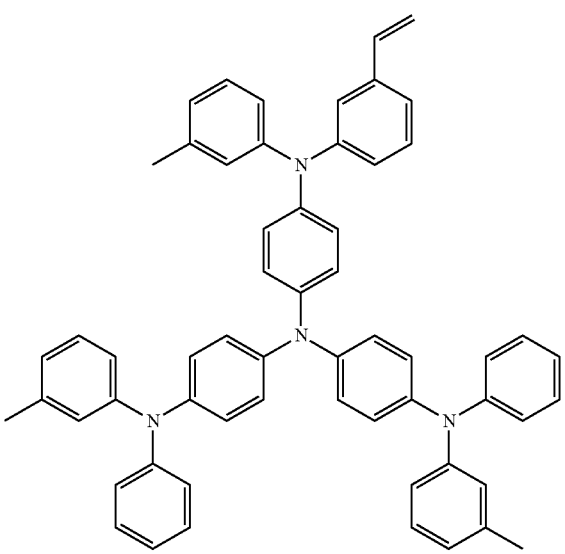

(8-9)
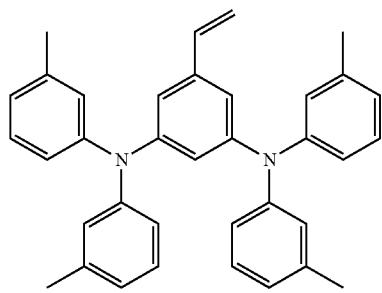

(8-10)
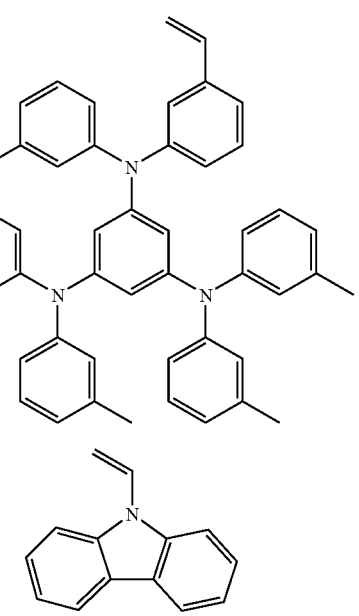

(8-11)

The polymerizable compound having hole-transporting properties may be used singly or two or more may be combined for use.

The compound represented by the formula (5) can be prepared by, for example, palladium catalyst substitution reaction of a m-phenylenediamine derivative and halogenated aryl or palladium catalyst substitution reaction of diarylamine and a m-dibromobenzene derivative. The method for substitution reaction is disclosed in, for example, Tetrahedron Letters, 1998, Vol. 39, p. 2367.

The compound represented by the formula (6) can be prepared by, for example, palladium catalyst substitution reaction of 1,3,5-triaminobenzene and halogenated aryl or palladium catalyst substitution reaction of diarylamine and 1,3,5-trihalogenated benzene. The method for substitution reaction is disclosed in, for example, Tetrahedron Letters, 1998, Vol. 39, p. 2367.

Since in the formula (1), at least one $A^1$ of three $A^1$'s is a condensed polycyclic aromatic group optionally having a heteroatom as a ring-constituting atom (preferably carbazolyl group), the polymerizable compound having hole-transporting properties preferably has a carbazole structure because the difference of the polymerization reacting properties between the polymerizable compound having carrier-transporting properties and the polymerizable compound having hole-transporting properties becomes smaller.

In producing the polymer compound (II), other polymerizable compound further optionally used are the same compound as in the embodiment 1.

The production of the polymer compound (II) may be carried out using the above polymerizable compounds by any of radical polymerization, cation polymerization, anion polymerization and addition polymerization, preferably by radical polymerization.

The weight average molecular weight of the polymer compound (II) is similar to that in the embodiment 1. Furthermore, the solubility of the polymer compound (II) in an organic solvent is similar to that in the embodiment 1.

When the number of the constituting unit derived from the polymerizable compound having hole-transporting properties in the polymer compound (II) is taken as m and the number of the constituting unit derived from the polymerizable compound having carrier-transporting properties represented by the formula (1) is taken as n (m and n are integers of 1 or more), the proportion of the constituting units derived from the polymerizable compound having hole-transporting properties to all the constituting units, namely, the value of m/(m+n) is preferably 0.1 to 0.9, more preferably 0.2 to 0.9, particularly preferably 0.4 to 0.9. When the value of m/(m+n) is in the above range, organic EL elements having high carrier mobility and high durability can be prepared. The proportion of each constituting unit of the polymer compounds is determined by ICP element analysis and $^{13}$C-NMR measurement.

When polymerization is carried out by appropriately regulating the proportion of the polymerizable compound having carrier-transporting properties and the polymerizable compound having hole-transporting properties in the above range, the polymer compound (II) having a desired structure can be prepared.

The polymer compound (II) may be any one of a random copolymer, a block copolymer and an alternating copolymer.

Embodiment 3

The polymer compound (III) of the present invention (Embodiment 3) comprises a constituting unit derived from the polymerizable compound having carrier-transporting properties represented by the formula (1) and a constituting unit derived from the polymerizable compound having hole-transporting properties, and further comprises a constituting unit derived from the polymerizable compound having luminous properties, and is obtainable by polymerizing the polymerizable compound having carrier-transporting properties represented by the formula (1), the polymerizable compound having hole-transporting properties and the polymerizable compound having luminous properties.

The polymerizable compound having carrier-transporting properties represented by the formula (1) and the polymerizable compound having hole-transporting properties have the same meanings as those used in the embodiment 2, and the preferable range and the reason thereof are similar to those.

The polymerizable compound having luminous properties preferably has phosphorescent properties, and is more preferably a transition metal complex having a substituent with a polymerizable functional group, furthermore preferably an iridium complex having a substituent with a polymerizable functional group.

As the iridium complex, complexes represented by the following formula (2) to (4) are preferably used. These polymerizable compounds have a vinyl group, which is a polymerizable functional group.

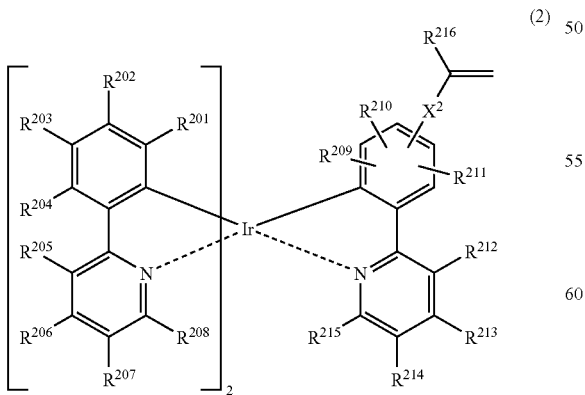

(2)

In the formula (2), $R^{201}$ to $R^{215}$ are each independently an atom or a substituent selected from the group consisting of hydrogen atom, a halogen atom, a cyano group, an alkyl group having 1 to 10 carbon atoms, an aryl group having 6 to 10 carbon atoms, an amino group optionally substituted with an alkyl group having 1 to 10 carbon atoms, an alkoxy group having 1 to 10 carbon atoms and a silyl group.

Examples of the halogen atom are a fluorine atom, a chlorine atom, a boron atom and an iodine atom.

Examples of the alkyl group having 1 to 10 carbon atoms are methyl group, ethyl group, propyl group, isopropyl group, butyl group, isobutyl group, t-butyl group, amyl group, hexyl group, octyl group and decyl group.

Examples of the aryl group having 6 to 10 carbon atoms are phenyl group, tolyl group, xylyl group, mesityl group and naphthyl group.

Examples of the amino groups optionally substituted with an alkyl group having 1 to 10 carbon atoms are amino group, dimethylamino group, diethylamino group and dibutylamino group.

Examples of the alkoxy group having 1 to 10 carbon atoms are methoxy group, ethoxy group, propoxy group, isopropoxy group, butoxy group, isobutoxy group, t-butoxy group, hexyloxy group, 2-ethylhexyloxy group and decyloxy group.

Examples of the silyl group are trimethyl silyl group, triethyl silyl group, t-butyl dimethyl silyl group and trimethoxy silyl group.

Of these, because of having excellent phosphorescent properties, $R^{201}$ to $R^{215}$ are each preferably hydrogen atom, a fluorine atom, cyano group, methyl group, t-butyl group, dimethylamino group, butoxy group or 2-ethyl hexyloxy group, more preferably $R^{202}$ is t-butyl group and $R^{201}$ to $R^{215}$ excluding $R^{202}$ are each hydrogen atom.

In each ring of $R^{201}$ to $R^{204}$, $R^{205}$ to $R^{208}$, $R^{209}$ to $R^{211}$ and $R^{212}$ to $R^{215}$, two groups, which are adjacent through two carbon atoms, may bond each other to form a condensed ring.

$R^{216}$ is hydrogen atom or an alkyl group having 1 to 12 carbon atoms. Examples of the alkyl group having 1 to 12 carbon atoms are the above-described alkyl groups. Of these, $R^{216}$ is preferably hydrogen atom because the carrier-transporting properties are excellent.

$X^2$ is a single bond or a group represented by any of the following formulas (X21) to (X24).

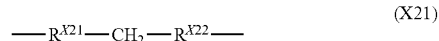 (X21)

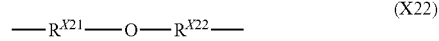 (X22)

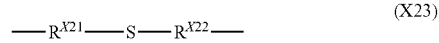 (X23)

 (X24)

In the formulas, $R^{X21}$ is a single bond or an alkylene having 1 to 12 carbon atoms, $R^{X22}$ is a single bond, an alkylene having 1 to 12 carbon atoms or a phenylene group. In the formula (2), $R^{X21}$ preferably bonds to a benzene ring and $R^{X22}$ preferably bonds to a vinyl group. When $X^2$ does not contain a heteroatom, organic EL elements having higher luminous efficiency can be prepared.

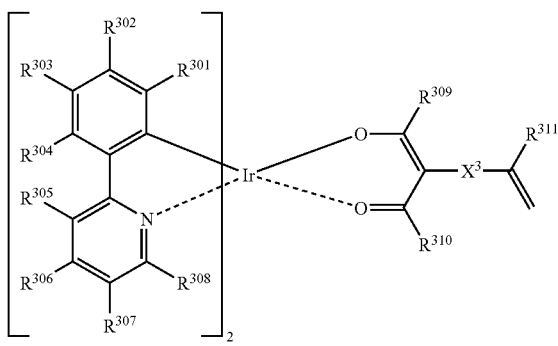

(3)

In the formula (3), $R^{301}$ to $R^{308}$ are each independently the same atom or substituent as those of $R^{201}$.

$R^{309}$ to $R^{310}$ are each independently the same atom or substituent as those of $R^{201}$ (excluding a halogen atom).

Of these, since the phosphorescent properties are excellent, $R^{301}$ to $R^{310}$ are preferably each independently hydrogen atom, a fluorine atom, cyano group, methyl group, t-butyl group, dimethylamino group, butoxy group or 2-ethyl hexyloxy group, and more preferably $R^{302}$ is t-butyl group and $R^{301}$ to $R^{310}$ excluding $R^{202}$ are each independently hydrogen atom.

In each ring of $R^{301}$ to $R^{304}$ and $R^{305}$ to $R^{308}$, two groups, which are adjacent through two carbon atoms, may bond each other to form a condensed ring.

$R^{311}$ is the same atom or substituent as those of $R^{216}$, and the preferable range and the reason thereof are similar to those in $R^{216}$.

$X^3$ is a single bond or a group represented by any of the following formulas (X31) to (X34).

$$—R^{X31}—CH_2—R^{X32}— \quad (X31)$$

$$—R^{X31}—O—R^{X32}— \quad (X32)$$

$$—R^{X31}—S—R^{X32}— \quad (X33)$$

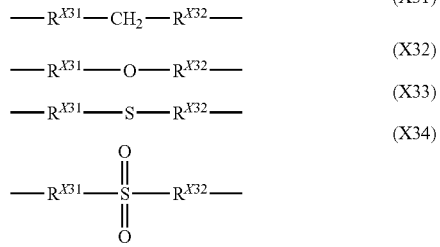

(X34)

In the formulas, $R^{x31}$ is a single bond or an alkylene group having 1 to 12 carbon atoms, and $R^{x32}$ is a single bond, an alkylene group having 1 to 12 carbon atoms or a phenylene group. The preferable range and the reason of $X^3$ are similar to those in $X^2$.

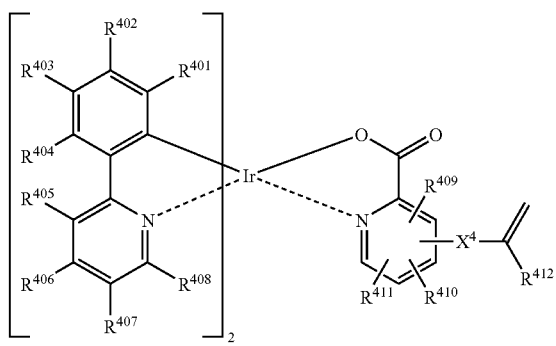

(4)

In the formula (4), $R^{401}$ to $R^{411}$ are each independently the same atom or substituent as those of $R^{201}$.

Of these, since the phosphorescent properties are excellent, $R^{401}$ to $R^{411}$ are preferably each independently hydrogen atom, a fluorine atom, cyano group, methyl group, t-butyl group, dimethylamino group, butoxy group or 2-ethyl hexyloxy group, and more preferably $R^{402}$ is t-butyl group and $R^{401}$ to $R^{411}$ excluding $R^{402}$ are each independently hydrogen atom.

In each ring of $R^{401}$ to $R^{404}$, $R^{405}$ to $R^{408}$ and $R^{409}$ to $R^{411}$, two groups, which are adjacent through two carbon atoms, may bond each other to form a condensed ring.

$R^{412}$ is the same atom or substituent as those of $R^{216}$ and the preferable range and the reason thereof are similar to those $R^{216}$.

$X^4$ is a single bond or a group represented by any of the following formulas (X41) to (X44).

$$—R^{X41}—CH_2—R^{X42}— \quad (X41)$$

$$—R^{X41}—O—R^{X42}— \quad (X42)$$

$$—R^{X41}—S—R^{X42}— \quad (X43)$$

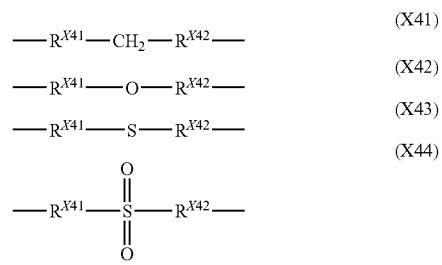

(X44)

In the formulas, $R^{x41}$ is a single bond or an alkylene group having 1 to 12 carbon atoms, and $R^{x42}$ is a single bond, an alkylene group having 1 to 12 carbon atoms or a phenylene group. The preferable range and the reason of $X^4$ are similar to those in $X^2$.

The polymerizable compound having phosphorescent properties may be used singly or two or more may be combined for use.

The polymerizable compound having phosphorescent properties can be prepared by, for example, allowing iridium chloride to react with a phenyl pyridine derivative, thereby preparing a dinuclear complex of iridium (Ir), and allowing it to react with a ligand having a polymerizable functional group (a ligand coordinated in the right side of Ir in the above formulas (2) to (4)).

In producing the polymer compound (III), examples of the other polymerizable compounds optionally used are similar to those in the embodiment 1.

The production of the polymer compound (III) is carried out using the above-described polymerizable compounds by any of radical polymerization, cation polymerization, anion polymerization and addition polymerization, preferably radical polymerization.

The weight average molecular weight of the polymer compound (III) is similar to that in the embodiment 1. The solubility of the polymer compound (III) in an organic solvent is similar to that in the embodiment 1.

In the polymer compound (III), when the number of the constituting unit derived from the polymerizable compound having phosphorescent properties is taken as x and the number of the constituting units derived from the polymerizable compound having carrier-transporting properties represented by the formula (1) and the constituting unit derived from the polymerizable compound having hole-transporting properties is taken as y (x and y are integers of 1 or more), the proportion of the constituting units derived from the polymerizable compound having phosphorescent properties to all the constituting units, namely, the value of x/(x+y) is preferably 0.001 to 0.5, more preferably 0.001 to 0.2. When the value of x/(x+y) is in the above range, organic EL elements having high carrier mobility, low influence by concentration quenching and high luminous efficiency can be prepared.

In the polymer compound (III), when the number of the constituting unit derived from the polymerizable compound having hole-transporting properties is taken as m and the number of the constituting unit derived from the polymerizable compound having carrier-transporting properties is taken as n (m and n are integers of 1 or more), m, n and y satisfy the following relation y=m+n. As to the proportion of the number of the constituting unit derived from the polymerizable compound having hole-transporting properties to the number of the constituting unit derived from the compound having electric charge-transporting properties m/y, and the proportion of the number of the constituting unit derived from the polymerizable compound having carrier-transporting properties to the number of the constituting unit derived from the compound having electric charge-transporting properties n/y, the optimums are determined by the electric charge-transporting ability and concentration of each constituting unit. When a luminous layer of an organic EL element is formed by only the polymer compound (III), the values of m/y and n/y are each in the range of preferably 0.05 to 0.95, more preferably 0.20 to 0.80. Here, m, n and y satisfy the following relation m/y+n/y=1. The proportion of each constituting unit of the above polymer compound is determined by ICP element analysis and $^{13}$C-NMR measurement.

Appropriately regulating the proportion of the polymerizable compound having carrier-transporting properties, the polymerizable compound having hole-transporting properties and the polymerizable compound having phosphorescent properties in the above ranges, the polymerization is carried out, to prepare the polymer compound (III) having a desired structure.

The polymer compound (III) may be any one of a random copolymer, a block copolymer and an alternating copolymer.

Embodiment 4

The polymer compound (IV) of the present invention (Embodiment 4) comprises the constituting unit derived from the polymerizable compound having carrier-transporting properties represented by the formula (1) and a constituting unit derived from the polymerizable compound having hole-transporting properties, and further comprises a constituting unit derived from the polymerizable compound having electron-transporting properties, and is obtainable by polymerizing the polymerizable compound having carrier-transporting properties represented by the formula (1) and the polymerizable compound having hole-transporting properties and the polymerizable compound having electron-transporting properties.

The polymerizable compound having carrier-transporting properties represented by the formula (1) and the polymerizable compound having hole-transporting properties have the same meanings as those of the polymerizable compound having carrier-transporting properties used in the embodiment 2, and the preferable range and the reason thereof are similar to the embodiment 2.

The polymerizable compound having electron-transporting properties preferably has an aromatic heterocyclic structure or a triaryl boron structure both containing a substituent having a polymerizable functional group, more preferably an aromatic ring structure.

In producing the polymer compound (IV), usable other polymer compounds are the same compounds in the embodiment 1.

The polymer compound (IV) may be produced using the above-described polymerizable compounds by any of radical polymerization, cation polymerization, anion polymerization and addition polymerization, preferably radical polymerization.

The weight average molecular weight of the polymer compound (IV) is similar to that in the embodiment 1. The solubility of the polymer compound (IV) in an organic solvent is similar to that in the embodiment 1.

In the polymer compound (IV), when the number of the constituting unit derived from the polymerizable compound having electron-transporting properties is taken as x', the number of the constituting units derived from the polymerizable compound having hole-transporting properties is taken as y' and the number of the constituting units derived from the polymerizable compound having carrier-transporting properties represented by the formula (1) is taken as z' (x', y' and z' are integers of 1 or more), the proportion of the constituting units derived from the polymerizable compound having electron-transporting properties to all the constituting units, namely, the value of x'/(x'+y'+z') is preferably 0.1 to 0.9, more preferably 0.1 to 0.5, furthermore preferably 0.1 to 0.3. When the value of x'/(x'+y'+z') is in the above range, organic EL elements having excellent carrier mobility and high durability can be prepared. The proportion of each constituting unit of the above polymer compound is determined by ICP element analysis and $^{13}$C-NMR measurement.

Appropriately regulating the proportion of the polymerizable compound having carrier-transporting properties, the polymerizable compound having hole-transporting properties and the polymerizable compound having electron-transporting properties in the above ranges, the polymerization is carried out, to prepare the polymer compound (IV) having a desired structure.

The polymer compound (IV) may be any of a random copolymer, a block copolymer and an alternating copolymer.

Embodiment 5

The polymer compound (V) of the present invention (Embodiment 5) comprises the constituting unit derived from the polymerizable compound having carrier-transporting properties represented by the formula (1), the constituting unit derived from the polymerizable compound having hole-transporting properties, the constituting unit derived from the polymerizable compound having electron-transporting properties and a constituting unit derived from the polymerizable compound having luminous properties, and is obtainable by polymerizing the polymerizable compound having carrier-transporting properties represented by the formula (1), the polymerizable compound having hole-transporting properties, the polymerizable compound having electron-transporting properties and the polymerizable compound having luminous properties.

The polymerizable compound having carrier-transporting properties represented by the formula (1), the polymerizable compound having hole-transporting properties, the polymerizable compound having electron-transporting properties and the polymerizable compound having luminous properties have the same meanings as those used in each of the embodiments 1 to 4, and the preferable range and the reason thereof are similar to the embodiments.

In producing the polymer compound (V), usable other polymer compounds are the same compounds in the embodiment 1.

The polymer compound (V) may be produced using the above-described polymerizable compounds by any of radical polymerization, cation polymerization, anion polymerization and addition polymerization, preferably radical polymerization.

The weight average molecular weight of the polymer compound (V) is similar to that in the embodiment 1. The solubility of the polymer compound (V) in an organic solvent is similar to that in the embodiment 1.

In the polymer compound (V), when the number of the constituting unit derived from the polymerizable compound having electron-transporting properties is taken as p, the number of the constituting unit derived from the polymerizable compound having luminous properties is taken as q, the number of the constituting units derived from the polymerizable compound having hole-transporting properties is taken as r and the number of the constituting units derived from the polymerizable compound having carrier-transporting properties represented by the formula (1) is taken as s (p to s are integers of 1 or more), the proportion of the constituting units derived from the polymerizable compound having electron-transporting properties to all the constituting units, namely, the value of p/(p+q+r+s) is preferably 0.1 to 0.9, more preferably 0.1 to 0.5, furthermore preferably 0.1 to 0.3. Furthermore, the proportion of the constituting units derived from the polymerizable compound having luminous properties to all the constituting units, namely, the value of q/(p+q+r+s) is preferably 0.001 to 0.5, more preferably 0.001 to 0.2. When the proportion of the constituting units derived from the polymerizable compound having electron-transporting properties and the polymerizable compound having luminous properties to all the constituting units is in the above range, organic EL elements having high carrier mobility and high durability can be prepared. The proportion of each constituting unit of the above polymer compound is determined by ICP element analysis and $^{13}$C-NMR measurement.

Appropriately regulating the proportion of the polymerizable compound having carrier-transporting properties, the polymerizable compound having hole-transporting properties, the polymerizable compound having electron-transporting properties and the polymerizable compound having luminous properties in the above ranges, the polymerization is carried out, to prepare the polymer compound (V) having a desired structure.

The polymer compound (V) may be any of a random copolymer, a block copolymer and an alternating copolymer.

Embodiment 6

In the organic EL element of the present invention (Embodiment 6), one luminous layer, which comprises a specific polymer compound (I) and a polymer compound (I') is provided between an anode and a cathode, wherein the polymer compound (I') has the constituting units derived from the luminous compound described later and the polymerizable compound having hole-transporting properties described later. In this case, the luminous layer contains the luminous compound in an amount of 0.1 to 50 parts by weight, more preferably 0.5 to 30 parts by weight and the polymer compound (I') in an amount of 10 to 200 parts by weight, more preferably 50 to 150 parts by weight based on 100 parts by weight of the polymer compound (I). As described above, forming the luminous layer from the polymer compound having carrier-transporting properties (I), the luminous compound and the polymer compound having hole-transporting properties (I'), organic EL elements having high luminous efficiency can be prepared even if other organic material layers are not provided.

Examples of the luminous compound are preferably phosphorescent compounds, more preferably an iridium complex.

Preferably usable examples of the iridium complex are the following complexes (E-1) to (E-39).

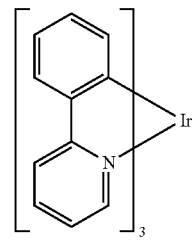

E-1

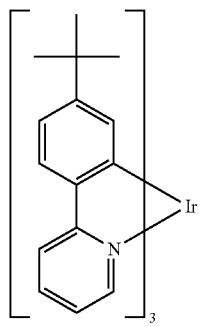

E-2

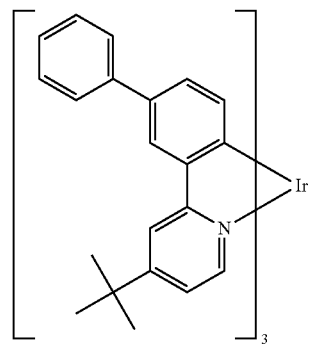

E-3

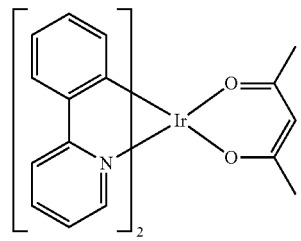

E-4

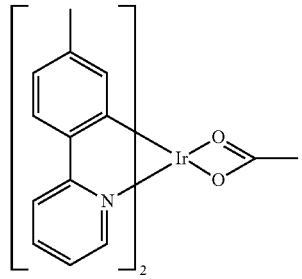

E-5

E-6 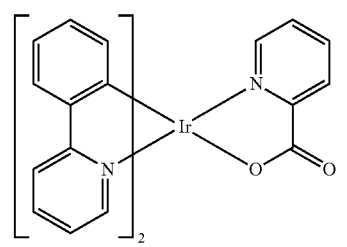
E-7 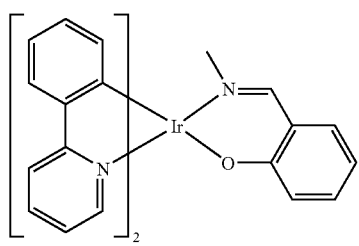
E-8 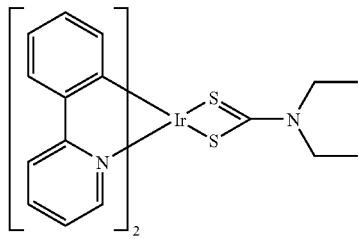
E-9 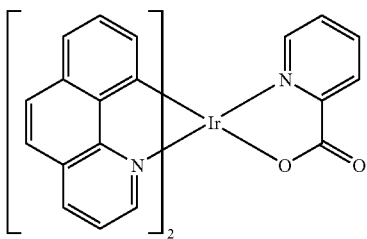
E-10 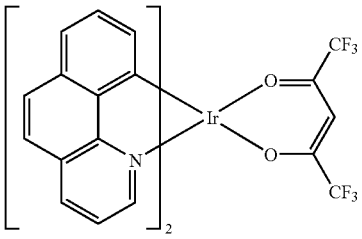
E-11 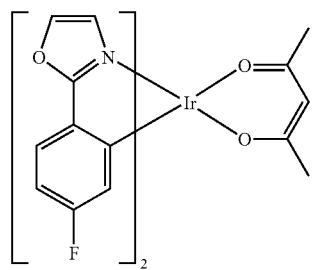
E-12 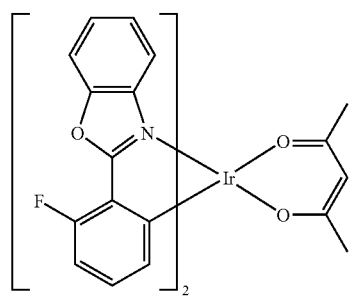
E-13 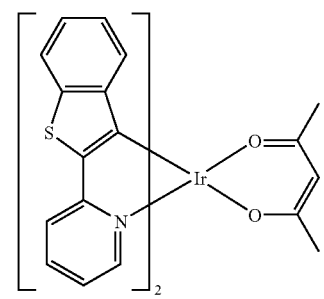
E-14 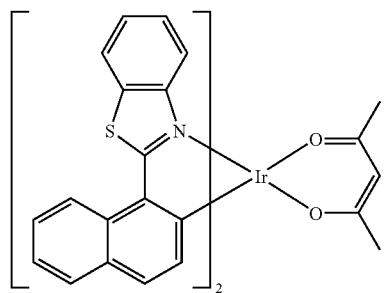
E-15 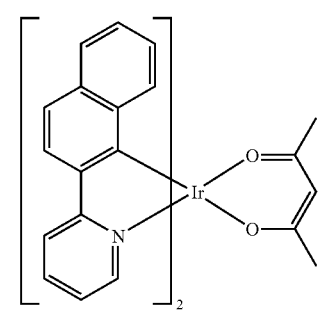
E-16 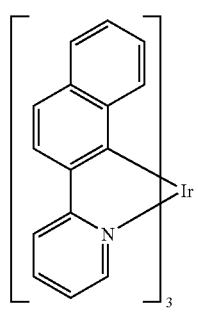

E-17 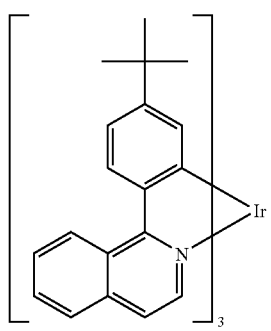
E-18 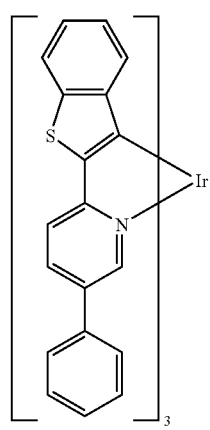
E-19 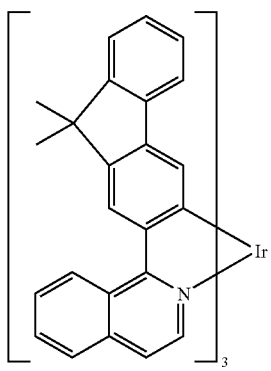
E-20 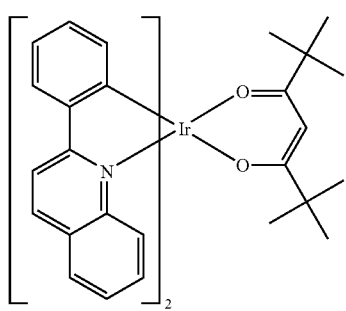
E-21 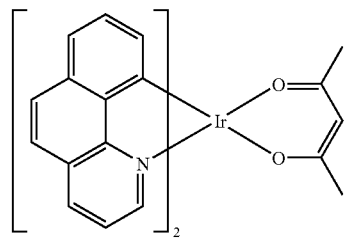
E-22 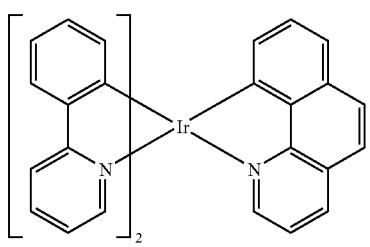
E-23 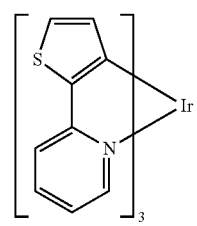
E-24 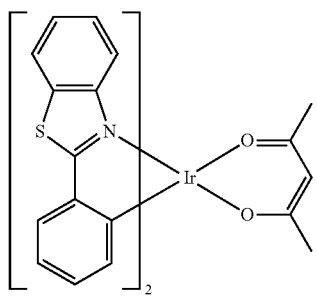
E-25 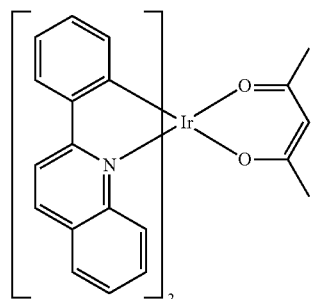
E-26 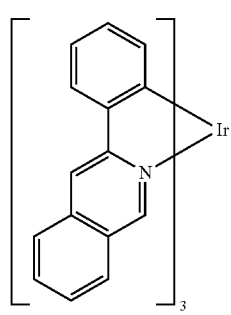

E-27
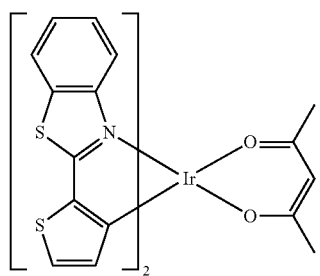
E-28
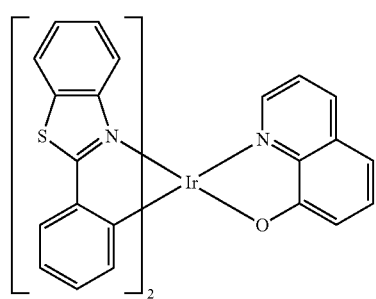
E-29
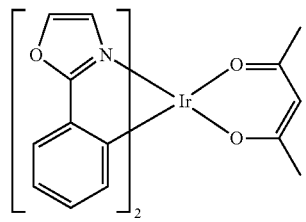
E-30
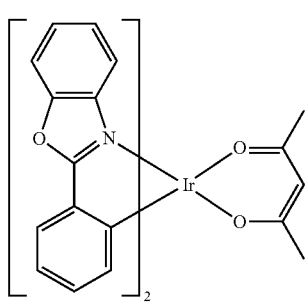
E-31
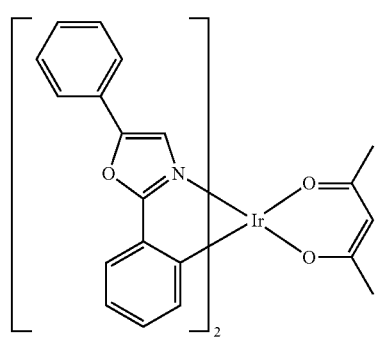
E-32
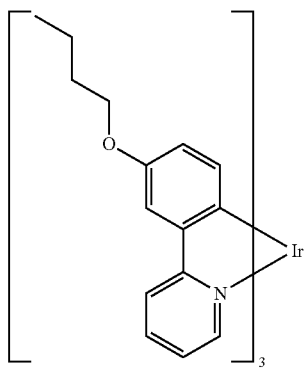
E-33
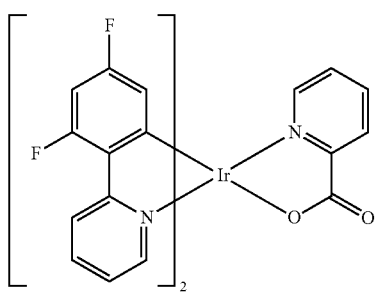
E-34
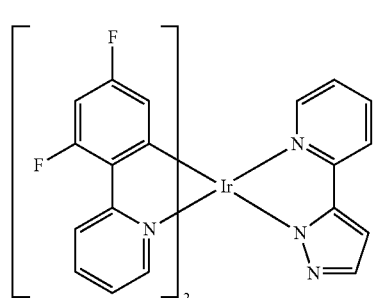
E-35
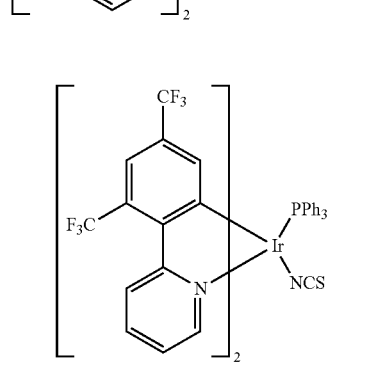
E-36
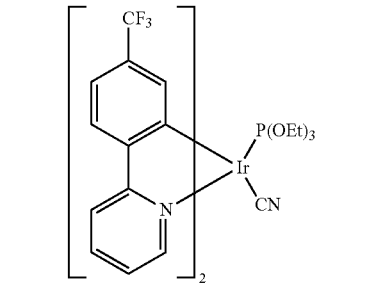

-continued

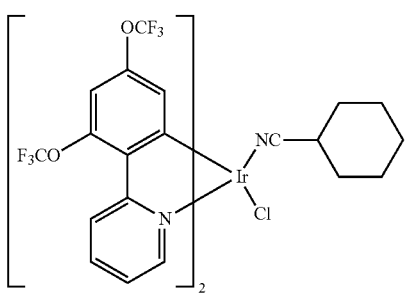

E-37

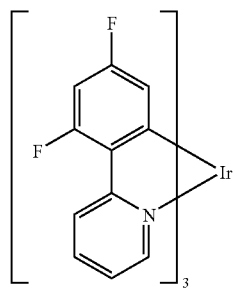

E-38

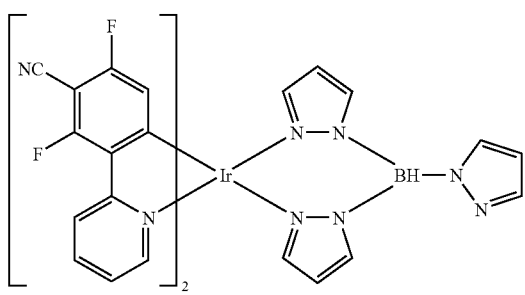

E-39

Of these, the compounds represented by the formulas E-1, E-2, E-6, E-33, E-34, E-38 and E-39 are more preferred, and the compounds represented by the formulas E-33 and E-38 are furthermore preferred.

The luminous compound may be used singly and two or more may be combined for use.

The polymer compound (I') is obtainable by polymerizing the polymerizable compound having hole-transporting properties. The above polymerizable compound having hole-transporting properties has the same meaning as the polymerizable compound having hole-transporting properties used in the embodiment 3, and the preferred range and the reason thereof are similar to those in the embodiment 3.

The polymer compound (I') may be produced using the above-described polymerizable compounds by any of radical polymerization, cation polymerization, anion polymerization and addition polymerization, preferably radical polymerization.

The polymer compound (I') has a weight average molecular weight of usually 1,000 to 2,000,000, preferably 5,000 to 500,000. The polymer compound (I') preferably has a weight average molecular weight in the above range, because the polymer compound (I') is soluble in an organic solvent and uniform thin films are prepared. The weight average molecular weight is a value determined by measuring at 40° C. using tetrahydrofuran as a solvent with gel permeation chromatography (GPC) method. The solubility of the polymer compound (I') in an organic solvent is the same as that in the embodiment 1.

In the production of the organic EL element having one luminous layer, which comprises the polymer compound (I), the luminous compound and the polymer compound (I'), between an anode and a cathode, the luminous layer is usually formed on an anode provided on a substrate in the following manner. First, a solution in which the polymer compound (I), the luminous compound and the polymer compound (I') are dissolved is prepared. Although a solvent used in the preparation of the solution is not particularly limited, examples of the solvent are chlorine solvents such as chloroform, methylene chloride, dichloroethane etc; ether solvents such as tetrahydrofuran, anisole etc; aromatic hydrocarbon solvents such as toluene, xylene etc; ketone solvents such as acetone, methylethyl ketone etc; and ester solvents such as ethyl acetate, butyl acetate, ethyl cellosolve acetate etc. Next, the solution thus prepared is applied on the substrate by wet film forming methods such as spin coating method, casting method, micro-gravure coating method, gravure coating method, bar coating method, roll coating method, wire bar coating method, dip coating method, spray coating method, screen printing method, flexographic printing method, offset printing method or ink jet printing method, to form a film. For example, in the spin coating method or the dip coating method, depending on the compounds used and the film forming conditions, the solution preferably contains the luminous compound in an amount of 0.5 to 30 parts by mass, the polymer compound (I') in an amount of 10 to 200 parts by mass and the solvent in an amount of 1000 to 20000 parts by mass based on 100 parts by mass of the polymer compound (I).

Providing a cathode on the luminous layer thus formed, the organic EL element of the embodiment 6 can be prepared.

As the substrate used in the embodiment 6, a transparent substrate having insulating properties against the luminous wavelength of the luminous material is favorably used. Examples of the substrate are glasses and transparent plastics such as PET (polyethylene terephthalate), polycarbonate etc.

As an anode material used in the embodiment 6, it is preferred to use known transparent conductive materials, such as ITO (indium tin oxide), tin oxide, zinc oxide and conductive polymers including polythiophene, polypyrol, polyaniline, etc. The electrode formed by the transparent conductive material has a surface resistance of preferably 1 to 50Ω/□ (ohm/square). The anode has a thickness of preferably 50 to 300 nm.

As the cathode material used in the embodiment 6, it is preferred to use known cathode materials, for example, alkali metals such as Li, Na, K, Cs, etc; alkali earth metals such as Mg, Ca, Ba, etc; Al; MgAl alloy; alloys of Al and an alkali metal or an alkali earth metal, such as AlLi, AlCa, etc. The cathode has a thickness of preferably 10 nm to 1 μm, more preferably 50 to 500 nm. When a metal having high activity such as an alkali metal or an alkali earth metal is used, the cathode has a thickness of preferably 0.1 to 100 nm, more preferably 0.5 to 50 nm. In this case, on the cathode, a metal layer stable to the air is laminated for protecting the cathode metal. Examples of the metal forming the metal layer may include Al, Ag, Au, Pt, Cu, Ni, Cr, etc. The metal layer has a thickness of preferably 10 nm to 1 μm, more preferably 50 to 500 nm.

Examples of the film forming method using the anode material may include electron beam vapor deposition method, sputtering method, chemical reaction method and coating method, and examples of the film forming method using the cathode material may include resistance heat vapor deposition method, electron beam vapor deposition method, sputtering method and ion plating method.

Embodiment 7

In the organic EL element of the present invention (Embodiment 7), between an anode and a cathode, provided is one luminous layer, which comprises a specific polymer compound (II) and the luminous compound shown in the embodiment 6. In this case, the luminous layer contains the luminous compound in an amount of 0.1 to 50 parts by mass, more preferably 0.5 to 30 parts by mass based on 100 parts by mass of the polymer compound (II). As described above, forming the luminous layer from the polymer compound having carrier-transporting properties and hole-transporting properties (II) and the luminous compound, organic EL elements having high luminous efficiency can be prepared even if other organic material layers are not provided.

The luminous layer is usually formed on the anode provided on the substrate in the following way. First, a solution is prepared by dissolving the polymer compound (II) and the luminous compound. The solvent used in the preparation of the solution is the same as that used in the embodiment 5. The film forming of the solution is similar to that in the embodiment 6. In the spin coating method or the dip coating method, depending on the compound used and the film forming conditions, for example, the solution preferably contains the luminous compound in an amount of 0.5 to 30 parts by mass and the solvent in an amount of 1000 to 20000 parts by mass based on 100 parts by mass of the polymer compound (II).

Providing the cathode on the luminous layer thus formed, the organic EL element of the embodiment 7 is prepared.

Furthermore, the substrate, the anode material, the cathode material and the film forming methods using the anode material and the cathode material are similar to the embodiment 6.

Embodiment 8

In the organic EL element of the present invention (Embodiment 8), between an anode and a cathode, provided is one luminous layer, which comprises a specific polymer compound (III). When the luminous layer is formed using the polymer compound having carrier-transporting properties, phosphorescent properties and hole-transporting properties (III), organic EL elements having high luminous efficiency can be prepared even if other organic material layers are not provided. Moreover, since the luminous layer comprises only the polymer compound (III) in the embodiment 8, the preparation process can be more simplified.

The luminous layer is usually formed on the anode provided on the substrate in the following way. First, a solution is prepared by dissolving the polymer compound (III). The solvent used in the preparation of the solution is the same as that used in the embodiment 6. The film forming of the solution is similar to the embodiment 6. In the spin coating method or the dip coating method, depending on the compound used and the film forming conditions, for example, the solution preferably contains the solvent in an amount of 1000 to 20000 parts by mass based on 100 parts by mass of the polymer compound (III).

Providing the cathode on the luminous layer thus formed, the organic EL element of the embodiment 8 is prepared.

Furthermore, the substrate, the anode material, the cathode material and the film forming methods using the anode material and the cathode material in the embodiment 8 are similar to the embodiment 6.

Embodiment 9

In the organic EL element of the present invention (Embodiment 9), one luminous layer, which comprises a specific polymer compound (IV) and the luminous compound shown in the embodiment 6, is provided between an anode and a cathode. In this case, the luminous layer contains the luminous compound in an amount of preferably 0.1 to 50 parts by mass, more preferably 0.5 to 30 parts by mass based on 100 parts by mass of the polymer compound (IV). As described above, forming the luminous layer from the polymer compound having carrier-transporting properties, electron-transporting properties and hole-transporting properties (IV) and the luminous compound, organic EL elements having high luminous efficiency can be prepared even if other organic material layers are not provided.

The luminous layer is usually formed on the anode provided on the substrate in the following way. First, a solution is prepared by dissolving the polymer compound (IV) and the luminous compound. The solvent used in the preparation of the solution is the same as that used in the embodiment 6. The film forming method of the solution is similar to the embodiment 6. In the spin coating method or the dip coating method, depending on the compound used and the film forming conditions, for example, the solution preferably contains the luminous compound in an amount of 0.5 to 30 parts by mass and the solvent in an amount of 1000 to 20000 parts by mass based on 100 parts by mass of the polymer compound (IV).

Providing the cathode on the luminous layer thus formed, the organic EL element of the embodiment 9 is prepared.

Furthermore, the substrate, the anode material, the cathode material and the film forming methods using the anode material and the cathode material in the embodiment 9 are similar to the embodiment 6.

Embodiment 10

In the organic EL element of the present invention (Embodiment 10), one luminous layer, which comprises a specific polymer compound (V), is provided between an anode and a cathode. In forming the luminous layer from the polymer compound having carrier-transporting properties, hole-transporting properties, electron-transporting properties and phosphorescent properties (V), organic EL elements having high luminous efficiency can be prepared even if other organic material layers are not provided. Moreover, since the luminous layer comprises only the polymer compound (V) in the embodiment 10, the preparation process can be more simplified.

The luminous layer is usually formed on the anode provided on the substrate in the following way. First, a solution is prepared by dissolving the polymer compound (V). The solvent used in the preparation of the solution is the same as that used in the embodiment 6. The film forming method of the solution is similar to the embodiment 6. In the spin coating method or the dip coating method, depending on the compound used and the film forming conditions, for example, the solution preferably contains the solvent in an amount of 1000 to 20000 parts by mass based on 100 parts by mass of the polymer compound (V).

Providing the cathode on the luminous layer thus formed, the organic EL element of the embodiment 10 is prepared.

Furthermore, the substrate, the anode material, the cathode material and the film forming methods using the anode material and the cathode material in the embodiment 10 are similar to the embodiment 6.

Embodiment 11

The organic EL element of the present invention (Embodiment 11) comprises, between an anode and a cathode, the luminous layer as described in any one of the embodiments 6 to 10, and optionally comprises other organic layers.

Examples of the other organic layers are a hole-transporting layer, an electron-transporting layer, a hole block layer and a buffer layer. Providing these organic layers, the luminous efficiency can be further enhanced.

One example of the structure of the organic EL element (Embodiment 11) according to the present invention is shown in FIG. 1. In FIG. 1, between an anode (2) and a cathode (6)

provided on a transparent substrate (1), a hole-transporting layer (3), a luminous layer (4) as described in the embodiment 1 or 2, and an electron-transporting layer (5) are provided in this order.

In the embodiment 11, between the anode (2) and the cathode (6), any one of 1) the hole-transporting layer/the luminous layer and 2) the luminous layer/the electron-transporting layer may be provided.

Each organic layer may be formed by mixing a polymer material and the like as a binder. Examples of the polymer material may include polymethylmethacrylate, polycarbonate, polyester, polysulfone and polyphenylene oxide.

Furthermore, each layer may be formed by each singly using the compound having hole-transporting properties and the compound having electron-transporting properties used in the hole-transporting layer and the electron-transporting layer, or mixing the materials having different functions.

Examples of the compound having hole-transporting properties used for forming the hole-transporting layer may include TPD(N,N'-dimethyl-N,N'-(3-methylphenyl)-1,1'-biphenyl-4,4' diamine); α-NPD (4,4'-bis[N-(1-naphthyl)-N-phenylamino]biphenyl); low molecular triphenylamine derivatives such as m-MTDATA (4, 4', 4"-tris (3-methylphenylphenylamino)triphenylamine etc; polyvinyl carbazole; polymer compounds obtainable by introducing a polymerizable functional group to the above triphenylamine derivative and polymerizing; fluorescent polymer compounds such as polyparaphenylenevinylene, polydialkylfluorene, etc. Examples of the polymer compound are polymer compounds having a triphenylamine skeleton as disclosed in JP-A-H8 (1996)-157575. The compound having hole-transporting properties may be used singly or two or more may be mixed for use, and further, a compound having different hole-transporting properties may be laminated on them. The hole-transporting layer usually has a thickness, which depends on the conductivity of the hole-transporting layer, of preferably 1 nm to 5 μm, more preferably 5 nm to 1 μm, particularly preferably 10 nm to 500 nm.

Examples of the compound having electron-transporting properties for forming the electron-transporting layer may include quinolinol derivative metal complexes such as Alq3 (aluminum trisquinolinolate) etc; low molecular compounds such as oxadiazole derivative, triazole derivative, imidazole derivative, triazine derivative, triarylborane derivative, etc; and polymer compounds obtainable by introducing a polymerizable substituent to the above low molecule compound and polymerizing. Examples of the polymer compound may include poly PBD etc as disclosed in JP-A-H10 (1998)-1665. The compound having electron-transporting properties may be used singly or two or more may be mixed for use, and further a compound having different electron-transporting properties may be laminated on them. The electron-transporting layer usually has a thickness, which depends on the conductivity of the electron-transporting layer, of preferably 1 nm to 5 μm, more preferably 5 nm to 1 μm particularly preferably 10 nm to 500 nm.

Adjacent to the cathode side of the luminous layer, a hole blocking layer may be provided in order to depress passing of holes through the luminous layer and to re-combine holes with electrons efficiently in the luminous layer. For forming the hole blocking layer, known materials such as a triazole derivative, an oxadiazole derivative, a phenanethroline derivative, etc are used.

Moreover, between the anode and the hole-transporting layer, or between the anode and the organic layer laminated adjacently to the anode, a buffer layer may be provided in order to buffer the injection barrier in hole injection. In order to form the buffer layer, known materials such as copper phthalocyanine, a mixture of polyethylene dioxythiophene and polystyrene sulfonate (PEDOT:PSS), etc are used.

Furthermore, between the cathode and the electron-transporting layer, or between the cathode and the organic layer laminated adjacently to the cathode, an insulating layer having a thickness of 0.1 to 10 nm may be provided in order to enhance the electron injecting efficiency. For forming the insulating layer, known materials such as lithium fluoride, sodium fluoride, magnesium fluoride, magnesium oxide, alumina, etc are used.

As the processes for forming the hole-transporting layer and the electron-transporting layer, it is possible to use, for example, dry film forming methods such as resistance heat vapor deposition method, electron beam vapor deposition method or sputtering method; and wet film forming methods such as spin coating method, casting method, micro-gravure coating method, gravure coating method, bar coating method, roll coating method, wire bar coating method, dip coating method, spray coating method, screen printing method, flexographic printing method, offset printing method and ink jet printing method. In the low molecular compound, it is preferred to use the dry film forming method, and in the polymer compound, it is preferred to use the wet film forming method.

<Uses>

The organic EL element according to the present invention is favorable for image display devices as pixels by a matrix system or a segment system with known methods. The organic EL element is also favorable for a surface emitting light source without forming pixels.

The organic EL element of the present invention is favorable for displays, back lights, electron photographs, illumination light sources, recording light sources, exposure light sources, reading light sources, signs, signboards, interiors, optical communication systems, etc.

EXAMPLE

The present invention is further described in more detail with reference to the following examples hereinafter, but it is not limited by the examples.

Synthesis Example 1

Schema 1

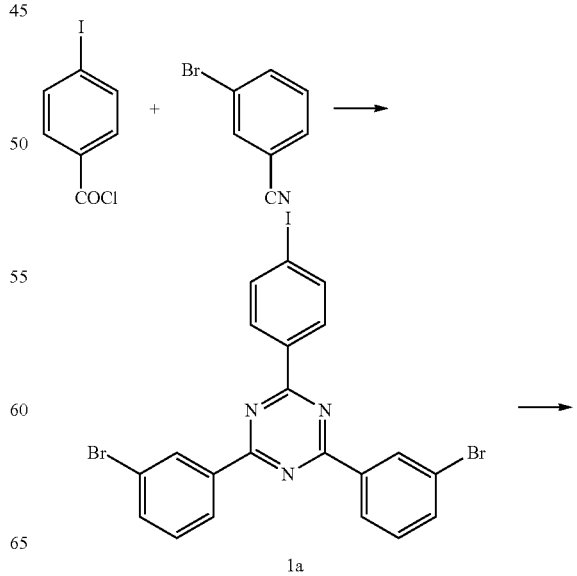

1a

73

-continued

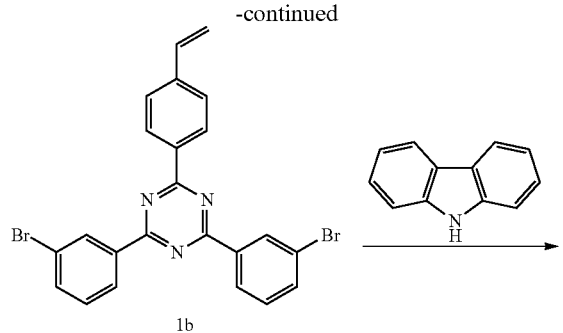

The example is described with reference to the above schema 1.

10 mmol of 4-iodobenzoyl chloride and 30 mmol of 3-bromobenzonitrile were dissolved in 50 mL of dehydrated chloroform, 10 mmol of aluminum chloride and 40 mmol of ammonium chloride were added to the solution and then heated and stirred at 50° C. for 24 hr. The solution was cooled to room temperature, and then poured to 10% hydrochloric acid and stirred for 1 hr. The mixture was subjected to extraction using chloroform and the extract was purified by column chromatography to prepare a halogenated triazine derivative (1a).

3 mmol of the resulting halogenated triazine derivative (1a), 2.8 mmol of vinyl boric acid and 1.5 mmol of tetrabutyl ammonium bromide were dissolved in 45 mL of toluene. To the mixture, a small amount of a polymerization inhibitor was added and 30 mL of 2M potassium carbonate aqueous solution was added. 0.15 mmol of tetrakis triphenylphosphine palladium was added to the mixture, and heated and refluxed for 3 hr. After the mixture was cooled to room temperature, the mixture was subjected to extraction using ethyl acetate and the extract was purified by column chromatography to prepare a halogenated vinyl monomer of triazine (1b).

2.5 mmol of the resulting halogenated vinyl monomer (1b), 5.5 mmol of carbazole and 8 mmol of tertialbutoxy sodium were dissolved in 50 mL of toluene and a small amount of a polymerization inhibitor was added. After 0.13 mmol of palladium acetate and 0.5 mmol of tri (tertialbutyl) phosphine were added to the mixture, and heated and refluxed for 2 hr. The mixture was subjected to extraction using ethyl acetate and the extract was purified by column chromatography to prepare a carbazolyl group-introduced triazine vinyl monomer (1).

74

Synthesis Example 2

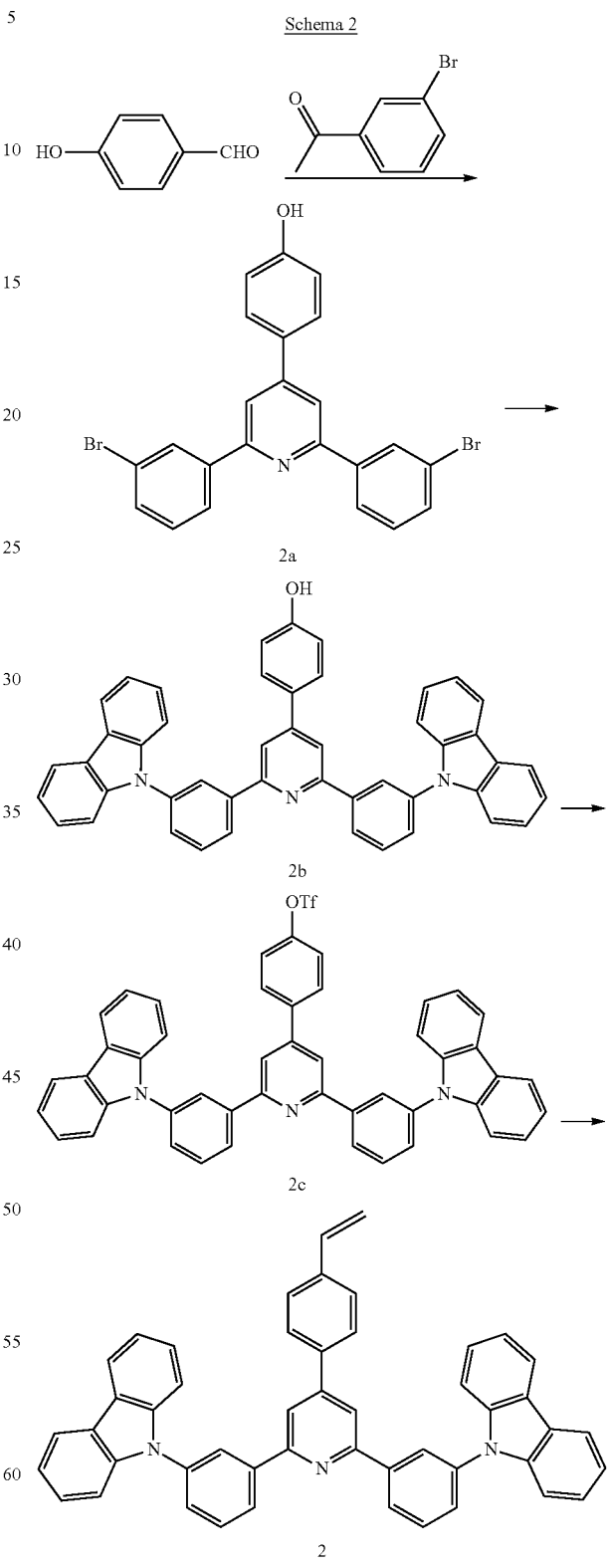

The example is described with reference to the above schema 2.

To 62.8 mmol of 3'-bromoacetophenone, 31.4 mmol of 4-hydroxybenzealdehyde and 0.4 mol of ammonium acetate, 80 mL of acetic acid was added, and heated and refluxed for 8 hr. The reaction was stopped by adding pure water, the reacted mixture was subjected to extraction using chloroform and the extract was purified by column chromatography to prepare a halogenated pyridine derivative (2a).

10 mmol of the halogenated pyridine derivative (2a), 22 mmol of carbazole and 8 mmol of tertialbutoxy sodium were dissolved in 50 mL of toluene. To the mixture, 0.13 mmol of palladium acetate and 0.5 mmol of tri (tertialbutyl) phosphine were added, and heated and refluxed for 2 hr. The mixture was subjected to extraction using ethyl acetate and the extract was purified by column chromatography to prepare a carbazolyl group-introduced pyridine derivative (2b).

9 mmol of the resulting carbazolyl group-introduced pyridine derivative (2b) was dissolved in 30 mL of pyridine and 10 mmol of anhydrous trifluorosulfonic acid was added in an ice bath. After the mixture was stirred at room temperature for 14 hr, the reaction was stopped by adding dilute hydrochloric acid. The reacted mixture was subjected to extraction using ethyl acetate and the extract was purified by column chromatography to prepare a carbazolyl group-introduced pyridine derivative (2c).

6 mmol of the carbazolyl group-introduced pyridine derivative (2c), 6.6 mmol of vinyl borate and 3 mmol of tetrabutyl ammonium bromide were dissolved in 75 mL of toluene. To the mixture, a small amount of a polymerization inhibitor was added and then 50 mL of 2M potassium carbonate aqueous solution was added. To the mixture, 0.3 mmol of tetrakistriphenyl phosphine palladium was added, and refluxed with heating for 3 hr. After the mixture was cooled to room temperature, the mixture was subjected to extraction using ethyl acetate and the extract was purified by column chromatography to prepare a carbazolyl group-introduced pyridine vinyl monomer (2).

Synthesis Example 3

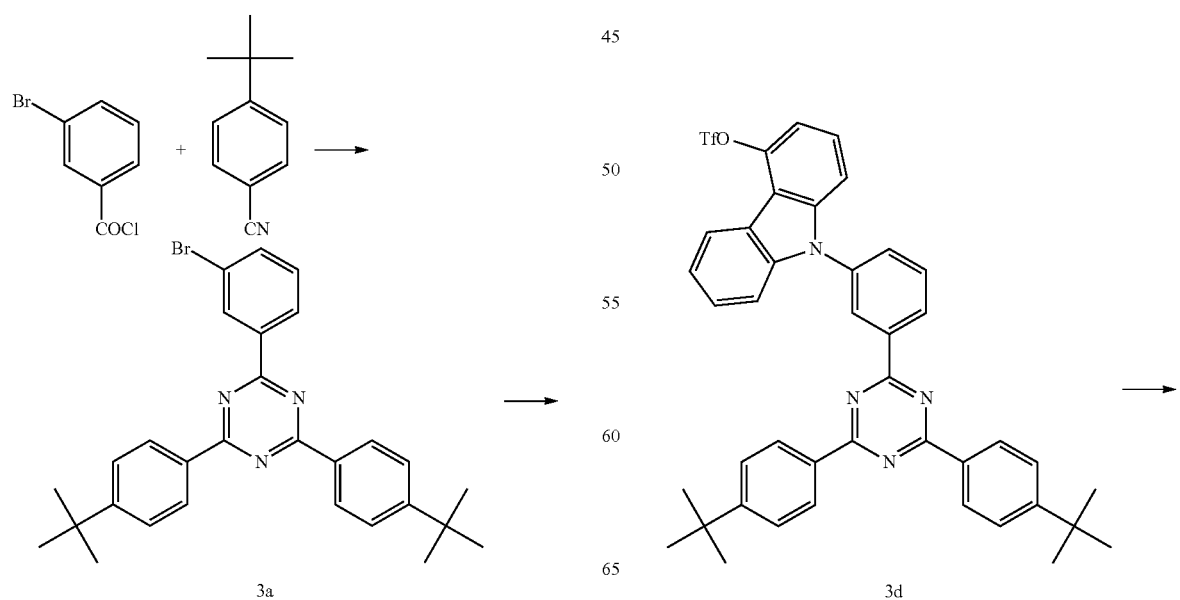

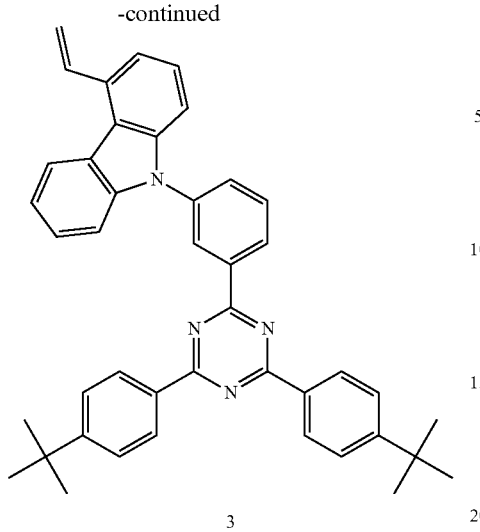

3

The example is described with reference to the above schema 3.

10 mmol of 3-bromobenzoylchloride and 30 mmol of 4-t-butylbenzonitrile were dissolved in 50 mL of dehydrated chloroform, 10 mmol of aluminum chloride and 40 mmol of ammonium chloride were added, and heated and stirred at 50° C. for 24 hr. The mixture was cooled to room temperature and poured to 10% hydrochloric acid, and stirred for 1 hr. The mixture was subjected to extraction using chloroform and the extract was purified by column chromatography to prepare a halogenated triazine derivative (3a).

3 mmol of the halogenated triazine derivative (3a), 3.3 mmol of carbazole which hydroxyl group was protected by Si group and 8 mmol of tertialbutoxy sodium were dissolved in 50 mL of toluene. To the mixture, 0.13 mmol of palladium acetate and 0.5 mmol of tri (tertialbutyl) phosphine were added, and heated and refluxed for 2 hr. The mixture was subjected to extraction using ethyl acetate and the extract was purified by column chromatography to prepare a carbazolyl group-introduced triazine derivative (3b).

2.8 mmol of the resulting carbazolyl group-introduced triazine derivative (3b) was dissolved in 20 mL of tetrahydrofurane and 9 mmol of tetrabutyl ammonium fluoride was added in an ice bath. The mixture was stirred at room temperature for 1 hr, was subjected to extraction using ethyl acetate and the extract was purified by column chromatography to prepare a carbazolyl group-introduced triazine derivative (3c).

2.7 mmol of the carbazolyl group-introduced triazine derivative (3c) was dissolved in 10 mL of pyridine. To the mixture, 3 mmol of anhydrous trifluorosulfonic acid was added in an ice bath. The mixture was stirred at room temperature for 14 hr and then the reaction was stopped by using dilute hydrochloric acid. The mixture was subjected to extraction using ethyl acetate and the extract was purified by column chromatography to prepare a carbazolyl group-introduced triazine derivative (3d).

2.5 mmol of the carbazolyl group-introduced triazine derivative (3d), 3 mmol of vinyl boric acid and 1.3 mmol of tetrabutylammonium bromide were dissolved in 45 mL of toluene. To the mixture, a small amount of a polymerization inhibitor was added and then 30 mL of 2M potassium carbonate aqueous solution was added. To the mixture, 0.13 mmol of tetrakistriphenylphosphine palladium was added, and heated and refluxed for 3 hr. After the mixture was cooled to room temperature, the mixture was subjected to extraction using ethyl acetate and the extract was purified by column chromatography to prepare a carbazolyl group-introduced triazine vinyl monomer (3).

Synthesis Example 4

Scheme 4

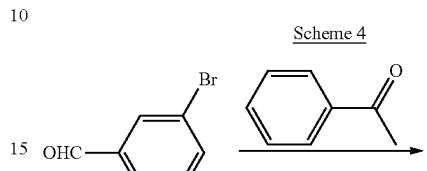

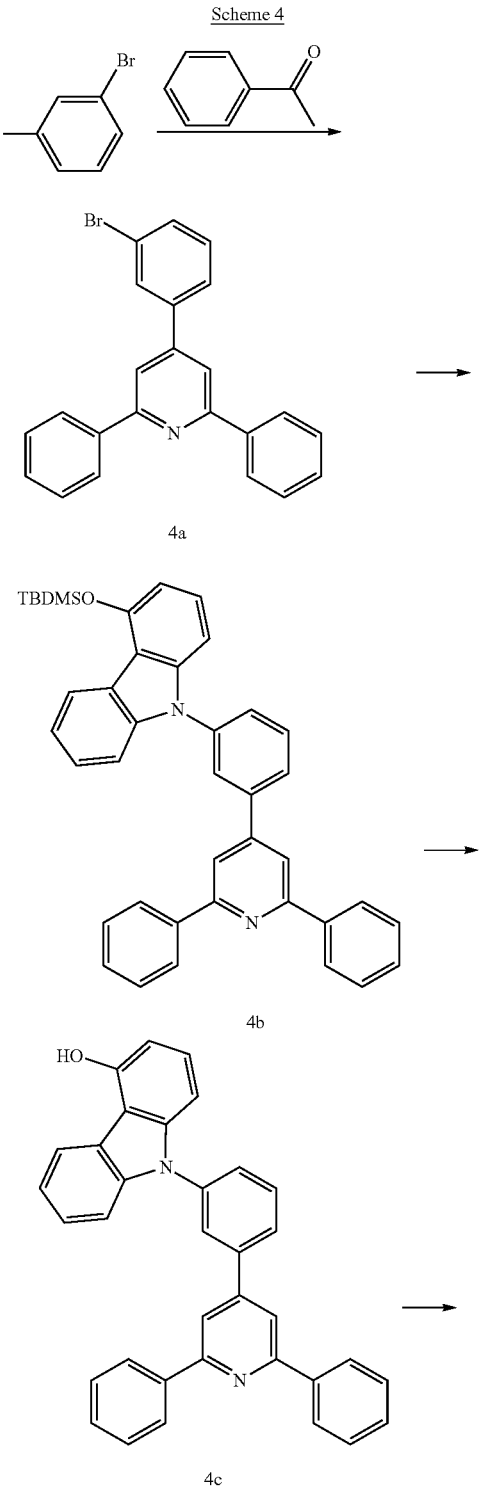

-continued

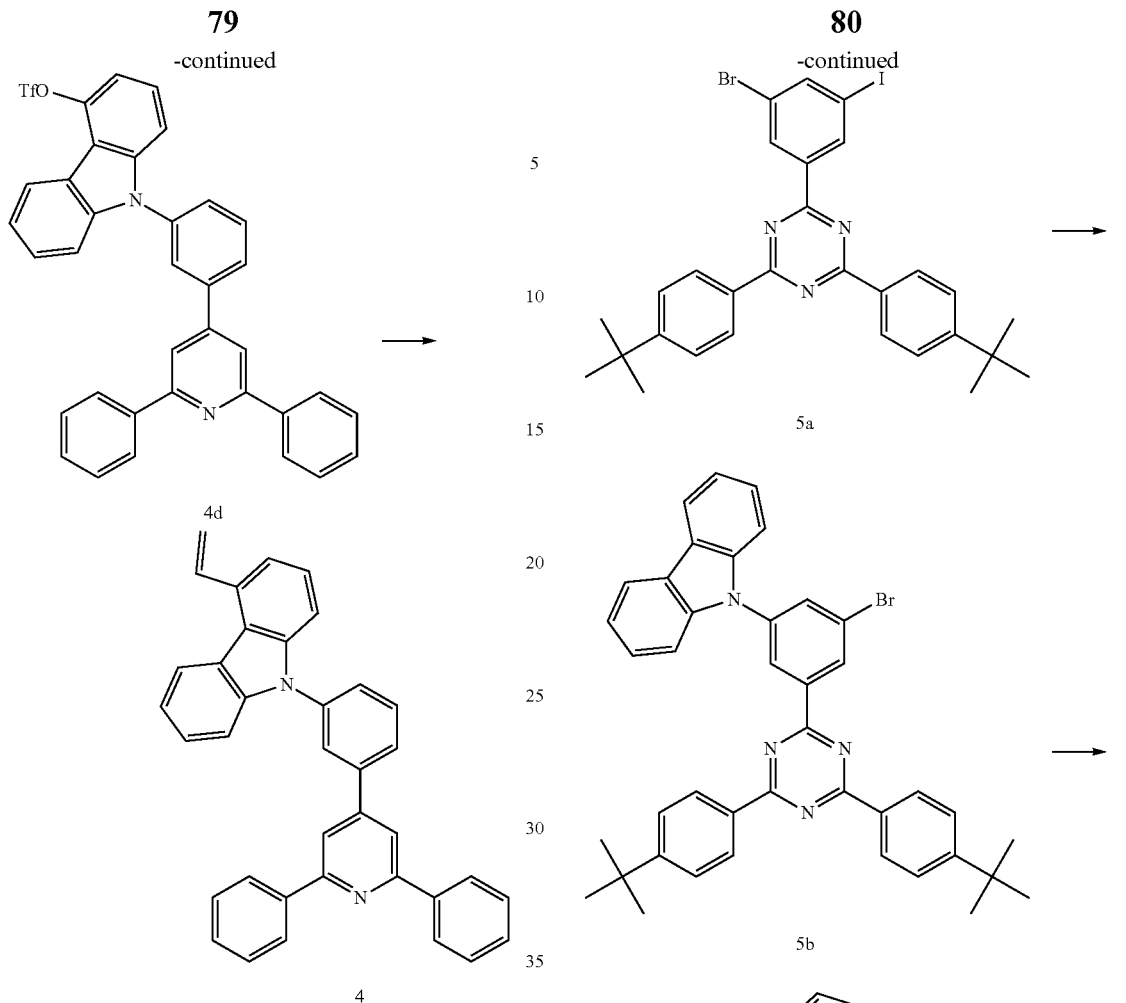

The example is described with reference to the above schema 4.

80 mL of acetic acid was added to 62.8 mmol of acetophenone, 31.4 mmol of 3-bromobenzaldehyde and 0.4 mmol of ammonium acetate, and heated and refluxed for 8 hr. The reaction was stopped by adding pure water and the reacted mixture was subjected to extraction using chloroform and the extract was purified by column chromatography to prepare a halogenated pyridine derivative (4a).

The synthesis was carried out in the same manner in the synthesis example 3 except for using the halogenated pyridine derivative (4a), to prepare a carbazolyl group-introduced pyridine vinyl monomer (4).

Synthesis Example 5

Schema 5

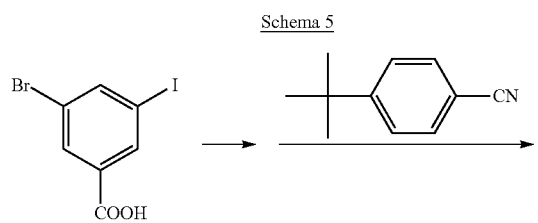

The example is described with reference to the above schema 5.

10 mmol of 3-bromo-5-iodo benzoic acid was dissolved in 100 mL of dichloroethane, 10 mL of thionylchloride was added to the mixture, and heated and refluxed for 2 hr. A solvent was distilled off from the reaction solution under reduced pressure, and thereafter 30 mmol of 4-t-butylbenzonitrile and 75 mL of chloroform were added to the solution. Next, 10 mmol of aluminum chloride and 40 mmol of ammonium chloride were added to the solution, and heated and stirred at 50° C. for 24 hr. After the mixture was cooled to room temperature, the mixture was poured to 10% hydrochloric acid and stirred for 1 hr. The mixture was subjected to extraction using chloroform and the extract was purified by column chromatography, to prepare a dihalogenated triazine derivative (5a).

3 mmol of the dihalogenated triazine derivative (5a) and 3 mmol of carbazole were dissolved in 15 mL of dimethylsulphoxide, and 9 mmol of potassium carbonate, and 0.15 mmol of copper iodide and 0.6 mmol of L-prolin were added to the mixture and then reacted at 80° C. for 6 hr. The reaction solution was cooled to room temperature and subjected to filtration with Celite and extraction using chloroform. The extract was purified by column chromatography, to prepare a carbazole group-introduced halogenated triazine derivative (5b).

The resulting carbazole group-introduced halogenated triazine derivative was subjected to Suzuki coupling with vinyl boric acid to prepare a carbazolyl group-introduced triazine vinyl monomer (5).

Synthesis Example 6

Schema 6

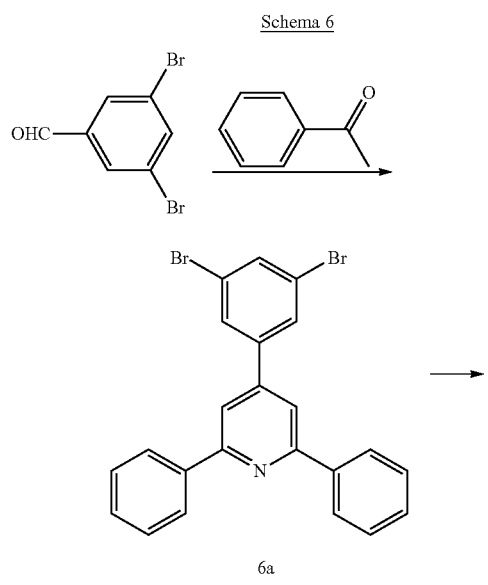

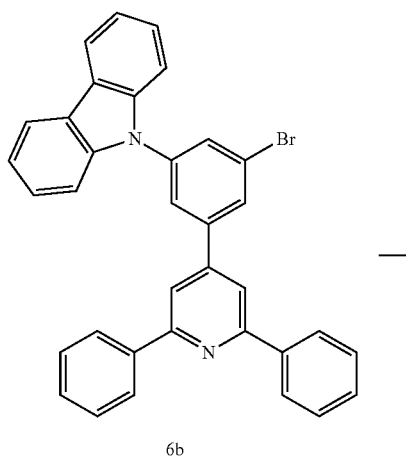

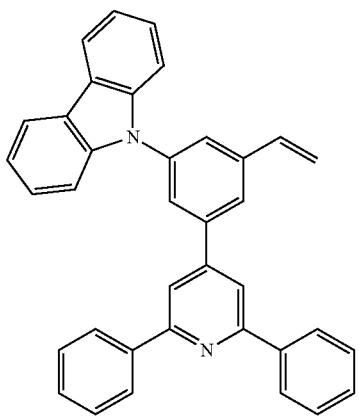

6

The example is described with reference to the above schema 6.

80 mL of acetic acid was added to 62.8 mmol of acetophenone, 31.4 mmol of 3,5-dibromobenzaldehyde and 0.4 mol of ammonium acetate. The mixture was heated and refluxed for 8 hr. The reaction was stopped by adding pure water. The reaction mixture was subjected to extraction using chloroform and the extract was purified by column chromatography to prepare a dihalogenated pyridine derivative (6a).

10 mmol of the dihalogenated pyridine derivative (6a) and 10 mmol of carbazole were dissolved in 30 mL of dimethylsulphoxide, and 30 mmol of cesium carbonate, and 0.5 mmol of copper iodide and 2 mmol of cyclohexane diamine were added to the mixture and then reacted at 80° C. for 6 hr. The reaction solution was cooled to room temperature and subjected to filtration with Celite and extraction using chloroform. The extract was purified by column chromatography, to prepare a carbazole group-introduced halogenated pyridine derivative (6b).

The resulting carbazole group-introduced halogenated pyridine derivative (6b) was subjected to Suzuki coupling with vinyl boric acid to prepare a carbazole group-introduced pyridine vinyl monomer (6).

Synthesis Example 7

Schema 7

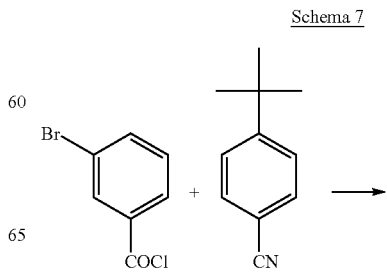

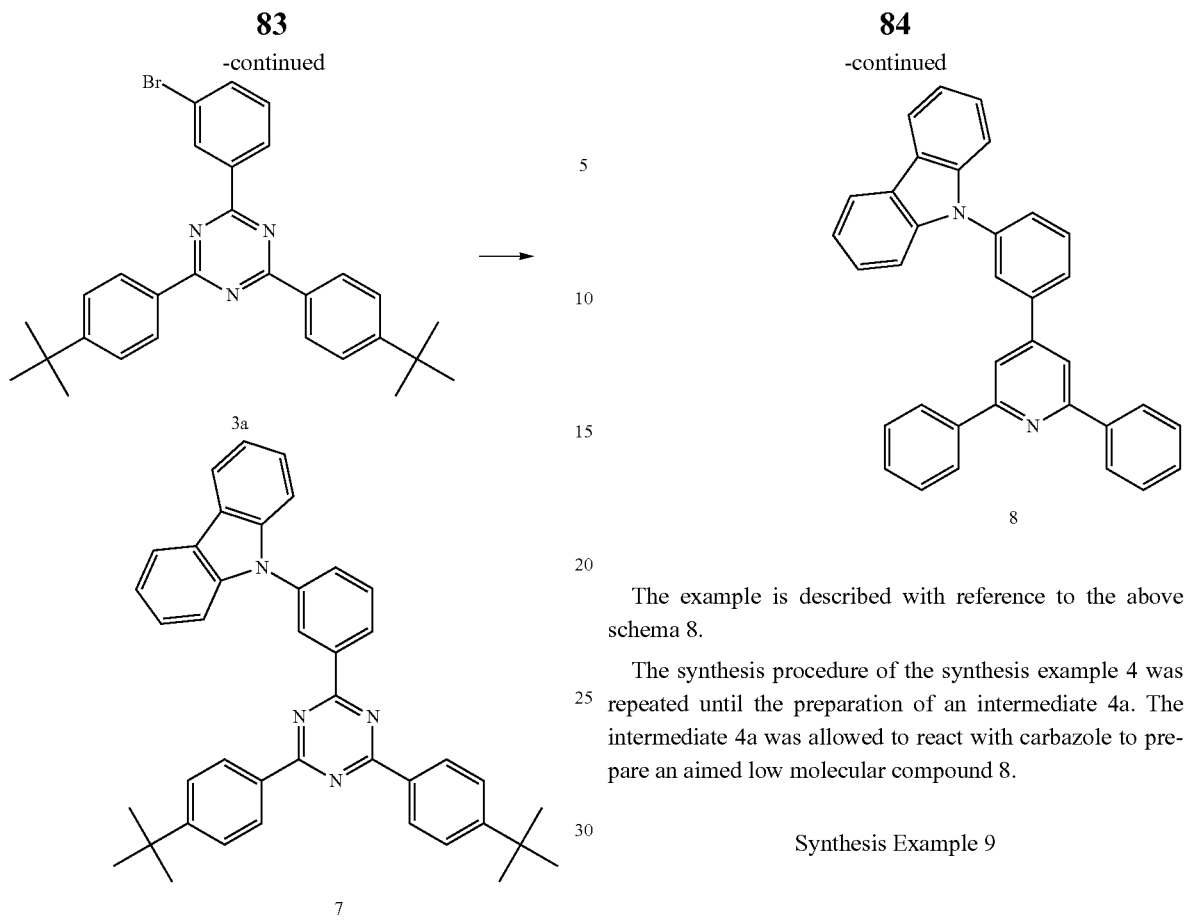

The example is described with reference to the above schema 7.

The synthesis procedure of the synthesis example 3 was repeated until the preparation of an intermediate 3a. The intermediate 3a was allowed to react with carbazole to prepare an aimed low molecular compound 7.

Synthesis Example 8

The example is described with reference to the above schema 8.

The synthesis procedure of the synthesis example 4 was repeated until the preparation of an intermediate 4a. The intermediate 4a was allowed to react with carbazole to prepare an aimed low molecular compound 8.

Synthesis Example 9

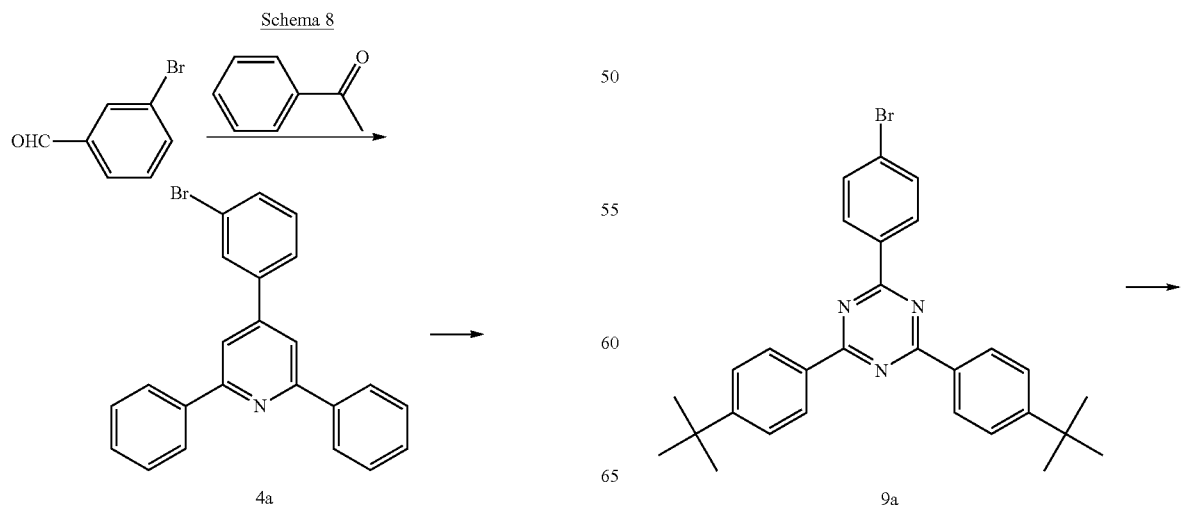

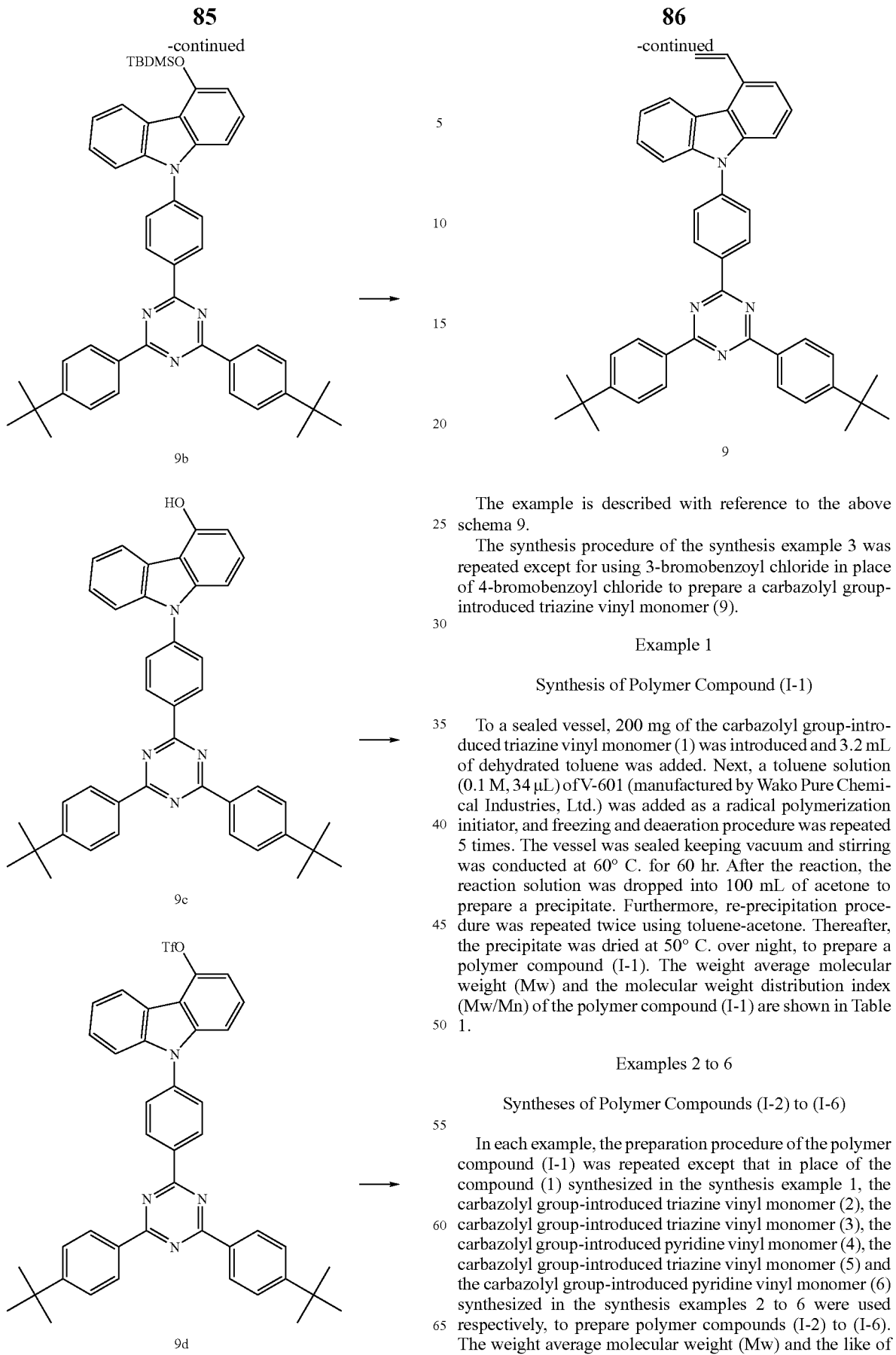

The example is described with reference to the above schema 9.

The synthesis procedure of the synthesis example 3 was repeated except for using 3-bromobenzoyl chloride in place of 4-bromobenzoyl chloride to prepare a carbazolyl group-introduced triazine vinyl monomer (9).

Example 1

Synthesis of Polymer Compound (I-1)

To a sealed vessel, 200 mg of the carbazolyl group-introduced triazine vinyl monomer (1) was introduced and 3.2 mL of dehydrated toluene was added. Next, a toluene solution (0.1 M, 34 μL) of V-601 (manufactured by Wako Pure Chemical Industries, Ltd.) was added as a radical polymerization initiator, and freezing and deaeration procedure was repeated 5 times. The vessel was sealed keeping vacuum and stirring was conducted at 60° C. for 60 hr. After the reaction, the reaction solution was dropped into 100 mL of acetone to prepare a precipitate. Furthermore, re-precipitation procedure was repeated twice using toluene-acetone. Thereafter, the precipitate was dried at 50° C. over night, to prepare a polymer compound (I-1). The weight average molecular weight (Mw) and the molecular weight distribution index (Mw/Mn) of the polymer compound (I-1) are shown in Table 1.

Examples 2 to 6

Syntheses of Polymer Compounds (I-2) to (I-6)

In each example, the preparation procedure of the polymer compound (I-1) was repeated except that in place of the compound (1) synthesized in the synthesis example 1, the carbazolyl group-introduced triazine vinyl monomer (2), the carbazolyl group-introduced triazine vinyl monomer (3), the carbazolyl group-introduced pyridine vinyl monomer (4), the carbazolyl group-introduced triazine vinyl monomer (5) and the carbazolyl group-introduced pyridine vinyl monomer (6) synthesized in the synthesis examples 2 to 6 were used respectively, to prepare polymer compounds (I-2) to (I-6). The weight average molecular weight (Mw) and the like of the resulting polymer compound are shown in Table 1.

Example 7

Synthesis of Polymer Compound (II-1)

To a sealed vessel, 50 mg of the compound (1) synthesized in the synthesis example 1 and 100 mg of a hole-transporting polymerizable compound represented by the following formula (8-3) were introduced and 2.6 mL of dehydrated toluene was added. Next, a toluene solution (0.1 M, 53 µL) of V-601 (manufactured by Wako Pure Chemical Industries, Ltd.) was added, and freezing and deaeration procedure was repeated 5 times. The vessel was sealed keeping vacuum and stirring was conducted at 60° C. 60 hr. After the reaction, the reaction solution was dropped into 100 mL of acetone to prepare a precipitate. Furthermore, re-precipitation procedure was repeated twice using toluene-acetone. Thereafter, the precipitate was dried at 50° C. over night, to prepare a polymer compound (II-1). The weight average molecular weight (Mw) and the molecular weight distribution index (Mw/Mn) of the polymer compound (II-1) are shown in Table 1. The polymer compound had a value of m/(m+n), as determined by the results of ICP element analysis and $^{13}$C-NMR measurement, of 0.64.

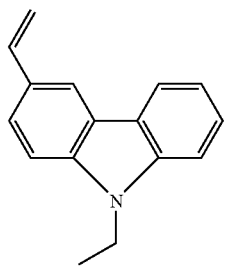

(8-3)

Examples 8 to 12

Syntheses of Polymer Compounds (II-2) to (II-6)

In each example, the preparation procedure of the polymer compound (II-1) was repeated except that in place of the compound (1) synthesized in the synthesis example 1, the compounds (2) to (6) synthesized in the synthesis examples 2 to 6 were used respectively, to prepare polymer compounds (II-2) to (II-6). The weight average molecular weight and the like of the resulting polymer compound are shown in Table 1.

Example 13

Synthesis of Polymer Compound (III-1)

To a sealed vessel, 60 mg of the compound (1) synthesized in the synthesis example 1 and 120 mg of a hole-transporting polymerizable compound (8-3), the polymer compound having phosphorescent properties represented by the following formula (X) were introduced and 3.1 mL of dehydrated toluene was added. Next, a toluene solution (0.1 M, 64 µL) of V-601 (manufactured by Wako Pure Chemical Industries, Ltd.) was added, and freezing and deaeration procedure was repeated 5 times. The vessel was sealed keeping vacuum and stirring was conducted at 60° C. for 60 hr. After the reaction, the reaction solution was dropped into 100 mL of acetone to prepare a precipitate. Furthermore, re-precipitation procedure was repeated twice using toluene-acetone. Thereafter, the precipitate was dried at 50° C. over night, to prepare a polymer compound (III-1). The weight average molecular weight (Mw) and the molecular weight distribution index (Mw/Mn) of the polymer compound (III-1) are shown in Table 1. The polymer compound had a value of m/(m+n), as determined by the results of ICP element analysis and $^{13}$C-NMR measurement, of 0.68, and had a value of x/(x+y) of 0.16.

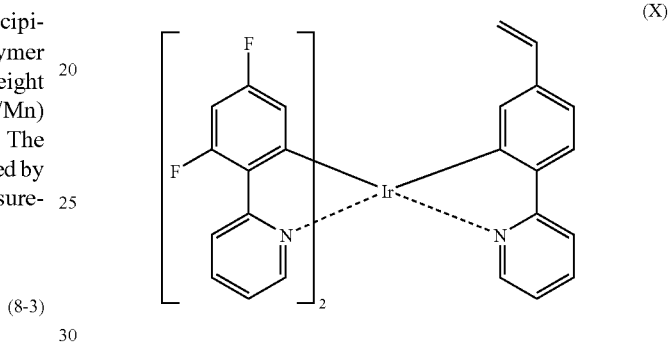

(X)

Examples 14 to 18

Syntheses of Polymer Compounds (III-2) to (III-6)

In Each Example, the Preparation Procedure of the Polymer compound (III-1) was repeated except that in place of the compound (1) synthesized in the synthesis example 1, the compounds (2) to (6) synthesized in the synthesis examples 2 to 6 were used respectively, to prepare polymer compounds (III-2) to (III-6). The weight average molecular weight and the like of each of the resulting polymers compounds (III-2) to (III-6) are shown in Table 1.

Example 19

Synthesis of Polymer Compound (IV-1)

To a sealed vessel, 50 mg of the compound (1) synthesized in the synthesis example 1, 200 mg of a hole-transporting polymerizable compound (8-3) and 50 mg of an electron-transporting polymerizable compound were introduced and 5.5 mL of dehydrated toluene was added. Next, a toluene solution (0.1 M, 110 µL) of V-601 (manufactured by Wako Pure Chemical Industries, Ltd.) was added, and freezing and deaeration procedure was repeated 5 times. The vessel was sealed keeping vacuum and stirring was conducted at 60° C. for 60 hr. After the reaction, the reaction solution was dropped into 100 mL of acetone to prepare a precipitate. Furthermore, re-precipitation procedure was repeated twice using toluene-acetone. Thereafter, the precipitate was dried at 50° C. over night, to prepare a polymer compound (IV-1). The weight average molecular weight (Mw) and the molecular weight distribution index (Mw/Mn) of the polymer compound (IV-1) are shown in Table 1. The polymer compound had a value of m/(m+n), as determined by the results of ICP element analysis and $^{13}$C-NMR measurement, of 0.68, and had a value of x/(x+y) of 0.16.

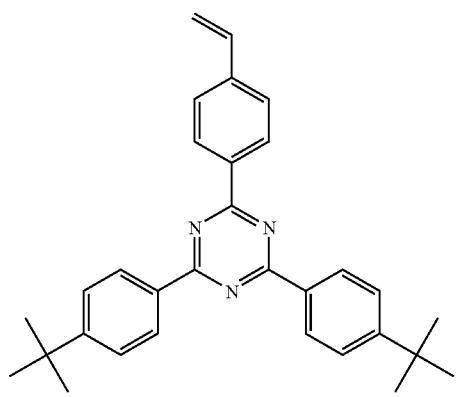

(Y)

Examples 20 to 24

Syntheses of Polymer compounds (IV-2) to (IV-6)

In each example, the preparation procedure of the polymer compound (IV-1) was repeated except that in place of the compound (1) synthesized in the synthesis example 1, the compounds (2) to (6) synthesized in the synthesis examples 2 to 6 were used respectively, to prepare polymer compounds (IV-2) to (IV-6). The weight average molecular weight and the like of each of the resulting polymers compounds (IV-2) to (IV-6) are shown in Table 1.

TABLE 1

| Example | Polymer compound | Weight average molecular weight (Mw) | Molecular weight distribution Index (Mw/Mn) |
|---|---|---|---|
| 1 | I-1 | 73,000 | 1.97 |
| 2 | I-2 | 68,000 | 1.84 |
| 3 | I-3 | 68,000 | 1.48 |
| 4 | I-4 | 57,000 | 1.56 |
| 5 | I-5 | 54,000 | 2.00 |
| 6 | I-6 | 61,000 | 1.82 |
| 7 | II-1 | 68,000 | 2.12 |
| 8 | II-2 | 56,000 | 1.79 |
| 9 | II-3 | 69,000 | 1.88 |
| 10 | II-4 | 66,000 | 1.94 |
| 11 | II-5 | 62,000 | 1.64 |
| 12 | II-6 | 59,000 | 1.56 |
| 13 | III-1 | 63,000 | 1.59 |
| 14 | III-2 | 68,000 | 1.64 |
| 15 | III-3 | 53,000 | 1.87 |
| 16 | III-4 | 71,000 | 1.84 |
| 17 | III-5 | 62,000 | 1.55 |
| 18 | III-6 | 58,000 | 1.47 |
| 19 | IV-1 | 70,000 | 1.81 |
| 20 | IV-2 | 75,000 | 1.95 |
| 21 | IV-3 | 67,000 | 2.04 |
| 22 | IV-4 | 59,000 | 1.65 |
| 23 | IV-5 | 71,000 | 1.75 |
| 24 | IV-6 | 69,000 | 1.69 |

Example 25

Preparation of Organic EL Element 1 and Measurement of Luminous Brightness Thereof First, the polymer compound (I') was synthesized in the following manner. To a sealed vessel, 200 mg of a polymerizable compound having hole-transporting properties (8-3) was introduced and 4.5 mL of dehydrated toluene was added. Next, a toluene solution (0.1 M, 90 μL) of V-601 (manufactured by Wako Pure Chemical Industries, Ltd.) was added, and freezing and deaeration procedure was repeated 5 times. The vessel was sealed keeping vacuum and stirring was conducted at 60° C. for 60 hr. After the reaction, the reaction solution was dropped into 100 mL of acetone to prepare a precipitate. Furthermore, re-precipitation procedure was repeated twice using toluene-acetone. Thereafter, the precipitate was dried at 50° C. over night, to prepare a polymer compound (I').

Next, an organic EL element was prepared in the following manner. Firstly, on ITO-having substrate such that two striped ITO (indium tin oxide) electrode (cathode) having a width of 4 mm were formed on one surface of a glass substrate having a square of 25 mm, poly (3,4-ethylenedioxythiophene)/polystyrene sulfonic acid (Trade Name: Baytron P manufactured by Bayer AG) was applied by a spin coating method at a rotation number of 3500 rpm for a coating time of 40 sec. Thereafter, the substrate was by a vacuum dryer under reduced pressure at 60° C. for 2 hr to prepare an anode buffer layer. The resulting anode buffer layer had a film thickness of about 50 nm. Next, 40.5 mg of the polymer compound (I-1), 9 mg of the phosphorescent compound (E-38) and 40.5 mg of the polymer compound (I') were dissolved in 2910 mg of toluene, the solution was filtered off with a filter having a hole diameter of 0.2 μm to prepare a coating solution. Subsequently, on the anode buffer layer, the coating solution was applied by a spin coating method at a rotation number of 3000 rpm for a coating time of 30 sec. After the application, the substrate was dried at room temperature (25° C.) for 30 min to form a luminous layer. The resulting luminous layer had a film thickness of about 100 nm.

Next, the substrate having the luminous layer was installed in a vapor deposition device. Subsequently, barium and aluminum were co-vapor deposited in a weight ratio of 1:10 so that two striped cathodes having a width of 3 mm were formed crosswise to the direction of orientation of the anode. The resulting cathode has a film thickness of about 50 nm.

Lastly a lead wire (wiring) was installed to the anode and the cathode in an argon atmosphere to prepare four organic EL elements having a length of 4 mm and a width of 3 mm. The four organic EL elements are combined to prepare an organic EL element 1. A voltage was applied on the organic EL element 1 using a programmable direct current voltage/electric current power source (TR6143 manufactured by Advantest Co.) to emit light.

The luminous brightness was measured using a luminance meter (BM-8 manufactured by Tpocon Co.). Concerning the organic EL element 1 thus formed, the maximum external quantum efficiency, the maximum brightness, the driving voltage and the half-life of brightness in driving at a constant current by lighting at an initial brightness of 100 cd/m$^2$ are shown in Table 2.

Examples 26 to 30

Preparation of Organic EL Elements 2 to 6 and Measurement of Luminous Brightness Thereof In each example, the procedure of Example 25 was repeated except for using each of the polymer compounds (I-2) to (I-6) in place of the polymer compound (I-1) to prepare organic EL elements 2 to 6. The luminous brightness thereof was measured. Concerning the organic EL elements 2 to 6, the maximum external quantum efficiency, the maximum brightness, the driving voltage and the half-life of brightness in driving at a constant current by lighting at an initial brightness of 100 cd/m² are shown in Table 2.

Examples 31 to 36

Preparation of Organic EL Elements 7 to 12 and Measurement of Luminous Brightness Thereof In each example, the procedure of Example 25 was repeated except for using each of the polymer compounds (II-1) to (II-6) in place of the polymer compound (I-1) and the polymer compound (I') to prepare organic EL elements 7 to 12. The luminous brightness thereof was measured. Concerning the organic EL elements 7 to 12, the maximum external quantum efficiency, the maximum brightness, the driving voltage and the half-life of brightness in driving at a constant current by lighting at an initial brightness of 100 cd/m² are shown in Table 2.

Examples 37 to 42

Preparation of Organic EL Elements 13 to 18 and Measurement of Luminous Brightness Thereof In each example, the procedure of Example 31 was repeated except for using each of the polymer compounds (III-1) to (III-6) in place of the polymer compound (II-1) and the luminous compound (E-38) to prepare organic EL elements 13 to 18. The luminous brightness thereof was measured. Concerning the organic EL elements 13 to 18, the maximum external quantum efficiency, the maximum brightness, the driving voltage and the half-life of brightness in driving at a constant current by lighting at an initial brightness of 100 cd/m² are shown in Table 2.

Examples 43 to 48

Preparation of Organic EL Elements 18 to 24 and Measurement of Luminous Brightness Thereof In each example, the procedure of Example 37 was repeated except for using each of the polymer compounds (IV-1) to (IV-6) in place of the polymer compound (III-1) to prepare organic EL elements 19 to 24. The luminous brightness thereof was measured. Concerning the organic EL elements 19 to 24, the maximum external quantum efficiency, the maximum brightness, the driving voltage and the half-life of brightness in driving at a constant current by lighting at an initial brightness of 100 cd/m² are shown in Table 2.

Comparative Example 1

Preparation of Organic EL Element 25 and Measurement of Luminous Brightness Thereof The procedure of Example 25 was repeated except for using a low molecule compound 7 in place of the polymer compound (I-1) to prepare an organic EL element 25. The luminous brightness thereof was measured. Concerning the organic EL element 25, the maximum external quantum efficiency, the maximum brightness, the driving voltage and the half-life of brightness in driving at a constant current by lighting at an initial brightness of 100 cd/m² are shown in Table 2.

Comparative Example 2

Preparation of Organic EL Element 26 and Measurement of Luminous Brightness Thereof The procedure of Example 25 was repeated except for using a low molecule compound 8 in place of the polymer compound (I-1) to prepare an organic EL element 26. The luminous brightness thereof was measured. Concerning the organic EL element 26, the maximum external quantum efficiency, the maximum brightness, the driving voltage and the half-life of brightness in driving at a constant current by lighting at an initial brightness of 100 cd/m² are shown in Table 2.

Comparative Example 3

Preparation of Organic EL Element 27 and Measurement of Luminous Brightness Thereof The preparation procedure of the polymer compound (I-1) was repeated except for using the carbazolyl group-introduced triazine vinyl monomer (9) in place of the compound (1) synthesized in the synthesis example 1 to prepare a polymer compound (I"). The resulting polymer compound (I") had a weight average molecular weight of 68,000 and a molecular weight distribution index of 2.14.

The procedure of Example 25 was repeated except for using the polymer compound (I") in place of the polymer compound (I-1) to prepare an organic EL element 27. The luminous brightness thereof was measured. Concerning the organic EL element 27, the maximum external quantum efficiency, the maximum brightness, the driving voltage and the half-life of brightness in driving at a constant current by lighting at an initial brightness of 100 cd/m² are shown in Table 2.

In the table 2, the half-life of brightness was evaluated relative to the half-life of brightness of the organic EL element 26, which is taken as 1.

TABLE 2

| | | Organic EL element | Maximum external quantum efficiency (%) | Maximum brightness (cd/m²) | Deriving voltage (V) | Half-life of brightness (Relative evaluation) |
|---|---|---|---|---|---|---|
| Ex. | 25 | 1 | 5.6 | 9,500 | 2.9 | 7 |
| | 26 | 2 | 6.0 | 7,000 | 3.6 | 5 |
| | 27 | 3 | 6.1 | 20,000 | 3.0 | 45 |
| | 28 | 4 | 5.7 | 7,000 | 3.3 | 35 |
| | 29 | 5 | 7.2 | 26,000 | 3.0 | 40 |
| | 30 | 6 | 6.3 | 27,000 | 3.5 | 40 |
| | 31 | 7 | 5.1 | 22,000 | 2.9 | 425 |
| | 32 | 8 | 6.4 | 30,000 | 3.0 | 370 |
| | 33 | 9 | 6.2 | 12,000 | 3.2 | 450 |
| | 34 | 10 | 5.4 | 28,000 | 3.2 | 390 |
| | 35 | 11 | 6.6 | 37,000 | 2.8 | 115 |
| | 36 | 12 | 6.1 | 23,000 | 3.6 | 130 |
| | 37 | 13 | 4.9 | 15,000 | 3.3 | 470 |
| | 38 | 14 | 4.1 | 11,000 | 3.4 | 415 |
| | 39 | 15 | 5.3 | 21,000 | 3.1 | 523 |
| | 40 | 16 | 4.9 | 19,000 | 3.1 | 476 |
| | 41 | 17 | 4.3 | 17,000 | 3.5 | 179 |
| | 42 | 18 | 3.9 | 12,000 | 3.7 | 165 |
| | 43 | 19 | 5.3 | 24,000 | 3.0 | 481 |

TABLE 2-continued

| Organic EL element | Maximum external quantum efficiency (%) | Maximum brightness (cd/m²) | Deriving voltage (V) | Half-life of brightness (Relative evaluation) |
|---|---|---|---|---|
| 44 | 20 | 6.5 | 32,000 | 3.1 | 439 |
| 45 | 21 | 6.4 | 18,000 | 3.2 | 538 |
| 46 | 22 | 6.1 | 31,000 | 3.3 | 482 |
| 47 | 23 | 6.8 | 23,000 | 3.2 | 206 |
| 48 | 24 | 6.9 | 34,000 | 3.4 | 181 |
| Com. 1 | 25 | 1.2 | 7,000 | 3.9 | 1.5 |
| Ex. 2 | 26 | 2.6 | 10,000 | 3.3 | 1 |
| 3 | 27 | 3.7 | 11,000 | 3.4 | 2.5 |

The invention claimed is:

1. A polymer compound comprising a constituting unit derived from a monomer represented by the following formula (1):

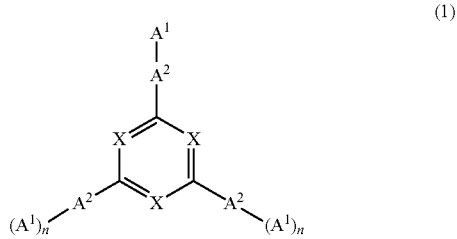

(1)

wherein in the formula (1), one of $A^1$s is a carbazolyl group, and the rest of the $A^1$s are hydrogen atoms, the $A^2$s to which the carbazolyl group is bonded is a m-phenylene group, and the rest of the $A^2$s are the following group:

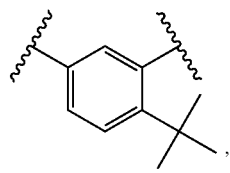

and the three Xs are all nitrogen atoms; and
two n's are independently 1 or 24.

2. The polymer compound according to claim 1 wherein the monomer represented by the formula (1) is represented by the following formula (1-i);

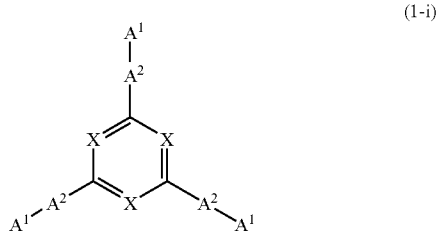

(1-i)

wherein in the formula (1-i), one of $A^1$s is a carbazolyl group, and the rest of the $A^1$s are hydrogen atoms, the $A^2$s to which the carbazolyl group is bonded is a m-phenylene group, and the rest of the $A^2$s are the following group:

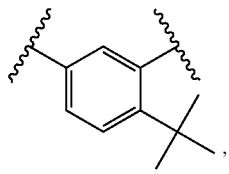 [SMILES: *c1ccc(C(C)(C)C)c(*)c1]

and the three Xs are all nitrogen atoms.

3. The polymer compound according to claim 1, which further comprises a constituting unit derived from a polymerizable compound having hole-transporting properties.

4. The polymer compound according to claim 3, wherein the polymerizable compound having hole-transporting properties has a carbazole structure or a triphenylamine structure.

5. The polymer compound according to claim 4, wherein the polymerizable compound having hole-transporting properties has a carbazole structure.

6. The polymer compound according to claim 1, which further comprises at least one of a constituting unit derived from a polymerizable compound having electron-transporting properties and a constituting unit derived from a polymerizable compound having luminous properties.

7. The polymer compound according to claim 6, wherein the polymerizable compound having luminous properties has phosphorescent properties.

8. The polymer compound according to claim 6, wherein the polymerizable compound having luminous properties is a transition metal complex.

9. The polymer compound according to claim 8, wherein the transition metal complex is an iridium complex.

10. The polymer compound according to claim 6, wherein the polymerizable compound having electron-transporting properties has an aromatic heterocyclic substituent or a triarylboron substituent.

11. The polymer compound according to claim 1, which is used for organic electroluminescence elements.

12. A luminous layer for organic electroluminescence elements comprising the polymer compound according to claim 1.

13. An organic electroluminescence element comprising at least one organic layer provided between an anode and a cathode, wherein at least one luminous layer, which is contained in the organic layer, comprises the polymer compound according to claim 1.

14. An article comprising the organic electroluminescence element according to claim 13, which is selected from displays, back lights, electro-photographs, light sources for illumination, light sources for recording, light sources for exposure, light sources for reading, markers, signboards, interior goods and optical communication systems.

15. A process for producing an organic electroluminescence element, which process comprises a step of forming an organic layer comprising at least one luminous layer according to claim 12 on an anode, and a step of forming a cathode on the organic layer.

* * * * *